(12) United States Patent
Lin

(10) Patent No.: US 7,071,303 B2
(45) Date of Patent: Jul. 4, 2006

(54) ANDROGEN REGULATED PROSTATE SPECIFIC NUCLEIC ACIDS

(75) Inventor: Biaoyang Lin, Bothell, WA (US)

(73) Assignee: Institute For Systems Biology, Seattle, WA (US)

( * ) Notice: Subject to any disclaimer, the term of this patent is extended or adjusted under 35 U.S.C. 154(b) by 397 days.

(21) Appl. No.: 09/821,812

(22) Filed: Mar. 28, 2001

(65) Prior Publication Data

US 2003/0166520 A1 Sep. 4, 2003

(51) Int. Cl.
*C07K 14/00* (2006.01)

(52) U.S. Cl. ............... 530/350; 435/7.1; 424/184.1; 424/185.1; 424/192.1

(58) Field of Classification Search .......... 530/350; 425/7.1; 424/184.1, 185.1, 192.1; 514/2; 435/387.1
See application file for complete search history.

(56) References Cited

U.S. PATENT DOCUMENTS

| 4,376,110 A | 3/1983 | David et al. |
| 4,778,751 A | 10/1988 | El Shami et al. |

FOREIGN PATENT DOCUMENTS

| WO | WO 00/65067 | 11/2000 |

OTHER PUBLICATIONS

Jansen, M et al, 1995, Pediatric Res, 37 (6): 681–686.*
Alberts et al..Molecular Biology of the Cell, 3rd edition, 1994, p. 465.*
Shantz and Pegg. Int J of Biochem and Cell Biol., 1999, vol. 31, pp. 107–122.*
McClean and Hill. Eur J of Cancer, 1993, vol. 29A, pp. 2243–2248.*
Fu et al. EMBO Journal, 1996, vol. 15, pp. 4392–4401.*
Yokota, J et al. Oncogene, 1988, vol. 3, pp. 471–475.*
Drexler et . Leukemia and Lymphoma, 1993, 9:1–25.*
Embleton et al. Immunol Ser, 1984, 23:181–207.*
Hsu et al. in: Tissue Culture Methods and Applications, Kruse and Patterson, Eds, 1973, Academic Press, NY, see abstract, p. 764.*
Mustafa O et al, 1996, Intl J Oncology, 8(5): 883–888.*
Freshney et al. In: Culture of Animal Cells, A Manual of Basic Technique, Alan R. Liss, Inc., 1983, New York, p4.*
Dermer . Bio/Technology, 1994, 12:320.*
Burgess et al. Journal of Cell Biology, 1990, 11: 2129–2138.*
Lazar et al. Molecular and Cell Biology, 1988, 8: 1247–1252.*
Tao et al. The Journal of Immunology, 1989, 143(8): 2595–2601.*
Gillies et al. Human Antibodies and Hybridomas, 1990, 1(1): 47–54).*
Rosen, CA et al, 2000, Genbank Sequence Database (Accession No: AAB53386, and MPSRCH search report, 2002, us–09–821–812–5.rag, p. 2.*
Emerson SU et al, 1999, Genbank Sequence Database (Accession No: AAW93405 and MPSRCH search report, 2002, us–09–821–812–5.rag, p. 5.*
GenBank Accession No.: A55991—Effector cell proteinase receptor 1 splice form 1b—human.

(Continued)

*Primary Examiner*—Susan Ungar
*Assistant Examiner*—Minh-Tam Davis
(74) *Attorney, Agent, or Firm*—McDermott Will & Emery LLP

(57) ABSTRACT

The present invention provides novel androgen regulated nucleic acid molecules. Related polypeptides and diagnostic methods also are provided.

3 Claims, 22 Drawing Sheets

```
TAGTTTGTATTTTTCATTACCAGCAAGGGTAAACAGTTATCCATGACCCATTTCTATGTTCTCGT
GGCATGCTTCCATGTACTGCCTCTGCATGCAGCAGGCCACCTCGGGCAGAGCCTAAAGCATGTGA
TAAATGAAATGCTATCACAATACAGGTTGTGTCTGAAAAACAAATGGCAACTTATTATCCAAGAT
CAATGAAGGAAAAAGCAAATTTACTAAAATATTTCTTTATTTGAATAAGGTCAATGCCATTTCTT
GAATTCCAGCTAGCATCAAATAATCAGGAAAAAAAAAACTTGACAAAATGTTATCCAATTGAAAT
TGACAGTGGATAGAAAACCCTTTTAAACTTTAAGTAATGTCATAAAAGAAATATATTAAACAAGC
AACAGACAGATCTAAAAAGTTCCAAGTGTGGATTTCACATTAGATCTTATAAATTAAAAAAATCC
TCAATATAATCATTTGTTCACTATCTTCTTTCAATAAGCACATGGACAGGGAAAGATAATCACAC
CTTAATATTCACAACTGCTATTTGTGTTCTTTACAAAAATTGTATCTCTGCAATGCAGTGAGGCA
GGCAATCCCTTGTTCAAGTCATTTCTGTTTTCCCTAAGTTATCAAAAAGTACAACTGTCTGATAT
AAATTGTTACCATAATCACAATCAGGAAGGCAAAGAAGCTTTAGCAGGCAGGCTTGAAGATGGGA
GTTTTCATGGCTTGACCATGAATGATCTCAAGATGATTTCATAAGATTAAAAGCCATCACGAAAA
TACTGAAAGCAACAGGTAATAATCTGGATTCAGTCTGTAGTTGCTCATGAACCACGCGTTTTAAT
AAAAGGAACATTAAGTAAATTGTAGGTATAAAAGAATCAGTGCATATCTGTTAATGTCATTGACA
ATAAAAATATATTATCTTCTCAGCTCAGCTCTAAATTAACAAAACACCTATTTTTTTTTTCCCAC
TCCTCATTTTAGTGGTTCTCAAACATTGGTGTGCTCAGAATCTCCTGAGGT
```

OTHER PUBLICATIONS

GenBank Accession No.: AA 249370—Human fetal heart, Lambda ZAP Express *Homo sapiens* cDNA 5', mRNA sequence.
GenBank Accession No.: AA404252—Soares ovary tumor NbHOT *Homo sapiens* cDNA clone IMAGE:725087 5', mRNA sequence.
GenBank Accession No.: AA659693—Homo sapiens cDNA clone IMAGE:1218900 3', mRNA sequence.
GenBank Accession No.: AAF58858—gene product (*Drosophila melanogaster*).
GenBank Accession No.: AE003831—*Drosophila melanogaster* genomic scaffold 142000013386047 section 12 of 52, complete sequence.
GenBank Accession No.: AF086168—*Homo sapiens* full length insert cDNA clone ZB82D09.
GenBank Accession No.: AF086186—*Homo sapiens* full length insert cDNA clone ZC30F12.
GenBank Accession No.: AF224278—*Homo sapiens* PMEPA1 protiein (PMEPA1) mRNA, complete.
GenBank Accession No.: AI133138—Human fetal liver cDNA library *Homo sapiens* cDNA, mRNA sequence.
GenBank Accession No.: AI299663—*Homo sapiens* cDNA clone IMAGE:1898026 3' similar to WP:C54G7.2 CE04270 ;, mRNA sequence.
GenBank Accession No.: AK002597—Mus musculus adult male kidney cDNA, RIKEN full–length enriched library, clone:0610012F22, full insert sequence.
TenBank Accession No.: AK012931—Mus musculus 10, 11 days embryo cDNA, RIKEN full–length enriched library, clone:2810049G06, full ensert sequence.
GenBank Accession No.: AL133779—*Homo sapiens* cDNA clone DKFZp761K1213 5', mRNA sequence.
GenBank Accession No.: AV722423—*Homo sapiens* cDNA clone HTBBKF09 5', mRNA sequence.
GenBank Accession No.: AW856874—*Homo sapiens* cDNA, mRNA sequence.
GenBank Accession No.: AW861164—*Homo sapiens* cDNA, mRNA sequence.
GenBank Accession No.: AW961788—MAGE resequences, MAGG *Homo sapiens* cDNA, mRNA sequence.
GenBank Accession No.: BE391760—*Homo sapiens* cDNA clone IMAGE:3605006 5', mRNA sequence.
GenBank Accession No.: BE672465—*Homo sapiens* cDNA clone IMAGE:3222816 3', mRNA sequence.
GenBank Accession No.: BF130410—*Homo sapiens* cDNA clone IMAGE:4044432 5', mRNA sequence.
GenBank Accession No.: H59488—Soares fetal liver spleen 1NFLS *Homo sapiens* cDNA clone IMAGE:205574 5', mRNA sequence.
GenBank Accession No.: T29520—Hypothetical protein T25F10.5—*Caenorhabditis* elegans.
GenBank Accession No.: U64856—*Caenorhabditis* elegans cosmid T25F10.
GenBank Accession No.: W37688—Soares_parathyroid_tumor_NbHPA *Homo sapiens* cDNA clone IMAGE:322123 5', mRNA sequence.
GenBank Accession No.: W60959—*Homo sapiens* cDNA clone IMAGE:342125 5', mRNA sequence.
Deguchi et al., "Micrometastasis of prostate cancer to lymph nodes: detection by means of reverse transcription–polymerase chain reaction," *J. Natl. Cancer Inst.* 89:1471–1473 (1997).
Ficazzola and Taneja, "Prospects for gene therapy in human prostate cancer," *Mol. Med. Today* 4:494–504 (1998).
Hawkins et al., "PEDB: the Prostate Expression Database," *Nucleic Acids Res.* 27:204–208 (1999).
Kahn et al., "Radioimmunoscintigraphy with [111]indium labeled CYT–356 for the detection of occult prostate cancer recurrence," *Journal of Urology* 152:1490–1495 (1994).
Narod, "Genetic epidemiology of prostate cancer," *Biochim. Biophys. Acta.* 1423:F1–13 (1999).
Neal et al., "Unanswered questions in screening for prostate cancer," *Eur. J. Cancer* 36:1316–1321 (2000).
Nupponen and Visakorpi, "Molecular biology of progression of prostate cancer," *Eur. Urol.* 35:351–354 (1999).
Small, "Advances in prostate cancer," *Curr. Opin. Oncol.* 11:226–235 (1999).
Small and Reese, "An update on prostate cancer research," *Curr. Opin. Oncol.* 12:265–272 (2000).
Xu et al., "A Novel Androgen–Regulated Gene, *PMEPA1*, Located on Chromosome 20q13 Exhibits High Level Expression in Prostate," *Genomics* 66:257–263 (2000).

* cited by examiner

```
TAGTTTGTATTTTTCATTACCAGCAAGGGTAAACAGTTATCCATGACCCATTTCTATGTTCTCGT
GGCATGCTTCCATGTACTGCCTCTGCATGCAGCAGGCCACCTCGGGCAGAGCCTAAAGCATGTGA
TAAATGAAATGCTATCACAATACAGGTTGTGTCTGAAAAACAAATGGCAACTTATTATCCAAGAT
CAATGAAGGAAAAAGCAAATTTACTAAAATATTTCTTTATTTGAATAAGGTCAATGCCATTTCTT
GAATTCCAGCTAGCATCAAATAATCAGGAAAAAAAAAACTTGACAAAATGTTATCCAATTGAAAT
TGACAGTGGATAGAAAACCCTTTTAAACTTTAAGTAATGTCATAAAAGAAATATATTAAACAAGC
AACAGACAGATCTAAAAAGTTCCAAGTGTGGATTTCACATTAGATCTTATAAATTAAAAAAATCC
TCAATATAATCATTTGTTCACTATCTTCTTTCAATAAGCACATGGACAGGGAAAGATAATCACAC
CTTAATATTCACAACTGCTATTTGTGTTCTTTACAAAAATTGTATCTCTGCAATGCAGTGAGGCA
GGCAATCCCTTGTTCAAGTCATTTCTGTTTTCCCTAAGTTATCAAAAGTACAACTGTCTGATAT
AAATTGTTACCATAATCACAATCAGGAAGGCAAAGAAGCTTTAGCAGGCAGGCTTGAAGATGGGA
GTTTTCATGGCTTGACCATGAATGATCTCAAGATGATTTCATAAGATTAAAAGCCATCACGAAAA
TACTGAAAGCAACAGGTAATAATCTGGATTCAGTCTGTAGTTGCTCATGAACCACGCGTTTTAAT
AAAAGGAACATTAAGTAAATTGTAGGTATAAAAGAATCAGTGCATATCTGTTAATGTCATTGACA
ATAAAAATATATTATCTTCTCAGCTCAGCTCTAAATTAACAAAACACCTATTTTTTTTTTCCCAC
TCCTCATTTTAGTGGTTCTCAAACATTGGTGTGCTCAGAATCTCCTGAGGT
```

FIG. 1

Sequence Range: 1 to 4527

```
            10         20         30         40         50         60
    TCCTTGGGTTCGGGTGAAAGCGCCTGGGGGTTCGTGGCCATGATCCCCGAGCTGCTGGAG
    AGGAACCCAAGCCCACTTTCGCGGACCCCCAAGCACCGGTACTAGGGGCTCGACGACCTC 70         80         90        100        110        120
    AACTGAAGGCGGACAGTCTCCTGCGAAACCAGGCAATGGCGGAGCTGGAGTTTGTTCAGA
    TTGACTTCCGCCTGTCAGAGGACGCTTTGGTCCGTTACCGCCTCGACCTCAAACAAGTCT
                                    M   A   E   L   E   F   V   Q>

130        140        150        160        170        180
    TCATCATCATCGTGGTGGTGATGATGGTGATGGTGGTGGTGATCACGTGCCTGCTGAGCC
    AGTAGTAGTAGCACCACCACTACTACCACTACCACCACCACTAGTGCACGGACGACTCGG
     I   I   I   I   V   V   V   M   M   V   M   V   V   V   I   T   C   L   L   S>

190        200        210        220        230        240
    ACTACAAGCTGTCTGCACGGTCCTTCATCAGCCGGCACAGCCAGGGGCGGAGGAGAGAAG
    TGATGTTCGACAGACGTGCCAGGAAGTAGTCGGCCGTGTCGGTCCCCGCCTCCTCTCTTC
     H   Y   K   L   S   A   R   S   F   I   S   R   H   S   Q   G   R   R   R   E>

250        260        270        280        290        300
    ATGCCCTGTCCTCAGAAGGATGCCTGTGGCCCTCGGAGAGCACAGTGTCAGGCAACGGAA
    TACGGGACAGGAGTCTTCCTACGGACACCGGGAGCCTCTCGTGTCACAGTCCGTTGCCTT
     D   A   L   S   S   E   G   C   L   W   P   S   E   S   T   V   S   G   N   G>

310        320        330        340        350        360
    TCCCAGAGCCGCAGGTCTACGCCCCGCCTCGGCCCACCGACCGCCTGGCCGTGCCGCCCT
    AGGGTCTCGGCGTCCAGATGCGGGGCGGAGCCGGGTGGCTGGCGGACCGGCACGGCGGGA
     I   P   E   P   Q   V   Y   A   P   P   R   P   T   D   R   L   A   V   P   P>

370        380        390        400        410        420
    TCGCCCAGCGGGAGCGCTTCCACCGCTTCCAGCCCACCTATCCGTACCTGCAGCACGAGA
    AGCGGGTCGCCCTCGCGAAGGTGGCGAAGGTCGGGTGGATAGGCATGGACGTCGTGCTCT
     F   A   Q   R   E   R   F   H   R   F   Q   P   T   Y   P   Y   L   Q   H   E>

430        440        450        460        470        480
    TCGACCTGCCACCCACCATCTCGCTGTCAGACGGGGAGGAGCCCCCACCCTACCAGGGCC
    AGCTGGACGGTGGGTGGTAGAGCGACAGTCTGCCCCTCCTCGGGGGTGGGATGGTCCCGG
     I   D   L   P   P   T   I   S   L   S   D   G   E   E   P   P   P   Y   Q   G>

490        500        510        520        530        540
    CCTGCACCCTCCAGCTTCGGGACCCCGAGCAGCAGCTGGAACTGAACCGGGAGTCGGTGC
    GGACGTGGGAGGTCGAAGCCCTGGGGCTCGTCGTCGACCTTGACTTGGCCCTCAGCCACG
     P   C   T   L   Q   L   R   D   P   E   Q   Q   L   E   L   N   R   E   S   V>

550        560        570        580        590        600
    GCGCACCCCCAAACAGAACCATCTTCGACAGTGACCTGATGGATAGTGCCAGGCTGGGCG
    CGCGTGGGGGTTTGTCTTGGTAGAAGCTGTCACTGGACTACCTATCACGGTCCGACCCGC
     R   A   P   P   N   R   T   I   F   D   S   D   L   M   D   S   A   R   L   G>

```
GCCCCTGCCCCCCCAGCAGTAACTCGGGCATCAGCGCCACGTGCTACGGCAGCGGCGGGC
CGGGGACGGGGGGGTCGTCATTGAGCCCGTAGTCGCGGTGCACGATGCCGTCGCCGCCCG
 G  P  C  P  P  S  S  N  S  G  I  S  A  T  C  Y  G  S  G  G>

670       680       690       700       710       720
GCATGGAGGGGCCGCCGCCCACCTACAGCGAGGTCATCGGCCACTACCCGGGGTCCTCCT
CGTACCTCCCCGGCGGCGGGTGGATGTCGCTCCAGTAGCCGGTGATGGGCCCCAGGAGGA
 R  M  E  G  P  P  P  T  Y  S  E  V  I  G  H  Y  P  G  S  S>

730       740       750       760       770       780
TCCAGCACCAGCAGAGCAGTGGGCCGCCCTCCTTGCTGGAGGGGACCCGGCTCCACCACA
AGGTCGTGGTCGTCTCGTCACCCGGCGGGAGGAACGACCTCCCCTGGGCCGAGGTGGTGT
 F  Q  H  Q  Q  S  S  G  P  P  S  L  L  E  G  T  R  L  H  H>

790       800       810       820       830       840
CACACATCGCGCCCCTAGAGAGCGCAGCCATCTGGAGCAAAGAGAAGGATAAACAGAAAG
GTGTGTAGCGCGGGGATCTCTCGCGTCGGTAGACCTCGTTTCTCTTCCTATTTGTCTTTC
 T  H  I  A  P  L  E  S  A  A  I  W  S  K  E  K  D  K  Q  K>

850       860       870       880       890       900
GACACCCTCTCTAGGGTCCCCAGGGGGGCCGGGCTGGGGCTGCGTAGGTGAAAAGGCAGA
CTGTGGGAGAGATCCCAGGGGTCCCCCCGGCCCGACCCCGACGCATCCACTTTTCCGTCT
 G  H  P  L  *>

910       920       930       940       950       960
ACACTCCGCGCTTCTTAGAAGAGGAGTGAGAGGAAGGCGGGGGGCGCAGCAACGCATCGT
TGTGAGGCGCGAAGAATCTTCTCCTCACTCTCCTTCCGCCCCCCGCGTCGTTGCGTAGCA 970       980       990      1000      1010      1020
GTGGCCCTCCCCTCCCACCTCCCTGTGTATAAATATTTACATGTGATGTCTGGTCTGAAT
CACCGGGAGGGGAGGGTGGAGGGACACATATTTATAAATGTACACTACAGACCAGACTTA 1030      1040      1050      1060      1070      1080
GCACAAGCTAAGAGAGCTTGCAAAAAAAAAAAGAAAAAAGAAAAAAAAAAACCACGTTTC
CGTGTTCGATTCTCTCGAACGTTTTTTTTTTTCTTTTTTCTTTTTTTTTTGGTGCAAAG 1090      1100      1110      1120      1130      1140
TTTGTTGAGCTGTGTCTTGAAGGCAAAAGAAAAAAAATTTCTACAGTAGTCTTTCTTGTT
AAACAACTCGACACAGAACTTCCGTTTTCTTTTTTTTAAAGATGTCATCAGAAAGAACAA 1150      1160      1170      1180      1190      1200
TCTAGTTGAGCTGCGTGCGTGAATGCTTATTTTCTTTTGTTTATGATAATTTCACTTAAC
AGATCAACTCGACGCACGCACTTACGAATAAAAGAAAACAAATACTATTAAAGTGAATTG 1210      1220      1230      1240      1250      1260
TTTAAAGACATATTTGCACAAAACCTTTGTTTAAAGATCTGCAATATTATATATATAAAT
AAATTTCTGTATAAACGTGTTTTGGAAACAAATTTCTAGACGTTATAATATATATATTTA 1270      1280      1290      1300      1310      1320
ATATATAAGATAAGAGAAACTGTATGTGCGAGGGCAGGAGTATTTTTGTATTAGAAGAGG
TATATATTCTATTCTCTTTGACATACACGCTCCCGTCCTCATAAAAACATAATCTTCTCC 1330      1340      1350      1360      1370      1380
CCTATTAAAAAAAAAAGTTGTTTTCTGAACTAGAAGAGGAAAAAAATGGCAATTTTTGAG
```

FIG. 2B

```
GGATAATTTTTTTTTTCAACAAAAGACTTGATCTTCTCCTTTTTTTACCGTTAAAAACTC 1390      1400      1410      1420      1430      1440
TGCCAAGTCAGAAAGTGTGTATTACCTTGTAAAGAAAAAAATTACAAAGCAGGGGTTTAG
ACGGTTCAGTCTTTCACACATAATGGAACATTTCTTTTTTTAATGTTTCGTCCCCAAATC 1450      1460      1470      1480      1490      1500
AGTTATTTATATAAATGTTGAGATTTTGCACTATTTTTAATATAAATATGTCAGTGCTT
TCAATAAATATATTTACAACTCTAAAACGTGATAAAAAATTATATTTATACAGTCACGAA 1510      1520      1530      1540      1550      1560
GCTTGATGGAAACTTCTCTTGTGTCTGTTGAGACTTTAAGGGAGAAATGTCGGAATTTCA
CGAACTACCTTTGAAGAGAACACAGACAACTCTGAAATTCCCTCTTTACAGCCTTAAAGT 1570      1580      1590      1600      1610      1620
GAGTCGCCTGACGGCAGAGGGTGAGCCCCCGTGGAGTCTGCAGAGAGGCCTTGGCCAGGA
CTCAGCGGACTGCCGTCTCCCACTCGGGGGCACCTCAGACGTCTCTCCGGAACCGGTCCT 1630      1640      1650      1660      1670      1680
GCGGCGGGCTTTCCCGAGGGGCCACTGTCCCTGCAGAGTGGATGCTTCTGCCTAGTGACA
CGCCGCCCGAAAGGGCTCCCCGGTGACAGGGACGTCTCACCTACGAAGACGGATCACTGT 1690      1700      1710      1720      1730      1740
GGTTATCACCACGTTATATATTCCCTACCGAAGGAGACACCTTTTCCCCCCTGACCCAGA
CCAATAGTGGTGCAATATATAAGGGATGGCTTCCTCTGTGGAAAAGGGGGGACTGGGTCT 1750      1760      1770      1780      1790      1800
ACAGCCTTTAAATCACAAGCAAAATAGGAAAGTTAACCACGGAGGCACCGAGTTCCAGGT
TGTCGGAAATTTAGTGTTCGTTTTATCCTTTCAATTGGTGCCTCCGTGGCTCAAGGTCCA 1810      1820      1830      1840      1850      1860
AGTGGTTTTGCCTTTCCCAAAAATGAAAATAAACTGTTACCGAAGGAATTAGTTTTTCCT
TCACCAAAACGGAAAGGGTTTTACTTTTATTTGACAATGGCTTCCTTAATCAAAAAGGA 1870      1880      1890      1900      1910      1920
CTTCTTTTTTCCAACTGTGAAGGTCCCCGTGGGGTGGAGCATGGTGCCCCTCACAAGCCG
GAAGAAAAAAGGTTGACACTTCCAGGGGCACCCCACCTCGTACCACGGGGAGTGTTCGGC 1930      1940      1950      1960      1970      1980
CAGCGGCTGGTGCCCGGGCTACCAGGGACATGCCAGAGGGCTCGATGACTTGTCTCTGCA
GTCGCCGACCACGGGCCCGATGGTCCCTGTACGGTCTCCCGAGCTACTGAACAGAGACGT 1990      2000      2010      2020      2030      2040
GGGCGCTTTGGTGGTTGTTCAGCTGGCTAAAGGTTCACCGGTGAAGGCAGGTGCGGTAAC
CCCGCGAAACCACCAACAAGTCGACCGATTTCCAAGTGGCCACTTCCGTCCACGCCATTG 2050      2060      2070      2080      2090      2100
TGCCGCACTGGACCCTAGGAAGCCCCAGGTATTCGCAATCTGACCTCCTCCTGTCTGTTT
ACGGCGTGACCTGGGATCCTTCGGGGTCCATAAGCGTTAGACTGGAGGAGGACAGACAAA
```

FIG. 2C

```
        2110      2120      2130      2140      2150      2160
CCCTTCACGGATCAATTCTCACTTAAGAGGCCAATAAACAACCCAACATGAAAAGGTGAC
GGGAAGTGCCTAGTTAAGAGTGAATTCTCCGGTTATTTGTTGGGTTGTACTTTTCCACTG 2170      2180      2190      2200      2210      2220
AAGCCTGGGTTTCTCCCAGGATAGGTGAAAGGGTTAAAATGAGTAAAGCAGTTGAGCAAA
TTCGGACCCAAAGAGGGTCCTATCCACTTTCCCAATTTTACTCATTTCGTCAACTCGTTT 2230      2240      2250      2260      2270      2280
CACCAACCCGAGCTTCGGGCGCAGAATTCTTCACCTTCTCTTCCCCTTTCCATCTCCTTT
GTGGTTGGGCTCGAAGCCCGCGTCTTAAGAAGTGGAAGAGAAGGGGAAAGGTAGAGGAAA 2290      2300      2310      2320      2330      2340
CCCCGCGGAAACAACGCTTCCCTTCTGGTGTGTCTGTTGATCTGTGTTTTCATTTACATC
GGGGCGCCTTTGTTGCGAAGGGAAGACCACACAGACAACTAGACACAAAAGTAAATGTAG 2350      2360      2370      2380      2390      2400
TCTCTTAGACTCCGCTCTTGTTCTCCAGGTTTTCACCAGATAGATTTGGGGTTGGCGGGA
AGAGAATCTGAGGCGAGAACAAGAGGTCCAAAAGTGGTCTATCTAAACCCCAACCGCCCT 2410      2420      2430      2440      2450      2460
CCTGCTGGTGACGTGCAGGTGAAGGACAGGAAGGGGCATGTGAGCGTAAATAGAGGTGAC
GGACGACCACTGCACGTCCACTTCCTGTCCTTCCCCGTACACTCGCATTTATCTCCACTG 2470      2480      2490      2500      2510      2520
CAGAGGAGAGCATGAGGGGTGGGGCTTTGGGACCCACCGGGGCCAGTGGCTGGAGCTTGA
GTCTCCTCTCGTACTCCCCACCCCGAAACCCTGGGTGGCCCCGGTCACCGACCTCGAACT 2530      2540      2550      2560      2570      2580
CGTCTTTCCTCCCCATGGGGGTGGGAGGGCCCCCAGCTGGAAGAGCAGACTCCCAGCTGC
GCAGAAAGGAGGGGTACCCCCACCCTCCCGGGGGTCGACCTTCTCGTCTGAGGGTCGACG 2590      2600      2610      2620      2630      2640
TACCCCCTCCCTTCCCATGGGAGTGGCTTTCCATTTTGGGCAGAATGCTGACTAGTAGAC
ATGGGGGAGGGAAGGGTACCCTCACCGAAAGGTAAAACCCGTCTTACGACTGATCATCTG 2650      2660      2670      2680      2690      2700
TAACATAAAAGATATAAAAGGCAATAACTATTGTTTGTGAGCAACTTTTTTATAACTTCC
ATTGTATTTTCTATATTTTCCGTTATTGATAACAAACACTCGTTGAAAAAATATTGAAGG 2710      2720      2730      2740      2750      2760
AAAACAAAAACCTGAGCACAGTTTTGAAGTTCTAGCCACTCGAGCTCATGCATGTGAAAC
TTTTGTTTTTGGACTCGTGTCAAAACTTCAAGATCGGTGAGCTCGAGTACGTACACTTTG 2770      2780      2790      2800      2810      2820
GTGTGCTTTACGAAGGTGGCAGCTGACAGACGTGGGCTCTGCATGCCGCCAGCCTAGTAG
CACACGAAATGCTTCCACCGTCGACTGTCTGCACCCGAGACGTACGGCGGTCGGATCATC 2830      2840      2850      2860      2870      2880
AAAGTTCTCGTTCATTGGCAACAGCAGAACCTGCCTCTCCGTGAAGTCGTCAGCCTAAAA
TTTCAAGAGCAAGTAACCGTTGTCGTCTTGGACGGAGAGGCACTTCAGCAGTCGGATTTT
```

FIG. 2D

```
        2890      2900      2910      2920      2930      2940
TTTGTTTCTCTCTTGAAGAGGATTCTTTGAAAAGGTCCTGCAGAGAAATCAGTACAGGTT
AAACAAAGAGAGAACTTCTCCTAAGAAACTTTTCCAGGACGTCTCTTTAGTCATGTCCAA 2950      2960      2970      2980      2990      3000
ATCCCGAAAGGTACAAGGACGCACTTGTAAAGATGATTAAAACGTATCTTTCCTTTATGT
TAGGGCTTTCCATGTTCCTGCGTGAACATTTCTACTAATTTTGCATAGAAAGGAAATACA 3010      3020      3030      3040      3050      3060
GACGCGTCTCTAGTGCCTTACTGAAGAAGCAGTGACACTCCCGTCGCTCGGTGAGGACGT
CTGCGCAGAGATCACGGAATGACTTCTTCGTCACTGTGAGGGCAGCGAGCCACTCCTGCA 3070      3080      3090      3100      3110      3120
TCCCGGACAGTGCCTCACTCACCTGGGACTGGTATCCCCTCCCAGGGTCCACCAAGGGCT
AGGGCCTGTCACGGAGTGAGTGGACCCTGACCATAGGGGAGGGTCCCAGGTGGTTCCCGA 3130      3140      3150      3160      3170      3180
CCTGCTTTTCAGACACCCCATCATCCTCGCGCGTCCTCACCCTGTCTCTACCAGGGAGGT
GGACGAAAAGTCTGTGGGGTAGTAGGAGCGCGCAGGAGTGGGACAGAGATGGTCCCTCCA 3190      3200      3210      3220      3230      3240
GCCTAGCTTGGTGAGGTTACTCCTGCTCCTCCAACCTTTTTTTGCCAAGGTTTGTACACG
CGGATCGAACCACTCCAATGAGGACGAGGAGGTTGGAAAAAAACGGTTCCAAACATGTGC 3250      3260      3270      3280      3290      3300
ACTCCCATCTAGGCTGAAAACCTAGAAGTGGACCTTGTGTGTGTGCATGGTGTCAGCCCA
TGAGGGTAGATCCGACTTTTGGATCTTCACCTGGAACACACACACGTACCACAGTCGGGT 3310      3320      3330      3340      3350      3360
AAGCCAGGCTGAGACAGTCCTCATATCCTCTTGAGCCAAACTGTTTGGGTCTCGTTGCTT
TTCGGTCCGACTCTGTCAGGAGTATAGGAGAACTCGGTTTGACAAACCCAGAGCAACGAA 3370      3380      3390      3400      3410      3420
CATGGTATGGTCTGGATTTGTGGGAATGGCTTTGCGTGAGAAAGGGGAGGAGAGTGGTTG
GTACCATACCAGACCTAAACACCCTTACCGAAACGCACTCTTTCCCCTCCTCTCACCAAC 3430      3440      3450      3460      3470      3480
CTGCCCTCAGCCGGCTTGAGGACAGAGCCTGTCCCTCTCATGACAACTCAGTGTTGAAGC
GACGGGAGTCGGCCGAACTCCTGTCTCGGACAGGGAGAGTACTGTTGAGTCACAACTTCG 3490      3500      3510      3520      3530      3540
CCAGTGTCCTCAGCTTCATGTCCAGTGGATGGCAGAAGTTCATGGGGTAGTGGCCTCTCA
GGTCACAGGAGTCGAAGTACAGGTCACCTACCGTCTTCAAGTACCCCATCACCGGAGAGT 3550      3560      3570      3580      3590      3600
AAGGCTGGGCGCATCCCAAGACAGCCAGCAGGTTGTCTCTGGAAACGACCAGAGTTAAGC
TTCCGACCCGCGTAGGGTTCTGTCGGTCGTCCAACAGAGACCTTTGCTGGTCTCAATTCG 3610      3620      3630      3640      3650      3660
TCTCGGCTTCTCTGCTGAGGGTGCACCCTTTCCTCTAGATGGTAGTTGTCACGTTATCTT
AGAGCCGAAGAGACGACTCCCACGTGGGAAAGGAGATCTACCATCAACAGTGCAATAGAA
```

FIG. 2E

```
          3670      3680      3690      3700      3710      3720
TGAAAACTCTTGGACTGCTCCTGAGGAGGCCCTCTTTTCCAGTAGGAAGTTAGATGGGGG
ACTTTTGAGAACCTGACGAGGACTCCTCCGGGAGAAAAGGTCATCCTTCAATCTACCCCC 3730      3740      3750      3760      3770      3780
TTCTCAGAAGTGGCTGATTGGAAGGGGACAAGCTTCGTTTCAGGGGTCTGCCGTTCCATC
AAGAGTCTTCACCGACTAACCTTCCCCTGTTCGAAGCAAAGTCCCCAGACGGCAAGGTAG 3790      3800      3810      3820      3830      3840
CTGGTTCAGAGAAGGCCGAGCGTGGCTTTCTCTAGCCTTGTCACTGTCTCCCTGCCTGTC
GACCAAGTCTCTTCCGGCTCGCACCGAAAGAGATCGGAACAGTGACAGAGGGACGGACAG 3850      3860      3870      3880      3890      3900
AATCACCACCTTTCCYCCAGAGGAGGAAAATTATCTCCCCTGCAAAGCCCGGTTCTACAC
TTAGTGGTGGAAAGGRGGTCTCCTCCTTTTAATAGAGGGGACGTTTCGGGCCAAGATGTG 3910      3920      3930      3940      3950      3960
AGATTTCACAAATTGTGCTAAGAACCGTCCGTGTTCTCAGAAAGCCCAGTGTTTTTGCAA
TCTAAAGTGTTTAACACGATTCTTGGCAGGCACAAGAGTCTTTCGGGTCACAAAAACGTT 3970      3980      3990      4000      4010      4020
AGAATGAAAAGGGACCCCATATGTAGCAAAAATCAGGGCTGGGGAGAGCCGGGTTCATT
TCTTACTTTTCCCTGGGGTATACATCGTTTTTAGTCCCGACCCCCTCTCGGCCCAAGTAA 4030      4040      4050      4060      4070      4080
CCCTGTCCTCATTGGTCGTCCCTATGAATTGTACGTTTCAGAGAAATTTTTTTTCCTATG
GGGACAGGAGTAACCAGCAGGGATACTTAACATGCAAAGTCTCTTTAAAAAAAAGGATAC 4090      4100      4110      4120      4130      4140
TGCAACACGAAGCTTCCAGAACCATAAAATATCCCGTCGATAAGGAAAGAAAATGTCGTT
ACGTTGTGCTTCGAAGGTCTTGGTATTTTATAGGGCAGCTATTCCTTTCTTTTACAGCAA 4150      4160      4170      4180      4190      4200
GTTGTTGTTTTTCTGGAAACTGCTTGAAATCTTGCTGTACTATAGAGCTCAGAAGGACAC
CAACAACAAAAAGACCTTTGACGAACTTTAGAACGACATGATATCTCGAGTCTTCCTGTG 4210      4220      4230      4240      4250      4260
AGCCCGTCCTCCCCTGCCTGCCTGATTCCATGGCTGTTGTGCTGATTCCAATGCTTTCAC
TCGGGCAGGAGGGGACGGACGGACTAAGGTACCGACAACACGACTAAGGTTACGAAAGTG 4270      4280      4290      4300      4310      4320
GTTGGTTCCTGGCGTGGGAACTGCTCTCCTTTGCAGCCCCATTTCCCAAGCTCTGTTCAA
CAACCAAGGACCGCACCCTTGACGAGAGGAAACGTCGGGGTAAAGGGTTCGAGACAAGTT 4330      4340      4350      4360      4370      4380
GTTAAACTTATGTAAGCTTTCCGTGGCATGCGGGGCGCGCACCCACGTCCCCGCTGCGTA
CAATTTGAATACATTCGAAAGGCACCGTACGCCCCGCGCGTGGGTGCAGGGGCGACGCAT 4390      4400      4410      4420      4430      4440
AGACTCTGTATTTGGATGCCAATCCACAGGCCTGAAGAAACTGCTTGTTGTGTATCAGTA
TCTGAGACATAAACCTACGGTTAGGTGTCCGGACTTCTTTGACGAACAACACATAGTCAT
```

FIG. 2F

```
         4450      4460      4470      4480      4490      4500
ATCATTAGTGGCAATGATGACATTCTGAAAAGCTGCAATACTTATACAATAAATTTTACA
TAGTAATCACCGTTACTACTGTAAGACTTTTCGACGTTATGAATATGTTATTTAAAATGT 4510      4520
ATTCTTTGGAAAAAAAAAAAAAAAAA
TAAGAAACCTTTTTTTTTTTTTTTTT
```

FIG. 2G

Sequence Range: 1 to 2213

```
         10        20        30        40        50        60
GGGGGGCTGACAACAACTGTGATAGGTACGAGGCTGGGTGTGGATCGGCCGAGGCTCTCC
CCCCCCGACTGTTGTTGACACTATCCATGCTCCGACCCACACCTAGCCGGCTCCGAGAGG
 G  G  L  T  T  T  V  I  G  T  R  L  G  V  D  R  P  R  L  S>

70        80        90       100       110       120
TGGAGCGCTGGGCCTTCGCTGGCCGCACCGGCAGCCATGAGCTCGGAGATGGAGCCGCTG
ACCTCGCGACCCGGAAGCGACCGGCGTGGCCGTCGGTACTCGAGCCTCTACCTCGGCGAC
 W  S  A  G  P  S  L  A  A  P  A  A  M  S  S  E  M  E  P  L>

130       140       150       160       170       180
CTCCTGGCCTGGAGCTATTTTAGGCGCAGGAAGTTCCAGCTCTGCGCCGATCTATGCACG
GAGGACCGGACCTCGATAAAATCCGCGTCCTTCAAGGTCGAGACGCGGCTAGATACGTGC
 L  L  A  W  S  Y  F  R  R  R  K  F  Q  L  C  A  D  L  C  T>

190       200       210       220       230       240
CAGATGCTGGAGAAGTCCCCTTATGACCAGGCAGCTTGGATCTTAAAAGCAAGAGCGCTA
GTCTACGACCTCTTCAGGGGAATACTGGTCCGTCGAACCTAGAATTTTCGTTCTCGCGAT
 Q  M  L  E  K  S  P  Y  D  Q  A  A  W  I  L  K  A  R  A  L>

250       260       270       280       290       300
ACAGAAATGGTATACATAGATGAAATTGATGTAGATCAGGAAGGAATTGCAGAAATGATG
TGTCTTTACCATATGTATCTACTTTAACTACATCTAGTCCTTCCTTAACGTCTTTACTAC
 T  E  M  V  Y  I  D  E  I  D  V  D  Q  E  G  I  A  E  M  M>

310       320       330       340       350       360
CTGGATGAAAATGCTATAGCTCAAGTTCCACGCCCTGGAACGTCTTTGAAACTCCCTGGA
GACCTACTTTTACGATATCGAGTTCAAGGTGCGGGACCTTGCAGAAACTTTGAGGGACCT
 L  D  E  N  A  I  A  Q  V  P  R  P  G  T  S  L  K  L  P  G>

370       380       390       400       410       420
ACTAATCAGACAGGAGGGCCTAGCCAGGCCGTTAGGCCAATCACACAAGCTGGAAGACCC
TGATTAGTCTGTCCTCCCGGATCGGTCCGGCAATCCGGTTAGTGTGTTCGACCTTCTGGG
 T  N  Q  T  G  G  P  S  Q  A  V  R  P  I  T  Q  A  G  R  P>

430       440       450       460       470       480
ATTACAGGTTTCCTCAGGCCCAGCACGCAGAGTGGAAGGCCAGGCACTATGGAACAGGCT
TAATGTCCAAAGGAGTCCGGGTCGTGCGTCTCACCTTCCGGTCCGTGATACCTTGTCCGA
 I  T  G  F  L  R  P  S  T  Q  S  G  R  P  G  T  M  E  Q  A>

490       500       510       520       530       540
ATCAGAACACCCAGAACCGCCTACACAGCCCGCCCTATCACCAGCTCCTCCGGAAGATTT
TAGTCTTGTGGGTCTTGGCGGATGTGTCGGGCGGGATAGTGGTCGAGGAGGCCTTCTAAA
 I  R  T  P  R  T  A  Y  T  A  R  P  I  T  S  S  S  G  R  F>

550       560       570       580       590       600
GTCAGGCTGGGAACGGCTTCCATGCTTACAAGTCCTGATGGACCATTTATAAATTTATCT
CAGTCCGACCCTTGCCGAAGGTACGAATGTTCAGGACTACCTGGTAAATATTTAAATAGA
 V  R  L  G  T  A  S  M  L  T  S  P  D  G  P  F  I  N  L  S>

```
AGGCTGAATTTAACAAAGTATTCCCAGAAACCTAAGTTGGCAAAGGCTTGTTTGAGTATA
TCCGACTTAAATTGTTTCATAAGGGTCTTTGGATTCAACCGTTTCCGAACAAACTCATAT
  R  L  N  L  T  K  Y  S  Q  K  P  K  L  A  K  A  C  L  S  I>

670       680       690       700       710       720
TCTTTCATCATGAAAATGATGTTAAGACTGCTTTGGATCTGGCTGGCCCTCTCCACAGAA
AGAAAGTAGTACTTTTACTACAATTCTGACGAAACCTAGACCGACCGGGAGAGGTGTCTT
  S  F  I  M  K  M  M  L  R  L  L  W  I  W  L  A  L  S  T  E>

730       740       750       760       770       780
CATTCTCAGTACAAGGACTGGTGGTGGAAAGTACAGATTGGAAAATGTTACTACAGGTTG
GTAAGAGTCATGTTCCTGACCACCACCTTTCATGTCTAACCTTTTACAATGATGTCCAAC
  H  S  Q  Y  K  D  W  W  W  K  V  Q  I  G  K  C  Y  Y  R  L>

790       800       810       820       830       840
GGAATGTATCGTGAAGCAGAAAAACAGTTTAAATCAGCCCTGAAGCAGCAGGAAATGGTA
CCTTACATAGCACTTCGTCTTTTTGTCAAATTTAGTCGGGACTTCGTCGTCCTTTACCAT
  G  M  Y  R  E  A  E  K  Q  F  K  S  A  L  K  Q  Q  E  M  V>

850       860       870       880       890       900
GATACATTTCTGTACTTGGCAAAAGTTTATGTCTCATTGGATCAACCTGTGACTGCTTTA
CTATGTAAAGACATGAACCGTTTTCAAATACAGAGTAACCTAGTTGGACACTGACGAAAT
  D  T  F  L  Y  L  A  K  V  Y  V  S  L  D  Q  P  V  T  A  L>

910       920       930       940       950       960
AATCTTTTCAAACAAGGCTTAGATAAGTTTCCAGGAGAAGTAACCCTGCTCTGTGGAATT
TTAGAAAAGTTTGTTCCGAATCTATTCAAAGGTCCTCTTCATTGGGACGAGACACCTTAA
  N  L  F  K  Q  G  L  D  K  F  P  G  E  V  T  L  L  C  G  I>

970       980       990      1000      1010      1020
GCAAGAATCTATGAGGAAATGAACAATATGTCATCAGCAGCAGAATATTACAAAGAAGTT
CGTTCTTAGATACTCCTTTACTTGTTATACAGTAGTCGTCGTCTTATAATGTTTCTTCAA
  A  R  I  Y  E  E  M  N  N  M  S  S  A  A  E  Y  Y  K  E  V>

1030      1040      1050      1060      1070      1080
TTGAAACAAGACAATACTCATGTGGRAGCCATCGCATGCATTGGAAGCAACCACTTCTAT
AACTTTGTTCTGTTATGAGTACACCYTCGGTAGCGTACGTAACCTTCGTTGGTGAAGATA
  L  K  Q  D  N  T  H  V  X  A  I  A  C  I  G  S  N  H  F  Y>

1090      1100      1110      1120      1130      1140
TCTGATCAGCCAGAAATAGCTCTCCGGTTTTACAGGCGGCTGCTGCAGATGGGCATTTAT
AGACTAGTCGGTCTTTATCGAGAGGCCAAAATGTCCGCCGACGACGTCTACCCGTAAATA
  S  D  Q  P  E  I  A  L  R  F  Y  R  R  L  L  Q  M  G  I  Y>

1150      1160      1170      1180      1190      1200
AACGGCCAGCTTTTTAACAATCTGGGGCTGTGTTGCTTCTATGCCCAGCAGTATGATATG
TTGCCGGTCGAAAAATTGTTAGACCCCGACACAACGAAGATACGGGTCGTCATACTATAC
  N  G  Q  L  F  N  N  L  G  L  C  C  F  Y  A  Q  Q  Y  D  M>

1210      1220      1230      1240      1250      1260
ACTCTGACCTCATTTGAACGTGCCCTTTCTTTGGCTGAAAATGAAGAAGAGGCAGCTGAT
TGAGACTGGAGTAAACTTGCACGGGAAAGAAACCGACTTTTACTTCTTCTCCGTCGACTA
  T  L  T  S  F  E  R  A  L  S  L  A  E  N  E  E  E  A  A  D>
```

FIG. 3B

```
      1270      1280      1290      1300      1310      1320
GTCTGGTACAACTTGGGACATGTAGCTGTGGGAATAGGAGATACAAATTTGGCCCATCAG
CAGACCATGTTGAACCCTGTACATCGACACCCTTATCCTCTATGTTTAAACCGGGTAGTC
  V  W  Y  N  L  G  H  V  A  V  G  I  G  D  T  N  L  A  H  Q>

1330      1340      1350      1360      1370      1380
TGCTTCAGGCTGGCTCTGGTCAACAACAACAACCACGCCGAGGCCTACAACAACCTGGCT
ACGAAGTCCGACCGAGACCAGTTGTTGTTGTTGGTGCGGCTCCGGATGTTGTTGGACCGA
  C  F  R  L  A  L  V  N  N  N  N  H  A  E  A  Y  N  N  L  A>

1390      1400      1410      1420      1430      1440
GTGCTGGAGATGCGGAAGGGCCACGTTGAACAGGCAAGGGCACTATTACAAACTGCATCA
CACGACCTCTACGCCTTCCCGGTGCAACTTGTCCGTTCCCGTGATAATGTTTGACGTAGT
  V  L  E  M  R  K  G  H  V  E  Q  A  R  A  L  L  Q  T  A  S>

1450      1460      1470      1480      1490      1500
TCATTAGCACCCCATATGTATGAACCGCATTTTAATTTTGCAACAATCTCTGATAAGATT
AGTAATCGTGGGGTATACATACTTGGCGTAAAATTAAAACGTTGTTAGAGACTATTCTAA
  S  L  A  P  H  M  Y  E  P  H  F  N  F  A  T  I  S  D  K  I>

1510      1520      1530      1540      1550      1560
GGAGATCTGCAGAGAAGCTATGTTGCTGCGCAGAAGTCTGAAGCAGCATTTCCAGACCAT
CCTCTAGACGTCTCTTCGATACAACGACGCGTCTTCAGACTTCGTCGTAAAGGTCTGGTA
  G  D  L  Q  R  S  Y  V  A  A  Q  K  S  E  A  A  F  P  D  H>

1570      1580      1590      1600      1610      1620
GTGGACACACAACATTTAATTAAACAATTAAGGCAGCATTTTGCTATGCTCTGATTGTTC
CACCTGTGTGTTGTAAATTAATTTGTTAATTCCGTCGTAAAACGATACGAGACTAACAAG
  V  D  T  Q  H  L  I  K  Q  L  R  Q  H  F  A  M  L>

1630      1640      1650      1660      1670      1680
CTTAGACCACATATGTTCTTATGAAGCAGCATTATGCAAGGGGAAAAAAGCACTATGTCT
GAATCTGGTGTATACAAGAATACTTCGTCGTAATACGTTCCCCTTTTTTCGTGATACAGA 1690      1700      1710      1720      1730      1740
GTGTATGTATGTATATAGTGTAATACGTATATTTTAACAAACCTGTCCTTGATATTAGTT
CACATACATACATATATCACATTATGCATATAAAATTGTTTGGACAGGAACTATAATCAA 1750      1760      1770      1780      1790      1800
AAGGTGACACATAAGGGTGACACAGAATGTGTAATGCAAATTTCATAGTAATAGTAACTT
TTCCACTGTGTATTCCCACTGTGTCTTACACATTACGTTTAAAGTATCATTATCATTGAA 1810      1820      1830      1840      1850      1860
TATAAAATAATATTATAAAATACAGGATTTAAACCTTTCTAAATAGATCCTGAAACTGTC
ATATTTTATTATAATATTTTATGTCCTAAATTTGGAAAGATTTATCTAGGACTTTGACAG 1870      1880      1890      1900      1910      1920
TCTCACATTATATAGTAGATGTTTGTTTATAATGTTTACAAAACATTTTGGTGAATTTCC
AGAGTGTAATATATCATCTACAAACAAATATTACAAATGTTTTGTAAAACCACTTAAAGG 1930      1940      1950      1960      1970      1980
TCAATGTTTTATAAATGTACATTTTTTAAGTCCTTAAGCTGACTCTTAGCCATCATGTAG
AGTTACAAAATATTTACATGTAAAAAATTCAGGAATTCGACTGAGAATCGGTAGTACATC
```

FIG. 3C

```
         1990      2000      2010      2020      2030      2040
CTTAAGGAGTCTGAAATCTGCCATTAAAACTGCACCTTTAAGCCAGGTGTGGTAGCATGT
GAATTCCTCAGACTTTAGACGGTAATTTTGACGTGGAAATTCGGTCCACACCATCGTACA 2050      2060      2070      2080      2090      2100
GCCTATAGTCCCAGCTACTTGGGAGGTGGAGGTGGGAGGATTATAAATAGAGACTTTCCT
CGGATATCAGGGTCGATGAACCCTCCACCTCCACCCTCCTAATATTTATCTCTGAAAGGA 2110      2120      2130      2140      2150      2160
TAAGACTTTAAAAATGTATTTAAAACTATTTTTTATTAAATACTTTGTGATTTCCTATTA
ATTCTGAAATTTTACATAAATTTTGATAAAAAATAATTTATGAAACACTAAAGGATAAT 2170      2180      2190      2200      2210
AGCTTTAAAATAAATCATTGTGTAAAACACCATCAAAGCGATAAGCTCTGTAA
TCGAAATTTTATTTAGTAACACATTTTGTGGTAGTTTCGCTATTCGAGACATT
```

FIG. 3D

Sequence Range: 1 to 4433

```
          10        20        30        40        50        60
ATAGGAGTGGAGAACATGCACAATTACTGCTTTGTGTTTGCTCTGGGATACCTCACAGTG
TATCCTCACCTCTTGTACGTGTTAATGACGAAACACAAACGAGACCCTATGGAGTGTCAC
   I  G  V  E  N  M  H  N  Y  C  F  V  F  A  L  G  Y  L  T  V>

70        80        90       100       110       120
TGCCAAGTTACTCGAGTCTATATCTTTGACTATGGACAATATTCTGCTGATTTTTCAGGC
ACGGTTCAATGAGCTCAGATATAGAAACTGATACCTGTTATAAGACGACTAAAAAGTCCG
   C  Q  V  T  R  V  Y  I  F  D  Y  G  Q  Y  S  A  D  F  S  G>

130       140       150       160       170       180
CCAATGATGATCATTACTCAGAAGATCACTAGTTTGGCTTGCGAAATACATGATGGGATG
GGTTACTACTAGTAATGAGTCTTCTAGTGATCAAACCGAACGCTTTATGTACTACCCTAC
   P  M  M  I  I  T  Q  K  I  T  S  L  A  C  E  I  H  D  G  M>

190       200       210       220       230       240
TTTCGGAAGGATGAAGAACTGACTTCCTCACAGAGGGATTTAGCTGTAAGGCGCATGCCA
AAAGCCTTCCTACTTCTTGACTGAAGGAGTGTCTCCCTAAATCGACATTCCGCGTACGGT
   F  R  K  D  E  E  L  T  S  S  Q  R  D  L  A  V  R  R  M  P>

250       260       270       280       290       300
AGCTTACTGGAGTATTTGAGTTACAACTGTAACTTCATGGGGATCCTGGCAGGCCCACTT
TCGAATGACCTCATAAACTCAATGTTGACATTGAAGTACCCCTAGGACCGTCCGGGTGAA
   S  L  L  E  Y  L  S  Y  N  C  N  F  M  G  I  L  A  G  P  L>

310       320       330       340       350       360
TGCTCTTACAAAGACTACATTACTTTCATTGAAGGCAGATCATACCATATCACACAATCT
ACGAGAATGTTTCTGATGTAATGAAAGTAACTTCCGTCTAGTATGGTATAGTGTGTTAGA
   C  S  Y  K  D  Y  I  T  F  I  E  G  R  S  Y  H  I  T  Q  S>

370       380       390       400       410       420
GGTGAAAATGGAAAAGAAGAGACACAGTATGAAAGAACAGAGCCATCTCCAAATGTAAGG
CCACTTTTACCTTTTCTTCTCTGTGTCATACTTTCTTGTCTCGGTAGAGGTTTACATTCC
   G  E  N  G  K  E  E  T  Q  Y  E  R  T  E  P  S  P  N  V  R>

430       440       450       460       470       480
TCATGAGATTTATCTGGAGCCTTTACAGCATGTATTGACTGCGGKTGTTCAGAAGCTCTT
AGTACTCTAAATAGACCTCGGAAATGTCGTACATAACTGACGCCMACAAGTCTTCGAGAA
   S>

490       500       510       520       530       540
AGTTTGTGGGCTGTCCTTGTTATTTCACTTGACCATCTGTACAACATTACCTGTGGAGTA
TCAAACACCCGACAGGAACAATAAAGTGAACTGGTAGACATGTTGTAATGGACACCTCAT 550       560       570       580       590       600
CAACATTGATGAGCATTTTCAAGCTACAGCTTCGTGGCCAACAAAGATTATCTATCTGTA
GTTGTAACTACTCGTAAAAGTTCGATGTCGAAGCACCGGTTGTTTCTAATAGATAGACAT
```

FIG. 4A

```
       610        620        630        640        650        660
TATCTCTCTTTTGGCTGCCAGACCCAAATACTATTTTGCATGGACGCTAGCTGACTGCCA
ATAGAGAGAAAACCGACGGTCTGGGTTTATGATAAAACGTACCTGCGATCGACTGACGGT 670        680        690        700        710        720
TWAATAATGCTGCAGGCTTTGGTTTCAGAGGGTATGACGAAAATGGAGCAGCTCGCTGGG
AWTTATTACGACGTCCGAAACCAAAGTCTCCCATACTGCTTTTACCTCGTCGAGCGACCC 730        740        750        760        770        780
ACTTAATTTCCAATTTGAGAATTCAACAAATAGAGATGTCAACAAGTTTCAAGATGTTTC
TGAATTAAAGGTTAAACTCTTAAGTTGTTTATCTCTACAGTTGTTCAAAGTTCTACAAAG 790        800        810        820        830        840
TTGATAATTGGAATATTCAGACAGCTCTTTGGCTCAAAAGGTGCGTTCCTTCAAAAACGA
AACTATTAACCTTATAAGTCTGTCGAGAAACCGAGTTTTCCACGCAAGGAAGTTTTTGCT 850        860        870        880        890        900
TCTTTAGATGTGCTTTGGCGTCTAGTTCTCGAGGTTGAGCTTCATTGAGTTCAGGTTCTT
AGAAATCTACACGAAACCGCAGATCAAGAGCTCCAACTCGAAGTAACTCAAGTCCAAGAA 910        920        930        940        950        960
GATTAAATTAACGGTGTTGAGTGACATTGTGACCTCAGTGTCAGCCGGGAAACACTGTTA
CTAATTTAATTGCCACAACTCACTGTAACACTGGAGTCACAGTCGGCCCTTTGTGACAAT 970        980        990       1000       1010       1020
GCCTCCTCCTAAGCAAGTCAGTATCGAATGAGAACTATTTTGGCTTGAGTCACGAATGCA
CGGAGGAGGATTCGTTCAGTCATAGCTTACTCTTGATAAAACCGAACTCAGTGCTTACGT 1030       1040       1050       1060       1070       1080
GCTATCCTGCAGGTGCAGCTATCCTGCCCTCTCAAGCCTCCTTTAAAGGCCTCTGCCAAT
CGATAGGACGTCCACGTCGATAGGACGGGAGAGTTCGGAGGAAATTTCCGGAGACGGTTA 1090       1100       1110       1120       1130       1140
GTCAGAGGTCACCAGTATCCTCCTTTGCAGCTCCTGATTGTGTTCAGTAGAGATGTGGTT
CAGTCTCCAGTGGTCATAGGAGGAAACGTCGAGGACTAACACAAGTCATCTCTACACCAA 1150       1160       1170       1180       1190       1200
TAAATTAACAAGTGCCTGCACAAGCACAGTACTTATGCCTGGGTACTCCAGAACAGTCCT
ATTTAATTGTTCACGGACGTGTTCGTGTCATGAATACGGACCCATGAGGTCTTGTCAGGA 1210       1220       1230       1240       1250       1260
GGTTTTAAATATTTCAATTCAACAAATCTTKATTTGTTAGGCAAGGGAAACAAACATGAG
CCAAAATTTATAAAGTTAAGTTGTTTAGAAMTAAACAATCCGTTCCCTTTGTTTGTACTC 1270       1280       1290       1300       1310       1320
TAAGATAAAAAGACTCAGCTCCTGAAAGTGAAAGAGTTCACAATTTTATTAAAGACACGG
ATTCTATTTTTCTGAGTCGAGGACTTTCACTTTCTCAAGTGTTAAAATAATTTCTGTGCC 1330       1340       1350       1360       1370       1380
TGGTGTAATCAGACACATGCTGTTCCCTGTGGTGAGGATGAGGAGAGAGAAAGCAGGAAC
ACCACATTAGTCTGTGTACGACAAGGGACACCACTCCTACTCCTCTCTCTTTCGTCCTTG
```

FIG. 4B

```
              1390      1400      1410      1420      1430      1440
        AGCGAGGGCACAGAGGGATGCGGGAAGAACTTCCTACAAGTGTGGGTGCTTGAGCTGAGG
        TCGCTCCCGTGTCTCCCTACGCCCTTCTTGAAGGATGTTCACACCCACGAACTCGACTCC 1450      1460      1470      1480      1490      1500
        TTTGTGTCAGGAGCGTGTCTCGTGAACAGGGCAAGGTAGAGGCAAGCCAGGCTGGGTGGA
        AAACACAGTCCTCGCACAGAGCACTTGTCCCGTTCCATCTCCGTTCGGTCCGACCCACCT 1510      1520      1530      1540      1550      1560
        GTAACAGGTGCGAAGGACAGAGCTGGGGAACAGCACACTCTCCCAGGGGTTCTCTTATCG
        CATTGTCCACGCTTCCTGTCTCGACCCCTTGTCGTGTGAGAGGGTCCCCAAGAGAATAGC 1570      1580      1590      1600      1610      1620
        TCCCTGTGAGCACATTGCCCTATCTTGAATTTACTTCATAAAAAACGGCCCCTATAACGA
        AGGGACACTCGTGTAACGGGATAGAACTTAAATGAAGTATTTTTTGCCGGGGATATTGCT 1630      1640      1650      1660      1670      1680
        TACGGTGATAAGCAGCCTTTTTTTATAGTGTCCTTTTTTAAATGACAAATTAAACATCTT
        ATGCCACTATTCGTCGGAAAAAAATATCACAGGAAAAAATTTACTGTTTAATTTGTAGAA 1690      1700      1710      1720      1730      1740
        TATCCCTTGAGATGGCTAGCATACGCTGTCATCTCTTCACAGTGCCTGGCAGTCTCCCCA
        ATAGGGAACTCTACCGATCGTATGCGACAGTAGAGAAGTGTCACGGACCGTCAGAGGGGT 1750      1760      1770      1780      1790      1800
        GTGGCTGCAGATCCTCTGAGCTAATCTGTTGTGTTATTTTTGTTATTGTTATAATTTAA
        CACCGACGTCTAGGAGACTCGATTAGACAACACAATAAAAAACAATAACAATATTAAATT 1810      1820      1830      1840      1850      1860
        ATTTGATACCTTAGGGGAAACTTTATTTTCAGCTGAGTTCTCTATCCCTGTCATAGAAGA
        TAAACTATGGAATCCCCTTTGAAATAAAAGTCGACTCAAGAGATAGGGACAGTATCTTCT 1870      1880      1890      1900      1910      1920
        ATTGTAGACTAAGCACAGTCTATCTGCCGGAAGGAGTAGTGTTATTAGGTCAGTTGAAAG
        TAACATCTGATTCGTGTCAGATAGACGGCCTTCCTCATCACAATAATCCAGTCAACTTTC 1930      1940      1950      1960      1970      1980
        TTATTGATTTTTTTTAAATAAATAATGTAGGATAAAAGCAACCTTACTCTTTTTGTAAA
        AATAACTAAAAAAAATTTATTTTATTACATCCTATTTTCGTTGGAATGAGAAAAACATTT 1990      2000      2010      2020      2030      2040
        TTGTATAGACTCCCAAATACTAGAAATGATCATTTAAGTTACTATATATACCAATATATA
        AACATATCTGAGGGTTTATGATCTTTACTAGTAAATTCAATGATATATATGGTTATATAT 2050      2060      2070      2080      2090      2100
        TACTATATATACCAATAAGAAGATGAGAATTAACTTTATGTTCCTAAATTTGACACTTAA
        ATGATATATATGGTTATTCTTCTACTCTTAATTGAAATACAAGGATTTAAACTGTGAATT 2110      2120      2130      2140      2150      2160
        TAGCTATAGCCTCCCTGAGATCATAGAGAAGTGATTGCCTAAGATAAGTTGTATTTGTTT
        ATCGATATCGGAGGGACTCTAGTATCTCTTCACTAACGGATTCTATTCAACATAAACAAA
```

FIG. 4C

```
         2170       2180       2190       2200       2210       2220
TTCTAGTTACCCTAAATCCTGTCAGGTAATAAAAGAATGATCATTGCAGGCTTTGTAAAC
AAGATCAATGGGATTTAGGACAGTCCATTATTTTCTTACTAGTAACGTCCGAAACATTTG 2230       2240       2250       2260       2270       2280
TCGGGTCACTCACTCCACTTGGCTCTCCATGTTTTTCATGGTTTCTAGGGTGTGTTATGA
AGCCCAGTGAGTGAGGTGAACCGAGAGGTACAAAAAGTACCAAAGATCCCACACAATACT 2290       2300       2310       2320       2330       2340
ACGAACCTCCTTCAGTCCAACTATCCAGACGTTCATTCTCTCTGCCATTTGGCACGGGGT
TGCTTGGAGGAAGTCAGGTTGATAGGTCTGCAAGTAAGAGAGACGGTAAACCGTGCCCCA 2350       2360       2370       2380       2390       2400
ATACCCAGGATATTATCTAACGTTTCTAACAGGGGTGTTAATGACATTAGCAGCAAGAGC
TATGGGTCCTATAATAGATTGCAAAGATTGTCCCCACAATTACTGTAATCGTCGTTCTCG 2410       2420       2430       2440       2450       2460
TGTAAGTATCAAGAATTTTATTTTACAATTCAATGGTCCACTTGAACTGTTAAAAAGGCT
ACATTCATAGTTCTTAAAATAAAATGTTAAGTTACCAGGTGAACTTGACAATTTTTCCGA 2470       2480       2490       2500       2510       2520
GAGTACATCTCTCTTACAAGGTAGACCCTCTTTCCTTGGTCGTGGTCAGTATTGTCCTTT
CTCATGTAGAGAGAATGTTCCATCTGGGAGAAAGGAACCAGCACCAGTCATAACAGGAAA 2530       2540       2550       2560       2570       2580
CCACTAGAAGCGAGGTGTGTACTGCGTGCATGTTTGCTGAGCGCTCACCACGGGCTAGGC
GGTGATCTTCGCTCCACACATGACGCACGTACAAACGACTCGCGAGTGGTGCCCGATCCG 2590       2600       2610       2620       2630       2640
TCCATGCCCAGTTCCTGTGAGGAGAAAACACGTTTCTATGTGCCCGGCAGGTAGGAGGCA
AGGTACGGGTCAAGGACACTCCTCTTTTGTGCAAAGATACACGGGCCGTCCATCCTCCGT 2650       2660       2670       2680       2690       2700
CTCACAAAATGTTACTTTGTCTTTACAGAATTTTCTGAAGGAGAGATAAAAACTGAGTTA
GAGTGTTTTACAATGAAACAGAAATGTCTTAAAAGACTTCCTCTCTATTTTTGACTCAAT 2710       2720       2730       2740       2750       2760
AATAAAGATGATCAGAATGGATGAGAAATAACTTTAGACATTATTTCATTGAACCTTCCC
TTATTTCTACTAGTCTTACCTACTCTTTATTGAAATCTGTAATAAAGTAACTTGGAAGGG 2770       2780       2790       2800       2810       2820
AACTGAAATTATTTTATGATGTTATAACATGGATAGTAACTCAAGTAGCAATAAGTTACA
TTGACTTTAATAAAATACTACAATATTGTACCTATCATTGAGTTCATCGTTATTCAATGT 2830       2840       2850       2860       2870       2880
CAGTTGTGCCATTTGTGCTTCTTTCTATAAAACCATCACTCACGTTTTACAGCTCCTGGT
GTCAACACGGTAAACACGAAGAAGATATTTTGGTAGTGAGTGCAAAATGTCGAGGACCA 2890       2900       2910       2920       2930       2940
ATTATTGCCTGCACATTCTTGGTATCTTAGTATTATTGTTGTTGCCAGTGAAAAAAACTC
TAATAACGGACGTGTAAGAACCATAGAATCATAATAACAACAACGGTCACTTTTTTTGAG
```

FIG. 4D

```
         2950       2960       2970       2980       2990       3000
AAAGAAGAAAGAATACACATGAAAACATTCAGCTCTCACAATCCAAAAAGTTTGATGAAG
TTTCTTCTTTCTTATGTGTACTTTTGTAAGTCGAGAGTGTTAGGTTTTTCAAACTACTTC 3010       3020       3030       3040       3050       3060
GAGAAAATTCTTTGGGACAGAACAGTTTTTCTACAACAAACAATGTTTGCAATCAGAATC
CTCTTTTAAGAAACCCTGTCTTGTCAAAAGATGTTGTTTGTTACAAACGTTAGTCTTAG 3070       3080       3090       3100       3110       3120
AAGAAATAGCCTCGAGACATTCATCACTAAAGCAGTGATCGGGAAGGCTCTGAGGGCTGT
TTCTTTATCGGAGCTCTGTAAGTAGTGATTTCGTCACTAGCCCTTCCGAGACTCCCGACA 3130       3140       3150       3160       3170       3180
TTTTTTTTTTTGATGTTAACAGAAACCAATCTTAGCACCTTTTCAAGGGGTTTGAGTTTG
AAAAAAAAAAAACTACAATTGTCTTTGGTTAGAATCGTGGAAAAGTTCCCCAAACTCAAAC 3190       3200       3210       3220       3230       3240
TTGGAAAAGCAGTTAACTGGGGGGAAATGGACAGTTATAGATAAGGAATTTCCTGTACAC
AACCTTTTCGTCAATTGACCCCCCTTTACCTGTCAATATCTATTCCTTAAAGGACATGTG 3250       3260       3270       3280       3290       3300
CAGATTGGAAATGGAGTGAAACAAGCCCTCCCATGCCATGTCCCCGTGGGCCACGCCTTA
GTCTAACCTTTACCTCACTTTGTTCGGGAGGGTACGGTACAGGGGCACCCGGTGCGGAAT 3310       3320       3330       3340       3350       3360
TGTAAGAATATTTCCATATTTCAGTGGGCACTCCCAACCTCAGCACTTGTCCGTAGGGTC
ACATTCTTATAAAGGTATAAAGTCACCCGTGAGGGTTGGAGTCGTGAACAGGCATCCCAG 3370       3380       3390       3400       3410       3420
ACACGCGTGCCCTGTTGCTGAATGTATGTTGCGTATCCCAAGGCACTGAAGAGGTGGAAA
TGTGCGCACGGGACAACGACTTACATACAACGCATAGGGTTCCGTGACTTCTCCACCTTT 3430       3440       3450       3460       3470       3480
AATAATCGTGTCAATCTGGATGATAGAGAGAAATTAACTTTTCCAAATGAATGTCTTGCC
TTATTAGCACAGTTAGACCTACTATCTCTCTTTAATTGAAAAGGTTTACTTACAGAACGG 3490       3500       3510       3520       3530       3540
TTAAACCCTCTATTTCCTAAAATATTGTTCCTAAATGGTATTTTCAAGTGTAATATTGTG
AATTTGGGAGATAAAGGATTTTATAACAAGGATTTACCATAAAAGTTCACATTATAACAC 3550       3560       3570       3580       3590       3600
AGAACGCTACTGCAGTAGTTGATGTTGTGTGCTGTAAAGGATTTTAGGAGGAATTTGAAA
TCTTGCGATGACGTCATCAACTACAACACACGACATTTCCTAAAATCCTCCTTAAACTTT 3610       3620       3630       3640       3650       3660
CAGGATATTTAAGAGTGTGGATATTTTTAAAATGCAATAAACATCTCAGTATTTGAAGGG
GTCCTATAAATTCTCACACCTATAAAAATTTTACGTTATTTGTAGAGTCATAAACTTCCC 3670       3680       3690       3700       3710       3720
TTTTCTTAAAGTATGTCAAATGACTACAATCCATAGTGAAACTGTAAACAGTAATGGACG
AAAAGAATTTCATACAGTTTACTGATGTTAGGTATCACTTTGACATTTGTCATTACCTGC
```

FIG. 4E

```
        3730      3740      3750      3760      3770      3780
CCAAATTATAGGTAGCTGATTTTGCTGGAGAGTTTAATTACCTTGTGCAGTCAAAGAGCG
GGTTTAATATCCATCGACTAAAACGACCTCTCAAATTAATGGAACACGTCAGTTTCTCGC 3790      3800      3810      3820      3830      3840
CTTCCAGAAGGAATCTCTTAAAACATAATGAGAGGTTTGGTAATGTGATATTTTAAGCTT
GAAGGTCTTCCTTAGAGAATTTTGTATTACTCTCCAAACCATTACACTATAAAATTCGAA 3850      3860      3870      3880      3890      3900
ATTCTTTTTCTTAAAAGAGAGAGGTGACGAAGGAAGGCAGGAATGAAGAAGCACTGCGTG
TAAGAAAAAGAATTTTCTCTCTCCACTGCTTCCTTCCGTCCTTACTTCTTCGTGACGCAC 3910      3920      3930      3940      3950      3960
GCCTCCGGTGGAATGCACGGGGCACAGCCGCGACTCTGCAGGCAGCTTCCCCCCCATGCC
CGGAGGCCACCTTACGTGCCCCGTGTCGGCGCTGAGACGTCCGTCGAAGGGGGGTACGG 3970      3980      3990      4000      4010      4020
CAGGGCTCTGCGCCGTCATGTGAGACTTAAAAAAAAAGTTGAATGACTTCGTGATACTTT
GTCCCGAGACGCGGCAGTACACTCTGAATTTTTTTTTCAACTTACTGAAGCACTATGAAA 4030      4040      4050      4060      4070      4080
GGACTTCTAAATTAAATTTATCAGGCATAAATTATGTAGAATTAGAGGCTTTGAAAATAA
CCTGAAGATTTAATTTAAATAGTCCGTATTTAATACATCTTAATCTCCGAAACTTTTATT 4090      4100      4110      4120      4130      4140
TACTGGTAGGTTGCTCAAAGGTTTTGAAAGAGAAATCGCTAGGTAGGTTACTATCTGGCT
ATGACCATCCAACGAGTTTCCAAAACTTTCTCTTTAGCGATCCATCCAATGATAGACCGA 4150      4160      4170      4180      4190      4200
AATCCATTTCTTATCCTTGACAATTTAATTCATATTTGGGAAACTTTTAGGGAAATGAAA
TTAGGTAAAGAATAGGAACTGTTAAATTAAGTATAAACCCTTTGAAAATCCCTTTACTTT 4210      4220      4230      4240      4250      4260
AATAAAAGTCACTGAGTCTGGGTGACATTTTTAAGAATAATATAAATTCAGTTTCAAAC
TTATTTTCAGTGACTCAGACCCACTGTAAAAAATTCTTATTATATTTAAGTCAAAGTTTG 4270      4280      4290      4300      4310      4320
TCTTCTCACATTAAAATTTTGCTGTGAACTCTTACTAAAATGAGTTTTAGGTTCTGTAAG
AGAAGAGTGTAATTTTAAAACGACACTTGAGAATGATTTTACTCAAAATCCAAGACATTC 4330      4340      4350      4360      4370      4380
TGGAAAAATGTGCTTTTATTTTATGGGCCATTTTTACCACAACTAATCTTGCCTTGGATT
ACCTTTTTACACGAAAATAAAATACCCGGTAAAAATGGTGTTGATTAGAACGGAACCTAA 4390      4400      4410      4420      4430
ACTAAGCATCTCCTGCGATCCCACAGAGGACTGTGGTGGCCACAGGAGCTGAA
TGATTCGTAGAGGACGCTAGGGTGTCTCCTGACACCACCGGTGTCCTCGACTT
```

FIG. 4F

Sequence Range: 1 to 1276

```
            10         20         30         40         50         60
     ATAGGAGTGGAGAACATGCACAATTACTGCTTTGTGTTTGCTCTGGGATACCTCACAGTG
     TATCCTCACCTCTTGTACGTGTTAATGACGAAACACAAACGAGACCCTATGGAGTGTCAC
       I  G  V  E  N  M  H  N  Y  C  F  V  F  A  L  G  Y  L  T  V>

70         80         90        100        110        120
     TGCCAAGTTACTCGAGTCTATATCTTTGACTATGGACAATATTCTGCTGATTTTTCAGGC
     ACGGTTCAATGAGCTCAGATATAGAAACTGATACCTGTTATAAGACGACTAAAAAGTCCG
       C  Q  V  T  R  V  Y  I  F  D  Y  G  Q  Y  S  A  D  F  S  G>

130        140        150        160        170        180
     CCAATGATGATCATTACTCAGAAGATCACTAGTTTGGCTTGCGAAATACATGATGGGATG
     GGTTACTACTAGTAATGAGTCTTCTAGTGATCAAACCGAACGCTTTATGTACTACCCTAC
       P  M  M  I  I  T  Q  K  I  T  S  L  A  C  E  I  H  D  G  M>

190        200        210        220        230        240
     TTTCGGAAGGATGAAGAACTGACTTCCTCACAGAGGGATTTAGCTGTAAGGCGCATGCCA
     AAAGCCTTCCTACTTCTTGACTGAAGGAGTGTCTCCCTAAATCGACATTCCGCGTACGGT
       F  R  K  D  E  E  L  T  S  S  Q  R  D  L  A  V  R  R  M  P>

250        260        270        280        290        300
     AGCTTACTGGAGTATTTGAGTTACAACTGTAACTTCATGGGGATCCTGGCAGGCCCACTT
     TCGAATGACCTCATAAACTCAATGTTGACATTGAAGTACCCCTAGGACCGTCCGGGTGAA
       S  L  L  E  Y  L  S  Y  N  C  N  F  M  G  I  L  A  G  P  L>

310        320        330        340        350        360
     TGCTCTTACAAAGACTACATTACTTTCATTGAAGGCAGATCATACCATATCACACAATCT
     ACGAGAATGTTTCTGATGTAATGAAAGTAACTTCCGTCTAGTATGGTATAGTGTGTTAGA
       C  S  Y  K  D  Y  I  T  F  I  E  G  R  S  Y  H  I  T  Q  S>

370        380        390        400        410        420
     GGTGAAAATGGAAAAGAAGAGACACAGTATGAAAGAACAGNAGCCATCTCCAAATGTAAG
     CCACTTTTACCTTTTCTTCTCTGTGTCATACTTTCTTGTCNTCGGTAGAGGTTTACATTC
       G  E  N  G  K  E  E  T  Q  Y  E  R  T  X  A  I  S  K  C  K>

430        440        450        460        470        480
     GTCATGAGATTTATCTGGAGCCTTTACAGCATGTATTGNACTGCGGKTGTTCAGAAGCTC
     CAGTACTCTAAATAGACCTCGGAAATGTCGTACATAACNTGACGCCMACAAGTCTTCGAG
       V  M  R  F  I  W  S  L  Y  S  M  Y  X  T  A  X  V  Q  K  L>

490        500        510        520        530        540
     TTAGTTTGTGGGCTGTCCTTGTTATTTCACTTGACCATCTGTACAACATTACCTGTGGAG
     AATCAAACACCCGACAGGAACAATAAAGTGAACTGGTAGACATGTTGTAATGGACACCTC
       L  V  C  G  L  S  L  L  F  H  L  T  I  C  T  T  L  P  V  E>

550        560        570        580        590        600
     TACAACATTGATGAGCATTTTCAAGCTACAGCTTCGTGGCCAACAAAGATTATCTATCTG
     ATGTTGTAACTACTCGTAAAAGTTCGATGTCGAAGCACCGGTTGTTTCTAATAGATAGAC
       Y  N  I  D  E  H  F  Q  A  T  A  S  W  P  T  K  I  I  Y  L>

```
TATATCTCTCTTTTGGCTGCCAGACCCAAATACTATTTTGCATGGACGCTAGCTGATGCC
ATATAGAGAGAAAACCGACGGTCTGGGTTTATGATAAAACGTACCTGCGATCGACTACGG
 Y  I  S  L  L  A  A  R  P  K  Y  Y  F  A  W  T  L  A  D  A>

670       680       690       700       710       720
ATTAATAATGCTGCAGGCTTTGGTTTCAGAGGGTATGACGAAAATGGAGCAGCTCGCTGG
TAATTATTACGACGTCCGAAACCAAAGTCTCCCATACTGCTTTTACCTCGTCGAGCGACC
 I  N  N  A  A  G  F  G  F  R  G  Y  D  E  N  G  A  A  R  W>

730       740       750       760       770       780
GACTTAATTTCCAATTTGAGAATTCAACAAATAGAGATGTCAACAAGTTTCAAGATGTTT
CTGAATTAAAGGTTAAACTCTTAAGTTGTTTATCTCTACAGTTGTTCAAAGTTCTACAAA
 D  L  I  S  N  L  R  I  Q  Q  I  E  M  S  T  S  F  K  M  F>

790       800       810       820       830       840
CTTGATAATTGGAATATTCAGACAGCTCTTTGGCCCAAAAGGGTGTGTTATGAACGAACC
GAACTATTAACCTTATAAGTCTGTCGAGAAACCGGGTTTTCCCACACAATACTTGCTTGG
 L  D  N  W  N  I  Q  T  A  L  W  P  K  R  V  C  Y  E  R  T>

850       860       870       880       890       900
TCCTTCAGTCCAACTATCCAGACGTTCATTCTCCCTGCCATTNTGGCACGGGGTATACCC
AGGAAGTCAGGTTGATAGGTCTGCAAGTAAGAGGGACGGTAANACCGTGCCCCATATGGG
 S  F  S  P  T  I  Q  T  F  I  L  P  A  I  X  A  R  G  I  P>

910       920       930       940       950       960
AGGATATTATCTAACGTTTCTAACAGGGGTGTTAATGACATTAGCAGCAGAGCTATGAGA
TCCTATAATAGATTGCAAAGATTGTCCCCACAATTACTGTAATCGTCGTCTCGATACTCT
 R  I  L  S  N  V  S  N  R  G  V  N  D  I  S  S  R  A  M  R>

970       980       990      1000      1010      1020
AATAACTTTAGACATTATTTCATTGAACCTTCCCAACTGAAATTATTTTATGATGTTMTA
TTATTGAAATCTGTAATAAAGTAACTTGGAAGGGTTGACTTTAATAAAATACTACAAKAT
 N  N  F  R  H  Y  F  I  E  P  S  Q  L  K  L  F  Y  D  V  X>

1030      1040      1050      1060      1070      1080
ACATGGATAGTAAACTCAAGTAGCAATAAGTTACACAGKTGKGSCATTTGTGCTTCTTTC
TGTACCTATCATTTGAGTTCATCGTTATTCAATGTGTCMACMCSGTAAACACGAAGAAAG
 T  W  I  V  N  S  S  S  N  K  L  H  X  X  X  I  C  A  S  F>

1090      1100      1110      1120      1130      1140
TATWAAACCATCACTCACRKTTYACAGGTCCGGTTTATTGCCGGACATACTGGTTCCTCG
ATAWTTTGGTAGTGAGTGYMAARTGTCCAGGCCAAATAACGGCCTGTATGACCAAGGAGC
 Y  X  T  I  T  H  X  X  Q  V  R  F  I  A  G  H  T  G  S  S>

1150      1160      1170      1180      1190      1200
ATAATGGCGTGCCGGACAACGCGGAGAAAGGTACTGGAAGTTCCGCTCCACCAAGTCGTG
TATTACCGCACGGCCTGTTGCGCCTCTTTCCATGACCTTCAAGGCGAGGTGGTTCAGCAC
 I  M  A  C  R  T  T  R  R  K  V  L  E  V  P  L  H  Q  V  V>

1210      1220      1230      1240      1250      1260
GGGGACACTTGGGACAGCTCTTCCACAAGCGCGCCGAAGCCGGACACAACGACGGGGCGG
CCCCTGTGAACCCTGTCGAGAAGGTGTTCGCGCGGCTTCGGCCTGTGTTGCTGCCCCGCC
 G  D  T  W  D  S  S  S  T  S  A  P  K  P  D  T  T  T  G  R>
```

FIG. 5B

```
          1270
GGGGGTGGGGCAACCC
CCCCCACCCCGTTGGG
   G   G   G   A   T
```

FIG. 5C

ANDROGEN REGULATED PROSTATE SPECIFIC NUCLEIC ACIDS

BACKGROUND OF THE INVENTION

1. Field of the Invention

This invention relates generally to cancer and, more specifically, to prostate-specific genes that can be used to diagnose and treat prostate cancer.

2. Background Information

Cancer is currently the second leading cause of mortality in the United States. However, it is estimated that by the year 2000 cancer will surpass heart disease and become the leading cause of death in the United States. Prostate cancer is the most common non-cutaneous cancer in the United States and the second leading cause of male cancer mortality.

Cancerous tumors result when a cell escapes from its normal growth regulatory mechanisms and proliferates in an uncontrolled fashion. As a result of such uncontrolled proliferation, cancerous tumors usually invade neighboring tissues and spread by lymph or blood stream to create secondary or metastatic growths in other tissues. If untreated, cancerous tumors follow a fatal course. Prostate cancer, due to its slow growth profile, is an excellent candidate for early detection and therapeutic intervention.

During the last decade, most advances in prostate cancer research have focused on prostate specific antigen (PSA), a member of the serine protease family that exhibits a prostate-specific expression profile. Serum PSA remains the most widely used tumor marker for monitoring prostate cancer, but its specificity is limited by a high frequency of falsely elevated values in men with benign prostatic hyperplasia (BPH). Other biomarkers of prostate cancer progression have proven to be of limited clinical use in recent surveys because they are not uniformly elevated in men with advanced prostate cancer. Due to the limitations of currently available biomarkers, the identification and characterization of prostate specific genes is essential to the development of more accurate diagnostic methods and therapeutic targets. In many cases, the clinical potential of novel tumor markers can be optimized by utilizing them in combination with other tumor markers in the development of diagnostic and treatment modalities.

Normal prostate tissue consists of three distinct non-stromal cell populations, luminal secretory cells, basal cells, and endocrine paracrine cells. Phenotypic similarities between normal luminal cells and prostate cancer cells, including the expression of PSA, have suggested that prostate adenocarcinomas derive from luminal cells. However, a number of recent studies suggest that at least some prostate cancers can arise from the transformation of basal cells and report the expression of various genes in normal prostate basal cells as well as in prostate carcinoma cells. These genes include prostate stem cell antigen (PSCA), c-met and Bcl-2. Because none of these genes is universally expressed in all basal cells and prostate carcinomas, the utility of these genes as diagnostic markers is limited. Likewise, because PSA is expressed in luminal secretory cells in normal prostate tissue, this antigen has limited utility as a marker for basal cell derived carcinomas.

Thus, there exists a need for the identification of additional prostate specific genes that can be used as diagnostic markers and therapeutic targets for prostate cancer. The present invention satisfies this need and provides related advantages as well.

SUMMARY OF THE INVENTION

The present invention provides androgen responsive prostate specific (ARP) nucleic acid and polypeptide molecules.

The present invention provides a substantially pure ARP1 nucleic acid molecule containing substantially the nucleotide sequence shown as SEQ ID NO:1. The invention also provides a substantially pure ARP1 nucleic acid molecule containing at least 10 contiguous nucleotides of nucleotides 722 to 1026 of SEQ ID NO:1. In one embodiment, the substantially pure ARP1 nucleic acid molecule includes at least 15 contiguous nucleotides of nucleotides 722 to 1026 of SEQ ID NO:1.

The present invention also provides a method of diagnosing or predicting susceptibility to a prostate neoplastic condition in an individual by contacting a sample from the individual with an ARP1 nucleic acid molecule that includes at least 10 contiguous nucleotides of SEQ ID NO:1, determining a test expression level of ARP1 RNA in the sample, and comparing the test expression level to a non-neoplastic control expression level of ARP1 RNA, where an altered test expression level as compared to the control expression level indicates the presence of a prostate neoplastic condition in the individual. In one embodiment, the sample is prostate tissue. In another embodiment, the sample is blood, urine or semen. In yet another embodiment, the ARP1 nucleic acid molecule has a length of 15 to 18 nucleotides.

The present invention further provides a method for treating or reducing the severity of a prostate neoplastic condition in an individual by administering to the individual an ARP1 regulatory agent.

Further provided by the invention is a substantially pure ARP2 nucleic acid molecule containing substantially the nucleotide sequence shown as SEQ ID NO:2. The invention also provides a substantially pure ARP2 nucleic acid molecule that includes at least 10 contiguous nucleotides of nucleotides 1128 to 4509 of SEQ ID NO:2. In one embodiment, such a substantially pure ARP2 nucleic acid molecule includes at least 15 contiguous nucleotides of nucleotides 1128 to 4509 of SEQ ID NO:2.

The present invention additionally provides a method of diagnosing or predicting susceptibility to a prostate neoplastic condition in an individual by contacting a sample from the individual with an ARP2 nucleic acid molecule that contains at least 10 contiguous nucleotides of nucleotides 1128 to 4509 of SEQ ID NO:2, determining a test expression level of ARP2 RNA in the sample, and comparing the test expression level to a non-neoplastic control expression level of ARP2 RNA, where an altered test expression level as compared to the control expression level indicates the presence of a prostate neoplastic condition in the individual. A method of the invention can be practiced, for example, with a sample of prostate tissue, or a sample or blood, urine or semen. An ARP2 nucleic acid molecule useful in a diagnostic method of the invention can be, for example, 15 to 18 nucleotides in length.

The present invention also provides a method for treating or reducing the severity of a prostate neoplastic condition in an individual by administering to the individual an ARP2 regulatory agent.

The present invention additionally provides a substantially pure ARP3 nucleic acid molecule containing a nucleic acid sequence that encodes an ARP3 polypeptide having at least 45% amino acid identity with SEQ ID NO:5. In one embodiment, the substantially pure ARP3 nucleic acid molecule contains a nucleic acid sequence encoding the amino acid sequence shown as SEQ ID NO:5. In another embodiment, the substantially pure ARP3 nucleic acid molecule contains the nucleotide sequence shown as SEQ ID NO:4.

The present invention further provides a method of diagnosing or predicting susceptibility to a prostate neoplastic condition in an individual by contacting a sample from the individual with an ARP3 nucleic acid molecule containing at least 10 contiguous nucleotides of SEQ ID NO:4, determining a test expression level of ARP3 RNA in the sample, and comparing the test expression level to a non-neoplastic control expression level of ARP3 RNA, where an altered test expression level as compared to the control expression level indicates the presence of a prostate neoplastic condition in the individual. In one embodiment, the sample from the individual is prostate tissue. In another embodiment, the sample from the individual is blood, urine or semen. In yet a further embodiment, the ARP3 nucleic acid molecule is 15 to 18 nucleotides in length.

In addition, the present invention provides a substantially pure ARP3 polypeptide which contains an amino acid sequence having at least 45% amino acid identity with SEQ ID NO:5. In one embodiment, the substantially pure ARP3 polypeptide includes the amino acid sequence shown as SEQ ID NO:5. The present invention also provides a substantially pure ARP3 polypeptide fragment that includes at least eight contiguous amino acids of SEQ ID NO:5. Further provided by the invention is a binding agent that selectively binds an ARP3 polypeptide having at least 45% amino acid identity with SEQ ID NO: 5. In one embodiment, the binding agent that selectively binds an ARP3 polypeptide is an antibody.

The present invention also provides a method of diagnosing or predicting susceptibility to a prostate neoplastic condition in an individual by contacting a specimen from the individual with a binding agent that selectively binds an ARP3 polypeptide having at least 45% amino acid identity with SEQ ID NO: 5, determining a test expression level of ARP3 polypeptide in the specimen, and comparing the test expression level to a non-neoplastic control expression level of ARP3 polypeptide, where an altered test expression level as compared to the control expression level indicates the presence of a prostate neoplastic condition in the individual. A specimen useful in a diagnostic method of the invention can be, for example, prostate tissue, or can be, for example, blood, serum, urine or serum. A binding agent useful for determining a test expression level of ARP3 polypeptide in a method of the invention can be, for example, an antibody.

The present invention further provides a method for treating or reducing the severity of a prostate neoplastic condition in an individual by administering to said individual an ARP3 regulatory agent.

Also provided by the invention is a substantially pure ARP4 nucleic acid molecule that contains a nucleic acid sequence encoding an ARP4 polypeptide having at least 50% amino acid identity with SEQ ID NO:7. In one embodiment, the substantially pure ARP4 nucleic acid molecule contains a nucleic acid sequence encoding the amino acid sequence shown as SEQ ID NO:7. In another embodiment, the substantially pure ARP4 nucleic acid molecule includes the nucleotide sequence shown as SEQ ID NO:6.

The present invention also provides a substantially pure ARP4 nucleic acid molecule containing at least 10 contiguous nucleotides of nucleotides 821 to 1940 of SEQ ID NO:6. In one embodiment, the substantially pure ARP4 nucleic acid molecule includes at least 15 contiguous nucleotides of nucleotides 821 to 1940 of SEQ ID NO:6.

The present invention further provides a method of diagnosing or predicting susceptibility to a prostate neoplastic condition in an individual by contacting a sample from the individual with an ARP4 nucleic acid molecule containing at least 10 contiguous nucleotides of SEQ ID NO:6, determining a test expression level of ARP4 RNA in the sample, and comparing the test expression level to a non-neoplastic control expression level of ARP4 RNA, where an altered test expression level as compared to the control expression level indicates the presence of a prostate neoplastic condition in the individual. A sample useful in the invention can be, for example, prostate tissue, or can be, for example, blood, urine or semen. An ARP4 nucleic acid molecule useful in a diagnostic method of the invention can have, for example, a length of 15 to 18 nucleotides.

The present invention additionally provides a substantially pure ARP4 polypeptide containing an amino acid sequence having at least 50% amino acid identity with SEQ ID NO:7. Such a substantially pure ARP4 polypeptide can contain, for example, the amino acid sequence shown as SEQ ID NO:7. The present invention also provides a substantially pure ARP4 polypeptide fragment including at least eight contiguous amino acids of SEQ ID NO:7. The invention additionally provides a binding agent that selectively binds an ARP4 polypeptide having at least 50% amino acid identity with SEQ ID NO:7. In one embodiment, the binding agent that selectively binds an ARP4 polypeptide is an antibody.

The present invention also provides a method of diagnosing or predicting susceptibility to a prostate neoplastic condition in an individual by contacting a specimen from the individual with a binding agent that selectively binds an ARP4 polypeptide having at least 50% amino acid identity with SEQ ID NO: 7, determining a test expression level of ARP4 polypeptide in the specimen, and comparing the test expression level to a non-neoplastic control expression level of ARP4 polypeptide, where an altered test expression level as compared to the control expression level indicates the presence of a prostate neoplastic condition in the individual. In one embodiment, the specimen from the individual is prostate tissue, and, in another embodiment, the specimen from the individual is blood, serum, urine or semen. A particularly useful binding agent that selectively binds an ARP4 polypeptide is an antibody.

The present invention further provides a method for treating or reducing the severity of a prostate neoplastic condition in an individual by administering to the individual an ARP4 regulatory agent.

Further provided by the invention is a substantially pure ARP5 nucleic acid molecule which contains a nucleic acid sequence encoding an ARP5 polypeptide having at least 40% amino acid identity with SEQ ID NO:9. In one embodiment, the substantially pure ARP5 nucleic acid molecule contains a nucleic acid sequence encoding the amino acid sequence shown as SEQ ID NO:9. In another embodiment, the substantially pure ARP5 nucleic acid molecule contains the nucleotide sequence shown as SEQ ID NO:8.

The present invention provides a substantially pure ARP5 nucleic acid molecule containing at least 10 contiguous nucleotides of nucleotides 565 to 1276 of SEQ ID NO:8. In one embodiment, the substantially pure ARP5 nucleic acid molecule includes at least 15 contiguous nucleotides of nucleotides 565 to 1276 of SEQ ID NO:8.

In addition, the present invention provides a method of diagnosing or predicting susceptibility to a prostate neoplastic condition in an individual by contacting a sample from the individual with an ARP5 nucleic acid molecule which includes at least 10 contiguous nucleotides of SEQ ID NO:8, determining a test expression level of ARP5 RNA in the sample, and comparing the test expression level to a non-neoplastic control expression level of ARP5 RNA, where an altered test expression level as compared to the control expression level indicates the presence of a prostate neoplastic condition in the individual. In one embodiment, a sample used in a method of the invention is prostate tissue. In another embodiment, a sample used in a method of the invention is blood, urine or semen. In a further embodiment, the ARP5 nucleic acid molecule has a length of 15 to 18 nucleotides.

The present invention also provides a substantially pure ARP5 polypeptide that contains an amino acid sequence having at least 40% amino acid identity with SEQ ID NO:9. In one embodiment, the substantially pure ARP5 polypeptide contains the amino acid sequence shown as SEQ ID NO:9. The present invention also provides a substantially pure ARP5 polypeptide fragment including at least eight contiguous amino acids of SEQ ID NO:9. Further provided by the invention is a binding agent that selectively binds an ARP5 polypeptide having at least 40% amino acid identity with SEQ ID NO:9, which can be, for example, an antibody.

The present invention also provides a method of diagnosing or predicting susceptibility to a prostate neoplastic condition in an individual by contacting a specimen from the individual with a binding agent that selectively binds an ARP5 polypeptide having at least 40% amino acid identity with SEQ ID NO: 9, determining a test expression level of ARP5 polypeptide in the specimen, and comparing the test expression level to a non-neoplastic control expression level of ARP5 polypeptide, where an altered test expression level as compared to the control expression level indicates the presence of a prostate neoplastic condition in the individual. A specimen useful in the invention can be, for example, prostate tissue, or can be, for example, blood, serum, urine or semen. A binding agent useful in the invention can be, for example, an antibody.

Also provided by the invention is a method for treating or reducing the severity of a prostate neoplastic condition in an individual by administering to the individual an ARP5 regulatory agent.

BRIEF DESCRIPTION OF THE DRAWINGS

FIG. 1 shows the nucleotide (SEQ ID NO:1) sequence of ARP1.

FIG. 2 shows the nucleotide (SEQ ID NO: 2) and amino acid sequence (SEQ ID NO: 3) of ARP2.

FIG. 3 shows the nucleotide (SEQ ID NO:4) and amino acid sequence (SEQ ID NO:5) of ARP3.

FIG. 4 shows the nucleotide (SEQ ID NO:6) and amino acid sequence (SEQ ID NO:7) of ARP4.

FIG. 5 shows the nucleotide (SEQ ID NO:8) and amino acid (SEQ ID NO:9) sequence of ARP5.

DETAILED DESCRIPTION OF THE INVENTION

Figure 6:
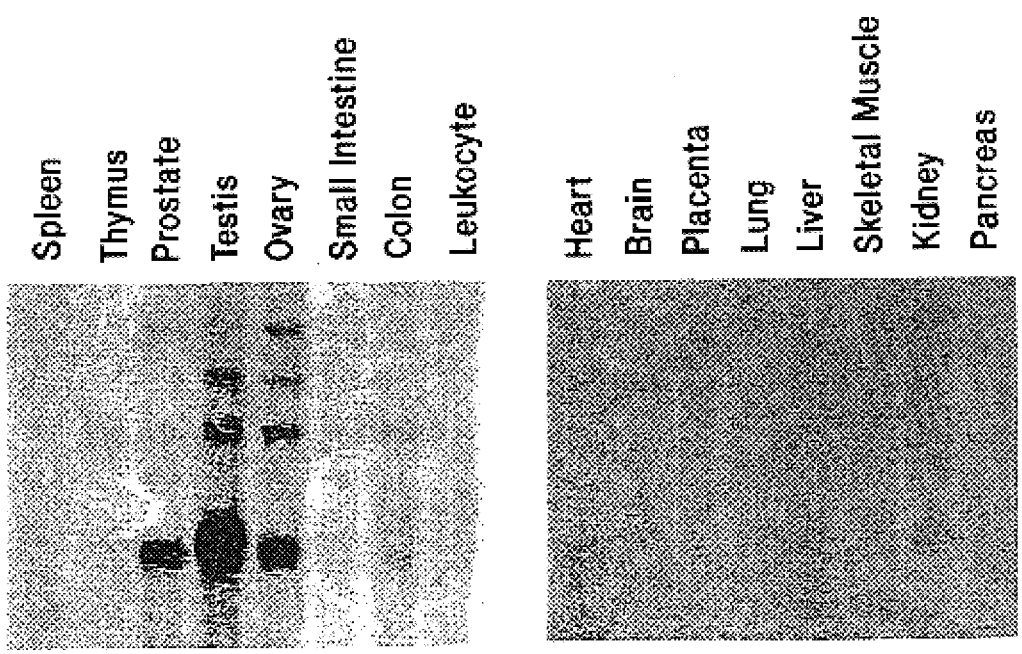
FIG. 6 shows multiple tissue Northern blot analysis of ARP4 expression.

This invention is directed to the discovery of androgen regulated prostate (ARP) expressed nucleic acid molecules.

The androgen regulated prostate expressed nucleic acid molecules and encoded gene products are useful as diagnostic markers for neoplastic conditions of the prostate, and, further, are targets for therapy.

As disclosed herein in Example I, the ARP1 cDNA is an androgen-regulated sequence. The ARP1 nucleic acid sequence is disclosed herein in FIG. 1. As further disclosed herein, the ARP2 cDNA is another androgen-regulated cDNA, which contains 4509 nucleotides and is predicted to encode a protein of 252 amino acids (see FIG. 2). The androgen-regulated ARP3 cDNA contains 2213 nucleotides and is predicted to encode a protein of 538 amino acids (see Example I and FIG. 3). As further disclosed herein, the androgen-regulated ARP4 and ARP5 cDNAs are alternatively spliced mRNA from the same gene. A single nucleotide insertion results in a frameshift change in the coding region. As shown in FIG. 4, the ARP4 nucleic acid sequence contains 4433 nucleotides and is predicted to encode a protein of 141 amino acids. The alternatively spliced ARP5 nucleic acid sequence contains 1276 nucleotides and is predicted to encode a protein of 425 amino acids (see FIG. 5).

Based on these novel prostate-expressed sequences, the invention provides methods for diagnosing prostate neoplastic conditions. An ARP nucleic acid molecule or polypeptide of the invention can be used alone or in combination with other molecules as a specific marker for prostate cells or prostate neoplastic conditions.

The present invention provides a substantially pure ARP1 nucleic acid molecule containing substantially the nucleotide sequence shown as SEQ ID NO:1. The invention also provides a substantially pure ARP1 nucleic acid molecule containing at least 10 contiguous nucleotides of nucleotides 722 to 1026 of SEQ ID NO:1. In one embodiment, the substantially pure ARP1 nucleic acid molecule includes at least 15 contiguous nucleotides of nucleotides 722 to 1026 of SEQ ID NO:1.

The present invention further provides a substantially pure ARP2 nucleic acid molecule containing substantially the nucleotide sequence shown as SEQ ID NO:2. The invention also provides a substantially pure ARP2 nucleic acid molecule that includes at least 10 contiguous nucleotides of nucleotides 1128 to 4509 of SEQ ID NO:2. In one embodiment, such a substantially pure ARP2 nucleic acid molecule includes at least 15 contiguous nucleotides of nucleotides 1128 to 4509 of SEQ ID NO:2.

The present invention additionally provides a substantially pure ARP3 nucleic acid molecule containing a nucleic acid sequence that encodes an ARP3 polypeptide having at least 45% amino acid identity with SEQ ID NO:5. In one embodiment, the substantially pure ARP3 nucleic acid molecule contains a nucleic acid sequence encoding the amino acid sequence shown as SEQ ID NO:5. In another embodiment, the substantially pure ARP3 nucleic acid molecule contains the nucleotide sequence shown as SEQ ID NO:4.

Also provided by the invention is a substantially pure ARP4 nucleic acid molecule that contains a nucleic acid sequence encoding an ARP4 polypeptide having at least 50% amino acid identity with SEQ ID NO:7. In one embodiment, the substantially pure ARP4 nucleic acid molecule contains a nucleic acid sequence encoding the amino acid sequence shown as SEQ ID NO:7. In another embodiment, the substantially pure ARP4 nucleic acid molecule includes the nucleotide sequence shown as SEQ ID NO:6. The present invention further provides a substantially pure ARP4 nucleic acid molecule containing at least 10 contiguous nucleotides of nucleotides 821 to 1940 of SEQ ID NO:6. Such an ARP4 nucleic acid molecule can include, for example, at least 15 contiguous nucleotides of nucleotides 821 to 1940 of SEQ ID NO:6.

Further provided by the invention is a substantially pure ARP5 nucleic acid molecule which contains a nucleic acid sequence encoding an ARP5 polypeptide having at least 40% amino acid identity with SEQ ID NO:9. In one embodiment, the substantially pure ARP5 nucleic acid molecule contains a nucleic acid sequence encoding the amino acid sequence shown as SEQ ID NO:9. In another embodiment, the substantially pure ARP5 nucleic acid molecule contains the nucleotide sequence shown as SEQ ID NO:8. The invention also provides a substantially pure ARP5 nucleic acid molecule containing at least 10 contiguous nucleotides of nucleotides 565 to 1276 of SEQ ID NO:8. In one embodiment, the substantially pure ARP5 nucleic acid molecule includes at least 15 contiguous nucleotides of nucleotides 565 to 1276 of SEQ ID NO:8.

The nucleic acid molecules of the invention corresponding to unique sequences are useful in a variety of diagnostic procedures which employ probe hybridization methods. One advantage of employing nucleic acid hybridization in diagnostic procedures is that very small amounts of sample can be used because the analyte nucleic acid molecule can be amplified to many copies by, for example, polymerase chain reaction (PCR) or other well known methods for nucleic acid molecule amplification and synthesis.

As used herein, the term "nucleic acid molecule" means a single- or double-stranded DNA or RNA molecule including, for example, genomic DNA, cDNA and mRNA. The term is intended to include nucleic acid molecules of both synthetic and natural origin. A nucleic acid molecule of natural origin can be derived from any animal, such as a human, non-human primate, mouse, rat, rabbit, bovine, porcine, ovine, canine, feline, or amphibian, or from a lower eukaryote. A nucleic acid molecule of the invention can be of linear, circular or branched configuration, and can represent either the sense or antisense strand, or both, of a native nucleic acid molecule. A nucleic acid molecule of the invention can further incorporate a detectable moiety such as a radiolabel, a fluorochrome, a ferromagnetic substance, a luminescent tag or a detectable moiety such as biotin.

As used herein, the term "substantially pure nucleic acid molecule" means a nucleic acid molecule that is substantially free from cellular components or other contaminants that are not the desired molecule. A substantially pure nucleic acid molecule can also be sufficiently homogeneous so as to resolve as a band by gel electrophoresis, and generate a nucleotide sequence profile consistent with a predominant species.

In particular embodiments, the present invention provides a substantially pure ARP1 nucleic acid molecule containing at least 10 contiguous nucleotides of nucleotides 722 to 1026 of SEQ ID NO:1; a substantially pure ARP2 nucleic acid molecule that includes at least 10 contiguous nucleotides of nucleotides 1128 to 4509 of SEQ ID NO:2; a substantially pure ARP4 nucleic acid molecule containing at least 10 contiguous nucleotides of nucleotides 821 to 1940 of SEQ ID NO:6; and a substantially pure ARP5 nucleic acid molecule containing at least 10 contiguous nucleotides of nucleotides 565 to 1276 of SEQ ID NO:8. Such a nucleic acid molecule is a portion of a full-length nucleic acid molecule having the ability to selectively hybridize with the parent nucleic acid molecule. As used herein, the term selectively hybridize means an ability to bind the parent nucleic acid molecule without substantial cross-reactivity with a molecule that is not the parent nucleic acid molecule. Therefore, the term selectively hybridize includes specific hybridization where there is little or no detectable cross-reactivity with other nucleic acid molecules. The term also includes minor cross-reactivity with other molecules provided hybridization to the parent nucleic acid molecule is distinguishable from hybridization to the cross-reactive species. Thus, a nucleic acid molecule of the invention can be used, for example, as a PCR primer to selectively amplify a parent nucleic acid molecule; as a selective primer for 5' or 3' RACE to determine additional 5' or 3' sequence of a parent nucleic acid molecule; as a selective probe to identify or isolate a parent nucleic acid molecule on a RNA or DNA blot, or within a genomic or cDNA library; or as a selective inhibitor of transcription or translation of an ARP in a tissue, cell or cell extract.

Several specific nucleic acid sequences are excluded as nucleic acid molecules of the invention. An ARP1 nucleic acid molecule of the invention containing at least 10 contiguous nucleotides of nucleotides 722 to 1026 of SEQ ID NO: 1 excludes one or both of AA404252, AI133138, or any subportion thereof. Similarly, an ARP4 nucleic acid molecule of the invention containing at least 10 contiguous nucleotides of nucleotides 821 to 1940 of SEQ ID NO:6 specifically excludes one or any combination of AW861164, AW856874, AI299663, H59488, W60959, AA659693, AW961788, AA249370, AL133779, or any subportion thereof. In addition, an ARP5 nucleic acid molecule of the invention containing at least 10 contiguous nucleotides of nucleotides 565 to 1276 specifically excludes one or any combination of AW861164, AW856874, or BF130410, or a subportion thereof.

In one embodiment, an ARP3 nucleic acid molecule of the invention specifically excludes the nucleotide sequence AK002597. In another embodiment, an ARP4 nucleic acid molecule of the invention specifically excludes the nucleotide sequence AK012931.

A nucleic acid molecule of the invention includes at least 10 contiguous nucleotides corresponding to the reference nucleic acid molecule, and can include at least 11, 12, 13, 14, 15, 16, 17, 18, 19, 20 or at least 25 nucleotides and, if desired, can include at least 30, 40, 50, 100, 300 or 500 nucleotides or up to the full length of the reference nucleic acid molecule. Nucleic acid molecules of such lengths are able to selectively hybridize with the subject nucleic acid molecule in a variety of detection formats described herein.

As used herein, the term "substantially the nucleotide sequence" in reference to a nucleic acid molecule or nucleic acid probe of the invention includes sequences having one or more additions, deletions or substitutions with respect to the reference sequence, so long as the nucleic acid molecule retains its ability to selectively hybridize with the subject nucleic acid molecule.

Nucleic acid molecules of the invention are useful, in part, as hybridization probes in diagnostic procedures. The nucleic acid molecules can be as long as the full length transcript or as short as about 10–15 nucleotides, for example, 15–18 nucleotides in length. A nucleic acid molecule of the invention that is not a full-length sequence can correspond to coding region or untranslated region sequence. The particular application and degree of desired specificity will be one consideration well known to those skilled in the art in selecting a nucleic acid molecule for a particular application. For example, if it is desired to detect an ARP and other related species, the probe can correspond to a coding sequence and be used in low stringency hybridization conditions. Alternatively, using high stringency conditions with a probe of the invention will select a specific ARP1, ARP2, ARP3, ARP4, or ARP5 nucleic acid molecule. Untranslated region sequences corresponding to an ARP transcript also can be used to construct probes since there is little evolutionary pressure to conserve non-coding domains. Nucleic acid molecules as small as 15 nucleotides are statistically unique sequences within the human genome. Therefore, fragments of 15 nucleotides or more of the ARP sequences disclosed herein as SEQ ID NOS: 1, 2, 4, 6, and 8 can be constructed from essentially any region of an ARP cDNA, mRNA or promoter/regulatory region and be capable of uniquely hybridizing to ARP DNA or RNA.

A nucleic acid molecule of the invention can be produced recombinantly or chemically synthesized using methods well known in the art. Additionally, an ARP nucleic acid molecule can be labeled with a variety of detectable labels including, for example, radioisotopes, fluorescent tags, reporter enzymes, biotin and other ligands for use as a probe in a hybridization method. Such detectable labels can additionally be coupled with, for example, colorimetric or photometric indicator substrate for spectrophotometric detection. Methods for labeling and detecting nucleic acid molecules are well known in the art and can be found described in, for example, Sambrook et al., *Molecular Cloning: A Laboratory Manual*, 2nd ed., Cold Spring Harbor Press, Plainview, N.Y. (1989), and Ausubel et al., *Current Protocols in Molecular Biology* (Supplement 47), John Wiley & Sons, New York (1999).

The nucleic acid molecules of the invention can be hybridized under various stringency conditions readily determined by one skilled in the art. Depending on the particular assay, one skilled in the art can readily vary the stringency conditions to optimize detection of an ARP nucleic acid molecule.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, at least 75% identity, at least 85% identity; or at least 90% identity with the parent or target nucleic acid sequence. Moderately stringent conditions are conditions equivalent to hybridization in 50% formamide, 5× Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The term low stringency hybridization means conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidine, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual*, 2nd., Cold Spring Harbor Press, Plainview, N.Y. (1989); and Ausubel et al., supra, 1999). Nucleic acid molecules encoding polypeptides hybridize under moderately stringent or high stringency conditions to substantially the entire sequence, or substantial portions, for example, typically at least 15–30 nucleotides of an ARP nucleic acid sequence.

The invention also provides a modification of an ARP nucleotide sequence that hybridizes to an ARP nucleic acid molecule, for example, an ARP nucleic acid molecule referenced herein as SEQ ID NO:1, 2, 4, 6 or 8, under moderately stringent conditions. Modifications of ARP nucleotide sequences, where the modification has at least 60% identity to an ARP nucleotide sequence, are also provided. The invention also provides modification of an ARP nucleotide sequence having at least 65% identity, at least 70% identity, at least 75% identity, at least 80% identity, at least 85% identity, at least 90% identity, or at least 95% identity to SEQ ID NO: 1, 2, 4, 6 or 8.

Identity of any two nucleic acid sequences can be determined by those skilled in the art based, for example, on a BLAST 2.0 computer alignment, using default parameters. BLAST 2.0 searching is available at http://www.ncbi.nlm.nih.gov/gorf/b12.html., as described by Tatiana et al., *FEMS Microbiol Lett*. 174:247–250 (1999); Altschul et al., *Nucleic Acids Res*., 25:3389–3402 (1997).

The present invention further provides substantially pure ARP polypeptides encoded by the prostate-expressed nucleic acid molecules of the invention. Thus, the invention provides a substantially pure ARP3 polypeptide which contains an amino acid sequence having at least 45% amino acid identity with SEQ ID NO:5. A substantially pure ARP3 polypeptide of the invention can have, for example, the amino acid sequence shown as SEQ ID NO:5. The present invention also provides a substantially pure ARP3 polypeptide fragment, which includes at least eight contiguous amino acids of SEQ ID NO:5.

The present invention also provides a substantially pure ARP4 polypeptide containing an amino acid sequence having at least 50% amino acid identity with SEQ ID NO:7. In one embodiment, the substantially pure ARP4 polypeptide contains the amino acid sequence shown as SEQ ID NO:7. The present invention also provides a substantially pure ARP4 polypeptide fragment including at least eight contiguous amino acids of SEQ ID NO:7.

The present invention additionally provides a substantially pure ARP5 polypeptide, which contains an amino acid sequence having at least 40% amino acid identity with SEQ ID NO:9. Such a substantially pure ARP5 polypeptide of the invention can contain, for example, the amino acid sequence shown as SEQ ID NO:9. The present invention also provides a substantially pure ARP5 polypeptide fragment including at least eight contiguous amino acids of SEQ ID NO:9.

Exemplary polypeptide fragments include those fragments having amino acids 1 to 8, 2 to 9, 3 to 10, of SEQ ID NO: 5, 7 or 9. The invention also encompasses other polypeptide fragments which are potential antigenic fragments capable of eliciting an immune response, and thereby generating antibodies selective for an ARP3, ARP4 or ARP5 polypeptide of the invention. It is understood that, while eight residues is the minimum length of a polypeptide fragment of the invention, a fragment can be longer and can include 9, 10, 11, 12, 13, 14, 15, 18, 20, 25, 30, 35, 40, 45 or more contiguous amino acids of the amino acid sequence shown as SEQ ID NO: 5 in FIG. 3, the amino acid sequence shown as SEQ ID NO: 7 in FIG. 4, or the amino acid sequence shown a SEQ ID NO: 9 in FIG. 5.

The term "ARP3 polypeptide" as used herein, means a polypeptide that is structurally similar to a human ARP3 (SEQ ID NO: 5) and that has at least one biological activity of human ARP3. Such an ARP3 polypeptide has 45% or more amino acid sequence identity to SEQ ID NO:5 and can have, for example, 50%, 55%, 60%, 65%, 70%, 75%, 80%, 85%, 90%, 95% or more sequence identity to human ARP3 (SEQ ID NO:5). Percent amino acid identity can be determined using Clustal W version 1.7 (Thompson et al., *Nucleic Acids Res.* 22:4673–0680 (1994)).

Thus, it is clear to the skilled person that the term "ARP3 polypeptide" encompasses polypeptides with one or more naturally occurring or non-naturally occurring amino acid substitutions, deletions or insertions as compared to SEQ ID NO:5, provided that the peptide has at least 45% amino acid identity with SEQ ID NO: 5 and retains at least one biological activity of human ARP3. An ARP3 polypeptide can be, for example, a naturally occurring variant of human ARP3 (SEQ ID NO:5); a species homolog including mammalian and non-mammalian homologs and murine, bovine, and primate homologs; an ARP3 polypeptide mutated by recombinant techniques, and the like. In view of the above definition, it is clear to the skilled person that the *C. elegans* polypeptide encoded by T25F10.5 (T29520), which shares 39.7% amino acid identity with human ARP3 (SEQ ID NO:5), is not encompassed by the invention. In a particular embodiment, the mouse cDNA amino acid sequence encoded by AK002597 is specifically excluded from the definition of an ARP3 polypeptide.

The term "ARP4 polypeptide" as used herein, means a polypeptide that is structurally similar to a human ARP4 (SEQ ID NO: 7) and that has at least one biological activity of human ARP4. Such an ARP4polypeptide has 50% or more amino acid sequence identity to SEQ ID NO:5 and can have, for example 55%, 60%, 65%, 70%, 75%, 80%, 85%, 90%, 95% or more amino acid sequence identity to human ARP4 (SEQ ID NO:7). Percent amino acid identity can be determined using Clustal W version 1.7 as described above.

Thus, the term "ARP4 polypeptide" encompasses polypeptides with one or more naturally occurring or non-naturally occurring amino acid substitutions, deletions or insertions as compared to SEQ ID NO:7, provided that the peptide has at least 50% amino acid identity with SEQ ID NO: 7 and retains at least one biological activity of human ARP4. An ARP4 polypeptide can be, for example, a naturally occurring variant of human ARP4 (SEQ ID NO:7); a species homolog including mammalian and non-mammalian homologs and murine, bovine, and primate homologs; an ARP4 polypeptide mutated by recombinant techniques; and the like. In view of the above definition, it is clear to the skilled person that the Drosophila polypeptide encoded by AE003831 (AAF58858), which shares 45% amino acid identity with human ARP4 (SEQ ID NO:7), is not encompassed by the invention. In a particular embodiment, the mouse cDNA amino acid sequence encoded by AK012931 is specifically excluded from the definition of an ARP4 polypeptide.

The term "ARP5 polypeptide" as used herein, means a polypeptide that is structurally similar to a human ARP5 (SEQ ID NO: 9) and that has at least one biological activity of human ARP5. Such an ARP5 polypeptide has 40% or more amino acid sequence identity to SEQ ID NO:9 and can have, for example 45%, 50%, 55%, 60%, 65%, 70%, 75%, 80%, 85%, 90%, 95% or more sequence identity to human ARP5 (SEQ ID NO:9). Percent amino acid identity can be determined using Clustal W version 1.7 (Thompson et al., supra, 1994).

The term "ARP5 polypeptide" encompasses polypeptides with one or more naturally occurring or non-naturally occurring amino acid substitutions, deletions or insertions as compared to SEQ ID NO:9, provided that the peptide has at least 40% amino acid identity with SEQ ID NO: 9 and retains at least one biological activity of human ARP5. An ARP5 polypeptide can be, for example, a naturally occurring variant of human ARP5 (SEQ ID NO:9); a species homolog including mammalian and non-mammalian homologs and murine, bovine, and primate homologs; an ARP4 polypeptide mutated by recombinant techniques, and the like. In view of the above definition, it is clear to the skilled person that the Drosophila polypeptide encoded by AE003831 (AAF58858), which shares 35% amino acid identity with human ARP5 (SEQ ID NO:9), is not encompassed by the invention.

Modifications to ARP3, ARP4 and ARP5 polypeptides of SEQ ID NOS:5, 7, or 9 that are encompassed within the invention include, for example, an addition, deletion, or substitution of one or more conservative or non-conservative amino acid residues; substitution of a compound that mimics amino acid structure or function; or addition of chemical moieties such as amino or acetyl groups.

The present invention provides a binding agent that selectively binds an ARP3 polypeptide having at least 45% amino acid identity with SEQ ID NO:5. The present invention also provides a binding agent that selectively binds an ARP4 polypeptide having at least 50% amino acid identity with SEQ ID NO:7. Further provided by the invention is a binding agent that selectively binds an ARP5 polypeptide having at least 40% amino acid identity with SEQ ID NO:9. Particularly useful binding agents of the invention are polyclonal and monoclonal antibodies and binding portions thereof.

As used herein, the term "binding agent" when used in reference to a specified ARP polypeptide, means a compound, including a simple or complex organic molecule, a metal containing compound, carbohydrate, peptide, protein, peptidomimetic, glycoprotein, lipoprotein, lipid, nucleic acid molecule, antibody, or the like that selectively binds the specified ARP3, ARp4 or ARP5 polypeptide, or fragment thereof. For example, a binding agent can be a polypeptide that selectively binds with high affinity or avidity to the specified ARP polypeptide, without substantial cross-reactivity to other unrelated polypeptides. The affinity of a binding agent that selectively binds an ARP polypeptide generally is greater than about $10^5$ $M^{-1}$ and can be greater than about $10^6$ $M^{-1}$. A binding agent also can bind with high affinity; such an agent generally binds with an affinity greater than $10^8$ $M^{-1}$ to $10^9$ $M^{-1}$. Specific examples of such selective binding agents include a polyclonal or monoclonal antibody selective for an ARP3, ARP4 or ARP5 polypeptide, or a fragment thereof containing at least eight contiguous amino acids of SEQ ID NO: 5, 7 or 9; or a nucleic acid molecule, nucleic acid analog, or small organic molecule, identified, for example, by affinity screening of the appropriate library. For certain applications, a binding agent can be utilized that preferentially recognizes a particular conformational or post-translationally modified state of the specified ARP polypeptide. The binding agent can be labeled with a detectable moiety, if desired, or rendered detectable by specific binding to a detectable secondary binding agent.

As used herein, the term "antibody" is used in its broadest sense to mean polyclonal and monoclonal antibodies, including antigen binding fragments of such antibodies. As used herein, the term antigen means a native or synthesized fragment of a polypeptide of the invention. Such an antibody of the invention, or antigen binding fragment of such an antibody, is characterized by having specific binding activity for the specified ARP3, ARP4 or ARP5 polypeptide, or fragment thereof, of at least about $1\times10^5$ $M^{-1}$. Thus, Fab, $F(ab')_2$, Fd and Fv fragments of an anti-ARP antibody, which retain specific binding activity for an ARP polypeptide of the invention, or fragment thereof, are included within the definition of an antibody. Specific binding activity can be readily determined by one skilled in the art, for example, by comparing the binding activity of the antibody to the specified ARP polypeptide, or fragment thereof, versus a control polypeptide that does not include a polypeptide of the invention. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

The term antibody also includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, produced recombinantly or obtained, for example, by screening combinatorial libraries consisting of variable heavy chains and variable light chains as described by Huse et al. (*Science* 246:1275–1281 (1989)). These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

An antibody of the invention can be prepared using as an immunogen an ARP3, ARP4 or ARP5 polypeptide of the invention, which can be prepared from natural sources or produced recombinantly, or a polypeptide fragment of the invention, which contains at least 8 contiguous amino acids of SEQ ID NO: 5, SEQ ID NO: 7 or SEQ ID NO: 9. Such polypeptide fragments are functional antigenic fragments if the antigenic peptides can be used to generate an antibody selective for an ARP polypeptide of the invention. As is well known in the art, a non-immunogenic or weakly immunogenic ARP polypeptide of the invention, or polypeptide fragment thereof, can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art (see, for example, Harlow and Lane, supra, 1988). An immunogenic ARP polypeptide fragment of the invention can also be generated by expressing the peptide portion as a fusion protein, for example, to glutathione S transferase (GST), polyHis or the like. Methods for expressing peptide fusions are well known to those skilled in the art (Ausubel et al., *Current Protocols in Molecular Biology* (Supplement 47), John Wiley & Sons, New York (1999)).

Methods of diagnosing or predicting susceptibility to a prostate neoplastic condition in an individual further are provided by the invention. In particular, the present invention provides a method of diagnosing or predicting susceptibility to a prostate neoplastic condition in an individual by contacting a sample from the individual with an ARP1 nucleic acid molecule that includes at least 10 contiguous nucleotides of SEQ ID NO:1, determining a test expression level of ARP1 RNA in the sample, and comparing the test expression level to a non-neoplastic control expression level of ARP1 RNA, where an altered test expression level as compared to the control expression level indicates the presence of a prostate neoplastic condition in the individual. In one embodiment, the ARP1 nucleic acid molecule has a length of 15 to 18 nucleotides.

The present invention additionally provides a method of diagnosing or predicting susceptibility to a prostate neoplastic condition in an individual by contacting a sample from the individual with an ARP2 nucleic acid molecule that contains at least 10 contiguous nucleotides of nucleotides 1128 to 4509 of SEQ ID NO:2, determining a test expression level of ARP2 RNA in the sample, and comparing the test expression level to a non-neoplastic control expression level of ARP2 RNA, where an altered test expression level as compared to the control expression level indicates the presence of a prostate neoplastic condition in the individual. An ARP2 nucleic acid molecule useful in the invention can contain, for example 15 to 18 nucleotides.

The present invention further provides a method of diagnosing or predicting susceptibility to a prostate neoplastic condition in an individual by contacting a sample from the individual with an ARP3 nucleic acid molecule containing at least 10 contiguous nucleotides of SEQ ID NO:4, determining a test expression level of ARP3 RNA in the sample, and comparing the test expression level to a non-neoplastic control expression level of ARP3 RNA, where an altered test expression level as compared to the control expression level indicates the presence of a prostate neoplastic condition in the individual. An ARP3 nucleic acid molecule useful in the invention can contain, for example 15 to 18 nucleotides.

The present invention further provides a method of diagnosing or predicting susceptibility to a prostate neoplastic condition in an individual by contacting a sample from said individual with an ARP4 nucleic acid molecule containing at least 10 contiguous nucleotides of SEQ ID NO:6, determining a test expression level of ARP4 RNA in the sample, and comparing the test expression level to a non-neoplastic control expression level of ARP4 RNA, where an altered test expression level as compared to the control expression level indicates the presence of a prostate neoplastic condition in the individual. In one embodiment, the ARP4 nucleic acid molecule is 15 to 18 nucleotides in length.

Further provided by the invention is a method of diagnosing or predicting susceptibility to a prostate neoplastic condition in an individual by contacting a sample from said individual with an ARP5 nucleic acid molecule includes at least 10 contiguous nucleotides of SEQ ID NO:8, determining a test expression level of ARP5 RNA in the sample, and comparing the test expression level to a non-neoplastic control expression level of ARP5 RNA, where an altered test expression level as compared to the control expression level indicates the presence of a prostate neoplastic condition in the individual. In one embodiment the ARP5 nucleic acid molecule is 15 to 18 nucleotides in length.

In the diagnostic methods of the invention, the sample can be, for example, a prostate tissue, or can be, for example, a fluid such as blood, urine or semen. The non-neoplastic control expression level can be determined, for example, using a normal prostate cell or an androgen-dependent cell line.

As described herein, the term "prostate neoplastic condition" means a benign or malignant or metastatic prostate lesion of proliferating cells. For example, primary prostate tumors are classified into stages TX, T0, T1, T2, T3, and T4. Metastatic prostate cancer is classified into stages D1, D2, and D3. The term further includes prostate neoplasm. Each of the above conditions is encompassed within the term "prostate neoplastic condition."

As used herein, the term "sample" means any biological fluid, cell, tissue, organ or portion thereof, that includes or potentially includes an ARP nucleic acid molecule. The term sample includes materials present in an individual as well as materials obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule. A sample can be prepared by methods known in the art suitable for the particular format of the detection method.

As used herein, the term "test expression level" is used in reference to ARP RNA expression or to ARP polypeptide expression as discussed below and means the extent, amount or rate of synthesis of the specified ARP RNA or polypeptide. The amount or rate of synthesis can be determined by measuring the accumulation or synthesis of the specified ARP RNA or polypeptide, or by measuring an activity associated with a polypeptide of the invention.

As used herein, an "altered test expression level" means a test expression level that is either elevated or reduced as compared to a control expression level. One skilled in the art understands that such an elevation or reduction is not within the inherent variability of the assay and generally is an expression level that is at least two-fold elevated or reduced. An altered test expression level can be, for example, two-fold, five-fold, ten-fold, 100-fold, 200-fold, or 1000-fold increased in the extent, amount or rate of synthesis of the specified RNA or polypeptide as compared to a control expression level of the specified ARP RNA or polypeptide. An altered test expression level also can be, for example, two-fold, five-fold, ten-fold, 100-fold, 200-fold, or 1000-fold decreased in the extent, amount or rate of synthesis of the specified ARP RNA or polypeptide compared to a control expression level of the same ARP RNA or polypeptide.

As used herein, the term "non-neoplastic control expression level" means an ARP RNA expression level or to an ARP polypeptide expression level as discussed below used as a baseline for comparison to a test expression level. For example, a suitable control expression level can be the expression level of ARP nucleic acid or polypeptide from a non-neoplastic prostate cell or a fluid sample obtained from a normal individual. Another suitable non-neoplastic control is a prostate cell line that is androgen-dependent. It is understood that ARP nucleic acid or polypeptide expression levels determined in cell lines generally are determined under androgen-depleted growth conditions which can correlate to non-neoplastic control expression levels. The response of an androgen-depleted androgen-dependent prostate cell line to androgen stimulation will be indicative of ARP nucleic acid or polypeptide expression levels in neoplastic cells. The control expression level can be determined simultaneously with one or more test samples or, alternatively, expression levels can be established for a particular type of sample and standardized to internal or external parameters such as protein or nucleic acid content, cell number or mass of tissue. Such standardized control samples can then be directly compared with results obtained from the test sample. As indicated above, an increase of two-fold or more, for example, of a test expression level of the specified ARP nucleic acid or polypeptide indicates the presence of a prostate neoplastic condition or pathology in the tested individual.

A detectable label can be useful in a method of the invention and refers to a molecule that renders a nucleic acid molecule of the invention detectable by an analytical method. An appropriate detectable label depends on the particular assay format; such labels are well known by those skilled in the art. For example, a detectable label selective for a nucleic acid molecule can be a complementary nucleic acid molecule, such as a hybridization probe, that selectively hybridizes to the nucleic acid molecule. A hybridization probe can be labeled with a measurable moiety, such as a radioisotope, fluorochrome, chemiluminescent marker, biotin, or other moiety known in the art that is measurable by analytical methods. A detectable label also can be a nucleic acid molecule without a measurable moiety. For example, PCR or RT-PCR primers can be used without conjugation to selectively amplify all or a desired portion of the nucleic acid molecule. The amplified nucleic acid molecules can then be detected by methods known in the art.

The present invention also provide diagnostic methods that rely on a binding agent that selectively binds the specified ARP. A method of the invention for diagnosing or predicting susceptibility to a prostate neoplastic condition in an individual is practiced by contacting a specimen from an individual with a binding agent that selectively binds an ARP3 polypeptide having at least 45% amino acid identity with SEQ ID NO:5; determining a test expression level of ARP3 polypeptide in the specimen; and comparing the test expression level to a non-neoplastic control expression level of ARP3 polypeptide, where an altered test expression level as compared to the control expression level indicates the presence of a prostate neoplastic condition in the individual.

The present invention also provides a method for diagnosing or predicting susceptibility to a prostate neoplastic condition in an individual by contacting a specimen from the individual with a binding agent that selectively binds an ARP4 polypeptide having at least 50% amino acid identity with SEQ ID NO:7; determining a test expression level of ARP4 polypeptide in the specimen; and comparing the test expression level to a non-neoplastic control expression level of ARP4 polypeptide, where an altered test expression level as compared to the control expression level indicates the presence of a prostate neoplastic condition in the individual.

Further provided by the invention is a method for diagnosing or predicting susceptibility to a prostate neoplastic condition in an individual by contacting a specimen from an individual with a binding agent that selectively binds an ARP5 polypeptide having at least 40% amino acid identity with SEQ ID NO:9; determining a test expression level of ARP5 polypeptide in the specimen; and comparing the test expression level to a non-neoplastic control expression level of ARP5 polypeptide, where an altered test expression level as compared to the control expression level indicates the presence of a prostate neoplastic condition in the individual.

In a method of the invention, the specimen can contain, for example, a prostate cell or prostate tissue and, in one embodiment, is a fluid such as blood, serum, urine or semen. The control expression level can be determined, for example, using a normal prostate cell or an androgen-dependent cell line. In addition, a binding agent selective for a polypeptide of the invention can be, for example, an antibody, and, if desired, can further include a detectable label.

As used herein, the term "specimen" means any biological material including fluid, cell, tissue, organ or portion thereof, that contains or potentially contains an ARP polypeptide of the invention. The term specimen includes materials present in an individual as well as materials obtained or derived from the individual. For example, a specimen can be a histologic section obtained by biopsy, or cells that are placed in or adapted to tissue culture. A specimen further can be a subcellular fraction or extract, or a crude or substantially pure protein preparation. A specimen can be prepared by methods known in the art suitable for the particular format of the detection method.

In methods of the invention, the specimen can be, for example, a prostate cell or prostate tissue such as a tissue biopsy. A specimen can also be a fluid sample, for example, blood, serum, urine or semen. A normal specimen can be, for example, a normal prostate cell or an androgen-dependent cell line.

These diagnostic methods of the invention rely on a binding agent. As described above, the term "binding agent" when used in reference to an ARP polypeptide, is intended to mean a compound, including a simple or complex organic molecule, a metal containing compound, carbohydrate, peptide, protein, peptidomimetic, glycoprotein, lipoprotein, lipid, nucleic acid molecule, antibody, or the like that selectively binds the specified ARP polypeptide, or fragment thereof. The binding agent can be labeled with a detectable moiety, if desired, or rendered detectable by specific binding to a detectable secondary binding agent. Exemplary binding agents are discussed hereinabove.

A prostate neoplastic condition is a benign or malignant prostate lesion of proliferating cells. Prostate neoplastic conditions include, for example, prostate interepithelial neoplasia (PIN) and prostate cancer. Prostate cancer is an uncontrolled proliferation of prostate cells which can invade and destroy adjacent tissues as well as metastasize. Primary prostate tumors can be classified into stages TX, T0, T1, T2, T3, and T4 and metastatic tumors can be classified into stages D1, D2 and D3. Similarly, there are classifications known by those skilled in the art for the progressive stages of precancerous lesions or PIN. The methods herein are applicable for the diagnosis or treatment of any or all stages of prostate neoplastic conditions.

The methods of the invention are also applicable to prostate pathologies other than neoplastic conditions. Such other pathologies include, for example, benign prostatic hyperplasia (BPH) and prostatitis. BPH is one of the most common diseases in adult males. Histological evidence of BPH has been found in more than 40% of men in their fifties and almost 90% of men in their eighties. The disease results from the accumulation of non-malignant nodules arising in a small region around the proximal segment of the prostatic urethra which leads to an increase in prostate volume. If left untreated, BPH can result in acute and chronic retention of urine, renal failure secondary to obstructive uropathy, serious urinary tract infection and irreversible bladder decompensation. Prostatitis is an infection of the prostate. Other prostate pathologies known to those skilled in the art exist as well and are similarly applicable for diagnosis or treatment using the methods of the invention. Various neoplastic conditions of the prostate as well as prostate pathologies can be found described in, for example, *Campbell's Urology*, Seventh Edition, W. B. Saunders Company, Philadelphia 1998). Therefore, the methods of the invention are applicable to both prostate neoplastic conditions and prostate pathologies.

Therefore, the invention provides a method for both diagnosing and prognosing a prostate neoplastic condition including prostate cancer and prostate interepithelial neoplasia as well as other prostate pathologies such as BPH and prostatitis.

The invention provides a method of diagnosing or predicting prostate neoplastic conditions based on a finding of a positive correlation between a test expression level of an ARP polypeptide or nucleic acid in neoplastic cells of the prostate and the degree or extent of the neoplastic condition or pathology. The diagnostic methods of the invention are applicable to numerous prostate neoplastic conditions and pathologies as described above. One consequence of progression into these neoplastic and pathological conditions can be altered expression of ARP polypeptide or nucleic acid in prostate tissue. The alteration in ARP polypeptide or nucleic acid expression in individuals suffering from a prostate neoplastic condition can be measured by comparing the amount of ARP polypeptide or nucleic acid to that found, for example, in normal prostate tissue samples or in normal blood or serum samples. A two-fold or more increase or decrease in a test expression level in a prostate cell sample relative to a non-neoplastic control expression sample obtained, for example, from normal prostate cells or from an androgen-dependent cell line is indicative of a prostate neoplastic condition or pathology. Similarly, an alteration in ARP polypeptide or nucleic acid expression leading to an increased or decreased secretion into the blood or other circulatory fluids of the individual compared to a non-neoplastic control blood or fluid samples also can be indicative of a prostate neoplastic condition or pathology. For example, an alteration in ARP polypeptide or nucleic acid expression can lead to a two-fold, five-fold, ten-fold, 100-fold, 200-fold or 1000-fold increased secretion into the blood or other circulatory fluids of the individual compared to a non-neoplastic control blood or fluid samples. As another example, an alteration in ARP polypeptide or nucleic acid expression can lead to a two-fold, five-fold, ten-fold, 100-fold, 200-fold or 1000-fold decreased secretion into the blood or other circulatory fluids of the individual compared to a non-neoplastic control blood or fluid samples.

As a diagnostic indicator, an ARP polypeptide or nucleic acid molecule can be used qualitatively to positively identify a prostate neoplastic condition or pathology as described above. Alternatively, ARP polypeptide or nucleic acid molecule also can be used quantitatively to determine the degree or susceptibility of a prostate neoplastic condition or pathology. For example, successive increases or decreases in the expression levels of ARP polypeptide or nucleic acid can be used as a predictive indicator of the degree or severity of a prostate neoplastic condition or pathology. For example, increased expression can lead to a rise in accumulated levels and can be positively correlated with increased severity of a neoplastic condition of the prostate. A higher level of ARP polypeptide or nucleic acid expression can be correlated with a later stage of a prostate neoplastic condition or pathology. For example, increases in expression levels of two-fold or more compared to a normal sample can be indicative of at least prostate neoplasia. ARP polypeptide or nucleic acid molecule also can be used quantitatively to distinguish between pathologies and neoplastic conditions as well as to distinguish between the different types of neoplastic conditions.

Correlative alterations can be determined by comparison of ARP polypeptide or nucleic acid expression from the individual having, or suspected of having, a neoplastic condition of the prostate to expression levels of ARP polypeptide or nucleic acid from known specimens or samples determined to exhibit a prostate neoplastic condition. Alternatively, correlative alterations also can be determined by comparison of a test expression level of ARP polypeptide or nucleic acid expression to expression levels of other known markers of prostate cancer such as prostate specific antigen (PSA), glandular kallikrein 2 (hK2) and prostase/PRSS18. These other known markers can be used, for example, as an internal or external standard for correlation of stage-specific expression with altered ARP polypeptide or nucleic acid expression and severity of the neoplastic or pathological condition. Conversely, a regression in the severity of a prostate neoplastic condition or pathology can be followed by a corresponding reversal in ARP polypeptide or nucleic acid expression levels and can similarly be assessed using the methods described herein.

Given the teachings and guidance provided herein, those skilled in the art will know or can determine the stage or severity of a prostate neoplastic condition or pathology based on a determination of ARP polypeptide or nucleic acid expression and correlation with a prostate neoplastic condition or pathology. A correlation can be determined using known procedures and marker comparisons as described herein. For a review of recognized values for such other marker in normal versus pathological tissues, see, for example, *Campbell's Urology*, Seventh Edition, W. B. Saunders Company, Philadelphia (1998).

The use of ARP polypeptide or nucleic acid expression levels in prostate cells, the circulatory system and urine as a diagnostic indicator of a prostate pathology allows for early diagnosis as a predictive indicator when no physiological or pathological symptoms are apparent. The methods are particularly applicable to any males over age 50, African-American males and males with familial history of prostate neoplastic conditions or pathologies. The diagnostic methods of the invention also are particularly applicable to individuals predicted to be at risk for prostate neoplastic conditions or pathologies by reliable prognostic indicators prior to onset of overt clinical symptoms. All that is necessary is to determine the ARP polypeptide or nucleic acid prostate tissue or circulatory or bodily fluid expression levels to determine whether there is altered ARP polypeptide or nucleic acid levels in the individual suspected of having a prostate pathology compared to a control expression level such as the level observed in normal individuals. Those skilled in the art will know by using routine examinations and practices in the field of medicine those individuals who are applicable candidates for diagnosis by the methods of the invention.

For example, individuals suspected of having a prostate neoplastic condition or pathology can be identified by exhibiting presenting signs of prostate cancer which include, for example, a palpable nodule (>50% of the cases), dysuria, cystitis and prostatitis, frequency, urinary retention, or decreased urine stream. Signs of advanced disease include pain, uremia, weight loss and systemic bleeding. Prognostic methods of this invention are applicable to individuals after diagnosis of a prostate neoplastic condition, for example, to monitor improvements or identify residual neoplastic prostate cells using, for example, imaging methods known in the art and which target ARP polypeptide or nucleic acid. Therefore, the invention also provides a method of predicting the onset of a prostate neoplastic condition or pathology by determining an altered test expression level of one of the ARP nucleic acid molecules or polypeptides of the invention.

The diagnostic methods of the invention are applicable for use with a variety of different types of samples or specimens isolated or obtained from an individual having, or suspected of having a prostate neoplastic condition or prostate pathology. For example, samples applicable for use in one or more diagnostic formats of the invention include tissue and cell samples. A tissue or cell sample or specimen can be obtained, for example, by biopsy or surgery. As described below, and depending on the format of the method, the tissue can be used whole or subjected to various methods known in the art to disassociate the sample or specimen into smaller pieces, cell aggregates or individual cells. Additionally, when combined with amplification methods such as polymerase chain reaction (PCR), a single prostate cell can be a sample sufficient for use in diagnostic assays of the invention which employ hybridization detection methods. Similarly, when measuring ARP polypeptide or activity levels, amplification of the signal with enzymatic coupling or photometric enhancement can be employed using only a few or a small number of cells.

Whole tissue obtained from a prostate biopsy or surgery is one example of a prostate cell sample or specimen. Whole tissue prostate cell samples or specimens can be assayed employing any of the formats described below. For example, the prostate tissue sample can be mounted and hybridized in situ with ARP nucleic acid probes. Similar histological formats employing protein detection methods and in situ activity assays also can be used to detect an ARP polypeptide in whole tissue prostate cell specimens. Protein detection methods include, for example, staining with an ARP specific antibody and activity assays. Such histological methods as well as others well known to those skilled in the art are applicable for use in the diagnostic methods of the invention using whole tissue as the source of a prostate cell specimen. Methods for preparing and mounting the samples and specimens are similarly well known in the art.

Individual prostate cells and cell aggregates from an individual having, or suspected of having a prostate neoplastic condition or pathology also are prostate cell samples which can be analyzed for an altered test expression level in a method of the invention. The cells can be grown in culture and analyzed in situ using procedures such as those described above. Whole cell samples expressing cell surface markers associated with ARP polypeptide or nucleic acid expression can be rapidly tested using fluorescent or magnetic activated cell sorting (FACS or MACS) with labeled binding agents selective for the surface marker or using binding agents selective for epithelial or prostate cell populations, for example, and then determining a test expression level of a specified ARP polypeptide or nucleic acid within this population. The test expression level can be determined using, for example, binding agents selective for polypeptides of the invention or by hybridization to a specific nucleic acid molecule of the invention. Other methods for measuring the expression level of ARP polypeptide or nucleic acid in whole cell samples are known in the art and are similarly applicable in any of the diagnostic formats described below.

The tissue or whole cell prostate cell sample or specimen obtained from an individual also can be analyzed for increased ARP polypeptide or nucleic acid expression by lysing the cell and measuring a test expression levels of ARP polypeptide or nucleic acid in the lysate, a fractionated portion thereof or a purified component thereof using any of diagnostic formats described herein. For example, if a hybridization format is used, ARP RNA can be amplified directly from the lysate using PCR, or other amplification procedures well known in the art such as RT-PCR, 5' or 3' RACE to directly measure the expression levels of ARP nucleic acid molecules. RNA also can be isolated and probed directly such as by solution hybridization or indirectly by hybridization to immobilized RNA. Similarly, when determining a test expression level of ARP using polypeptide detection formats, lysates can be assayed directly, or they can be further fractionated to enrich for ARP polypeptide and its corresponding activity. Numerous other methods applicable for use with whole prostate cell samples are well known to those skilled in the art and can accordingly be used in the methods of the invention.

The prostate tissue or cell sample or specimen can be obtained directly from the individual or, alternatively, it can be obtained from other sources for testing. Similarly, a cell sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the diagnostic methods of the invention is that they do not require histological analysis of the sample. As such, the sample can be initially disaggregated, lysed, fractionated or purified and the active component stored for later diagnosis.

The diagnostic methods of the invention are applicable for use with a variety of different types of samples and specimens other than prostate cell samples. For example, an ARP polypeptide or fragment thereof that is released into the extracellular space, including circulatory fluids as well as other bodily fluids, can be detected in a method of the invention. In such a case, the diagnostic methods of the invention are practiced with fluid samples collected from an individual having, or suspected of having a neoplastic condition of the prostate or a prostate pathology.

Fluid samples and specimens, which can be measured for ARP polypeptide or nucleic acid expression levels, include, for example, blood, serum, lymph, urine and semen. Other bodily fluids are known to those skilled in the art and are similarly applicable for use as a sample or specimen in the diagnostic methods of the invention. One advantage of analyzing fluid samples or specimens is that they are readily obtainable, in sufficient quantity, without invasive procedures as required by biopsy and surgery. Analysis of fluid samples or specimens such as blood, serum and urine will generally be in the diagnostic formats described herein which measure ARP polypeptide levels or activity. As the ARP related polypeptide is circulating in a soluble form, the methods will be similar to those which measure expression levels from cell lysates, fractionated portions thereof or purified components.

Prostate neoplastic conditions and prostate pathologies can be diagnosed, predicted or prognosed by measuring a test expression level of ARP polypeptide or nucleic acid in a prostate cell sample, circulating fluid or other bodily fluid obtained from the individual. As described herein, a test or control expression level can be measured by a variety of methods known in the art. For example, a test expression level of a specified ARP can be determined by measuring the amount of ARP RNA or polypeptide in a sample or specimen from the individual. Alternatively, a test expression level of ARP can be determined by measuring the amount of an ARP activity in a specimen, the amount of activity being indicative of the specified ARP polypeptide expression level.

One skilled in the art can readily determine an appropriate assay system given the teachings and guidance provided herein and choose a method based on measuring ARP RNA, polypeptide or activity. Considerations such as the sample or specimen type, availability and amount will also influence selection of a particular diagnostic format. For example, if the sample or specimen is a prostate cell sample and there is only a small amount available, then diagnostic formats which measure the amount of ARP RNA by, for example, PCR amplification, or which measure ARP-related cell surface polypeptide by, for example, FACS analysis can be appropriate choices for determining a test expression level. Alternatively, if the specimen is a blood sample and the user is analysing numerous different samples simultaneous, such as in a clinical setting, then a multisample format, such as an Enzyme Linked Immunoabsorbant Assay (ELISA), which measures the amount of an ARP polypeptide can be an appropriate choice for determining a test expression level of a specified ARP. Additionally, ARP nucleic acid molecules released into bodily fluids from the neoplastic or pathological prostate cells can also be analyzed by, for example, PCR or RT-PCR. Those skilled in the art will know, or can determine which format is amenable for a particular application and which methods or modifications known within the art are compatible with a particular type of format.

Hybridization methods are applicable for measuring the amount of ARP RNA as an indicator of ARP expression levels. There are numerous methods well known in the art for detecting nucleic acid molecules by specific or selective hybridization with a complementary nucleic acid molecule. Such methods include solution hybridization procedures and solid-phase hybridization procedures where the probe or sample is immobilized to a solid support. Descriptions for such methods can be found in, for example, Sambrook et al., supra, and in Ausubel et al., supra. Specific examples of such methods include PCR and other amplification methods such as RT-PCR, 5' or 3' RACE, RNase protection, RNA blot, dot blot or other membrane-based technologies, dip stick, pin, ELISA or two-dimensional arrays immobilized onto chips as a solid support. These methods can be performed using either qualitative or quantitative measurements, all of which are well known to those skilled in the art.

PCR or RT-PCR can be used with isolated RNA or crude cell lysate preparations. As described previously, PCR is advantageous when there is limiting amounts of starting material. A further description of PCR methods can be found in, for example, Dieffenbach, C. W., and Dveksler, G. S., *PCR Primer: A Laboratory Manual*, Cold Spring Harbor Press, Plainview, N.Y. (1995). Multisample formats such as an ELISA or two-dimensional array offer the advantage of analyzing numerous, different samples in a single assay. Solid-phase dip stick-based methods offer the advantage of being able to rapidly analyze a patient's fluid sample and obtain an immediate result.

Nucleic acid molecules useful for measuring a test expression level of a specified ARP RNA are disclosed herein above. Briefly, for detection by hybridization, an ARP nucleic acid molecule having a detectable label is added to a prostate cell sample or a fluid sample obtained from the individual having, or suspected of having a prostate neoplastic condition or pathology under conditions which allow annealing of the molecule to an ARP RNA. Methods for detecting ARP RNA in a sample can include the use of, for example, RT-PCR. Conditions are well known in the art for both solution and solid phase hybridization procedures. Moreover, optimization of hybridization conditions can be performed, if desired, by hybridization of an aliquot of the sample at different temperatures, durations and in different buffer conditions. Such procedures are routine and well known to those skilled in the art. Following annealing, the sample is washed and the signal is measured and compared with a suitable control or standard value. The magnitude of the hybridization signal is directly proportional to the expression levels of ARP RNA.

The diagnostic procedures described herein can additionally be used in conjunction with other prostate markers, such as prostate specific antigen, human glandular kallikrein 2 (hk2) and prostase/PRSS18 for simultaneous or independent corroboration of a sample. Additionally, ARP polypeptide or nucleic acid expression can be used, for example, in combination with other markers to further distinguish normal basal cells, secretory cells and neoplastic cells of the prostate. Moreover, ARP polypeptide or nucleic acid expression can be used in conjunction with smooth muscle cell markers to distinguish between pathological conditions such as benign prostate hypertrophy (BPH) and neoplasia. Those skilled in the art will know which markers are applicable for use in conjunction with ARP polypeptide or nucleic acid to delineate more specific diagnostic information such as that described above.

The invention also provides diagnostic methods based on determining whether there is an altered test expression level of an ARP3, ARP4 or ARP5 polypeptide using a binding agent that selectively binds the recited polypeptide. Essentially all modes of affinity binding assays are applicable for use in determining a test expression level of an ARP polypeptide in a method of the invention. Such methods are rapid, efficient and sensitive. Moreover, affinity binding methods are simple and can be modified to be performed under a variety of clinical settings and conditions to suit a variety of particular needs. Affinity binding assays which are known and can be used in the methods of the invention include both soluble and solid phase formats. A specific example of a soluble phase affinity binding assay is immunoprecipitation using an ARP selective antibody or other binding agent. Solid phase formats are advantageous in that they are rapid and can be performed easily and simultaneously on multiple different samples without losing sensitivity or accuracy. Moreover, solid phase affinity binding assays are further amenable to high throughput and ultra high throughput screening and automation.

Specific examples of solid phase affinity binding assays include immunoaffinity binding assays such as an ELISA and radioimmune assay (RIA). Other solid phase affinity binding assays are known to those skilled in the art and are applicable to the methods of the invention. Although affinity binding assays are generally formatted for use with an antibody binding molecule that is selective for the analyte or ligand of interest, essentially any binding agent can be alternatively substituted for the selectively binding antibody. Such binding agents include, for example, macromolecules such as polypeptides, peptides, nucleic acid molecules, lipids and sugars as well as small molecule compounds. Methods are known in the art for identifying such molecules which bind selectively to a particular analyte or ligand and include, for example, surface display libraries and combinatorial libraries. Thus, for a molecule other than an antibody to be used in an affinity binding assay, all that is necessary is for the binding agent to exhibit selective binding activity for a polypeptide of the invention.

Various modes of affinity binding formats are similarly known which can be used in the diagnostic methods of the invention. For the purpose of illustration, particular embodiments of such affinity binding assays will be described further in reference to immunoaffinity binding assays. The various modes of affinity binding assays, such as immunoaffinity binding assays, include, for example, solid phase ELISA and RIA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, *Using Antibodies: A Laboratory Manual*, Cold Spring Harbor Laboratory Press, New York (1999).

As with the hybridization methods described previously, the diagnostic formats employing affinity binding can be used in conjunction with a variety of detection labels and systems known in the art to quantitate amounts of a polypeptide of the invention in the analyzed sample. Detection systems include the detection of bound polypeptide on the invention by both direct and indirect means. Direct detection methods include labeling of the ARP-selective antibody or binding agent. Indirect detection systems include, for example, the use of labeled secondary antibodies and binding agents.

Secondary antibodies, labels and detection systems are well known in the art and can be obtained commercially or by techniques well known in the art. The detectable labels and systems employed with the ARP-selective binding agent should not impair binding of the agent to the corresponding ARP polypeptide. Moreover, multiple antibody and label systems can be employed for detecting the bound ARP-selective antibody to enhance the sensitivity of the binding assay if desired.

As with the hybridization formats described previously, detectable labels can be essentially any label that can be quantitated or measured by analytical methods. Such labels include, for example, enzymes, radioisotopes, fluorochromes as well as chemi- and bioluminescent compounds. Specific examples of enzyme labels include horseradish peroxidase (HRP), alkaline phosphatase (AP), β-galactosidase, urease and luciferase.

A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). Luciferin is the substrate compound for luciferase which emits light following ATP-dependent oxidation.

Fluorochrome detection labels are rendered detectable through the emission of light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine are specific examples of fluorochrome detection labels that can be utilized in the affinity binding formats of the invention. A particularly useful fluorochrome is fluorescein or rhodamine.

Chemiluminescent as well as bioluminescent detection labels are convenient for sensitive, non-radioactive detection of an ARP polypeptide and can be obtained commercially from various sources such as Amersham Lifesciences, Inc. (Arlington Heights, Ill.).

Alternatively, radioisotopes can be used as detectable labels in the methods of the invention. Iodine-125 is a specific example of a radioisotope useful as a detectable label.

Signals from detectable labels can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of bound agent can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The diagnostic formats of the present invention can be forward, reverse or simultaneous as described in U.S. Pat. No. 4,376,110 and U.S. Pat. No. 4,778,751. Separation steps for the various assay formats described herein, including the removal of unbound secondary antibody, can be performed by methods known in the art (Harlow and Lane, supra). For example, washing with a suitable buffer can be followed by filtration, aspiration, vacuum or magnetic separation as well as by centrifugation.

A binding agent selective for an ARP polypeptide also can be utilized in imaging methods that are targeted at ARP expressing prostate cells. These imaging techniques have utility in identification of residual neoplastic cells at the primary site following standard treatments including, for example, radical prostatectomy, radiation or hormone therapy. In addition, imaging techniques that detect neoplastic prostate cells have utility in detecting secondary sites of metastasis. A binding agent that selectively binds ARP3, ARP4 or ARP5 can be radiolabeled with, for example, $^{111}$indium and infused intravenously as described by Kahn et al., *Journal of Urology* 152:1952–1955 (1994). The binding agent selective for an ARP polypeptide can be, for example, a monoclonal antibody selective for an ARP polypeptide. Imaging can be accomplished by, for example, radioimmunoscintigraphy as described by Kahn et al., supra.

In one embodiment, the invention provides a method of diagnosing or predicting the susceptibility of a prostate neoplastic condition in an individual suspected of having a neoplastic condition of the prostate, where a test expression level of an ARP polypeptide is determined by measuring the amount of ARP3, ARP4, or ARP5 polypeptide activity. The method is practiced by contacting a specimen from the individual with an agent that functions to measure an activity associated with an ARP3, ARP4, or ARP5 polypeptide of the invention.

As with the hybridization and affinity binding formats described above, activity assays similarly can be performed using essentially identical methods and modes of analysis. Therefore, solution and solid phase modes, including multisample ELISA, RIA and two-dimensional array procedures are applicable for use in measuring an activity associated with an ARP polypeptide. The activity can be measured by, for example, incubating an agent that functions to measure an activity associated with an ARP polypeptide with the sample and determining the amount of product formed that corresponds to ARP3, ARP4 or ARP5 polypeptide activity. The amount of product formed will directly correlate with the ARP3, ARP4 or ARP5 polypeptide activity in the specimen and therefore, with the expression levels of the corresponding polypeptide of the invention in the specimen.

The invention further provides a method of identifying a compound that inhibits ARP3, ARP4 or ARP5 polypeptide activity. The method consists of contacting a specimen containing an ARP polypeptide and an agent that functions to measure an activity associated with an ARP polypeptide with a test compound under conditions that allow formation of a product that corresponds to an ARP polypeptide activity and measuring the amount of product formed, where a decrease in the amount of product formed in the presence of the test compound compared to the absence of the test compound indicates that the compound has ARP polypeptide inhibitory activity. Similarly, compounds that increase the activity of an ARP polypeptide also can be identified. A test compound added to a specimen containing an ARP polypeptide and an agent that functions to measure an activity associated with an ARP polypeptide which increases the amount of product formed compared to the absence of the test compound indicates that the compound increases the corresponding ARP polypeptide activity. Therefore, the invention provides a method of identifying compounds that modulate the activity of an ARP polypeptide. The ARP polypeptide containing specimen used for such a method can be serum, prostate tissue, a prostate cell population or a recombinant cell population expressing an ARP polypeptide.

Those compounds having inhibitory activity are considered as potential ARP polypeptide antagonists and further as potential therapeutic agents for treatment of neoplastic conditions of the prostate. Similarly, those compounds which increase an ARP polypeptide activity are considered as potential ARP polypeptide agonists and further as potential therapeutic agents for the treatment of neoplastic conditions of the prostate. Each of these classes of compounds is encompassed by the term ARP regulatory agent as defined herein.

Within the biological arts, the term "about" when used in reference to a particular activity or measurement is intended to refer to the referenced activity or measurement as being within a range of values encompassing the referenced value and within accepted standards of a credible assay within the art, or within accepted statistical variance of a credible assay within the art.

A reaction system for identifying a compound that inhibits or enhances an ARP polypeptide activity can be performed using essentially any source of ARP polypeptide activity. Such sources include, for example, a prostate cell sample, lysate or fractionated portion thereof; a bodily fluid such as blood, serum or urine from an individual with a prostate neoplastic condition; a recombinant cell or soluble recombinant source, and an in vitro translated source. The ARP polypeptide source is combined with an agent that functions to measure an activity associated with an ARP polypeptide as described above and incubated in the presence or absence of a test inhibitory compound. The amount of product that corresponds to an ARP polypeptide activity that is formed in the presence of the test compound is compared with that in the absence of the test compound. Those test compounds which inhibit product formation are considered to be ARP polypeptide inhibitors. For example, a test compound can inhibit product formation by at least 50%, 80%, 90%, 95%, 99%, 99.5% or 99.9%. Similarly, those compounds which increase product formation are considered to be ARP polypeptide enhancers or activators. For example, a test compound can increase product formation by at least two-fold, five-fold, ten-fold, 100-fold, 200-fold or 1000-fold. ARP polypeptide inhibitors and activators can then be subjected to further in vitro or in vivo testing to confirm that they inhibit an ARP polypeptide activity in cellular and animal models.

Suitable test compounds for the inhibition or enhancement assays can be any substance, molecule, compound, mixture of molecules or compounds, or any other composition which is suspected of being capable of inhibiting an ARP polypeptide activity in vivo or in vitro. The test compounds can be macromolecules, such as biological polymers, including proteins, polysaccharides and nucleic acid molecules. Sources of test compounds which can be screened for ARP polypeptide inhibitory activity include, for example, libraries of peptides, polypeptides, DNA, RNA and small organic compounds. The test compounds can be selected randomly and tested by the screening methods of the present invention. Test compounds are administered to the reaction system at a concentration in the range from about 1 pM to 1 mM.

Methods for producing pluralities of compounds to use in screening for compounds that modulate the activity of an ARP polypeptide, including chemical or biological molecules that are inhibitors or enhancers of an ARP activity such as simple or complex organic molecules, metal-containing compounds, carbohydrates, peptides, proteins, peptidomimetics, glycoproteins, lipoproteins, nucleic acid molecules, antibodies, and the like, are well known in the art and are described, for example, in Huse, U.S. Pat. No. 5,264,563; Francis et al., *Curr. Opin. Chem. Biol.*, 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233–1251 (1994); Gordon et al., *J. Med. Chem.* 37:1385–1401 (1994); Gordon et al., *Acc. Chem. Res.* 29:144–154 (1996); Wilson and Czarnik, eds., *Combinatorial Chemistry: Synthesis and Application*, John Wiley & Sons, New York (1997)).

Therefore, the invention provides a method of identifying a compound that inhibits or enhances an ARP polypeptide activity where the sample further consists of a prostate cell lysate, a recombinant cell lysate expressing an ARP polypeptide, an in vitro translation lysate containing an ARP mRNA, a fraction of a prostate cell lysate, a fraction of a recombinant cell lysate expressing an ARP polypeptide, a fractionated sample of an in vitro translation lysate containing an ARP mRNA or an isolated ARP polypeptide. The method can be performed in single or multiple sample format.

In another embodiment, polypeptides of the invention can be used as vaccines to prophylactically treat individuals for the occurrence of a prostate neoplastic condition or pathology. Such vaccines can be used to induce B or T cell immune responses or both aspects of the individuals endogenous immune mechanisms. The mode of administration and formulations to induce either or both of these immune responses are well known to those skilled in the art. For example, polypeptides can be administered in many possible formulations, including pharmaceutically acceptable mediums. They can be administered alone or, for example, in the case of a peptide, the peptide can be conjugated to a carrier, such as KLH, in order to increase its immunogenicity. The vaccine can include or be administered in conjunction with an adjuvant, various of which are known to those skilled in the art. After initial immunization with the vaccine, further boosters can be provided if desired. Therefore, the vaccines are administered by conventional methods in dosages which are sufficient to elicit an immunological response, which can be easily determined by those skilled in the art. Alternatively, the vaccines can contain anti-idiotypic antibodies which are internal images of polypeptides of the invention. Methods of making, selecting and administering such anti-idiotype vaccines are well known in the art. See, for example, Eichmann, et al., CRC Critical Reviews in Immunology 7:193–227 (1987). In addition, the vaccines can contain an ARP nucleic acid molecule. Methods for using nucleic acid molecules such as DNA as vaccines are well known to those skilled in the art (see, for example, Donnelly et al. (*Ann. Rev. Immunol.* 15:617–648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997)).

The invention additionally provides a method of treating or reducing the severity of a prostate neoplastic condition. The method is practiced by administering to an individual having a prostate neoplastic condition or other prostatic pathology an ARP1, ARP2, ARP3, ARP4 or ARP5 regulatory agent. A "regulatory agent" means an agent that inhibits or enhances a biological activity of the specified ARP polypeptide. Such an ARP regulatory agent can effect the amount of ARP polypeptide produced or can inhibit or enhance activity without effecting the amount of polypeptide. Such an ARP regulatory agent can be, for example, a dominant negative form of ARP1, ARP2, ARp3, Arp4 or Arp5; a ARP3, ARP4 or ARP selective binding agent, or an antisense molecule. One skilled in the art understands that such an ARP1, ARP2, ARP3, ARP4 or ARP5 regulatory agent can be an agent that selectively regulates a biological activity of the specified ARP polypeptide or, alternatively, can be a non-selective agent that, in addition to regulating a biological activity of the specified polypeptide, also regulates the activity of one or more polypeptides.

A ARP regulatory agent can cause a two-fold, five-fold, ten-fold, 20-fold, 100-fold or more reduction in the amount or activity of an ARP polypeptide. As another example, a regulatory agent can cause a two-fold, five-fold, ten-fold, 20-fold, 100-fold or more increase in the amount or activity of an ARP polypeptide or nucleic acid. ARP regulatory agents include ARP nucleic acid molecules, including antisense nucleic acid molecules, and other non-ARP nucleic acid molecules; binding agents including antibodies, and compounds identified by the methods described herein. Such regulatory agents can be useful as therapeutics for treating or reducing the severity of an individual with a prostate neoplastic condition or pathology.

One type of ARP regulatory agent is an inhibitor, means an agent effecting a decrease in the extent, amount or rate of ARP polypeptide expression or activity. An example of an ARP inhibitor is an ARP antisense nucleic acid molecule or a transcriptional inhibitor that binds to an ARP 5' promoter/regulatory region.

The term inhibitory amount means the amount of an inhibitor necessary to effect a reduction in the extent, amount or rate of ARP polypeptide. For example, an inhibitory amount of inhibitor can cause a two-fold, five-fold, ten-fold, 20-fold, 100-fold or more reduction in the amount or activity of an ARP polypeptide of the invention.

Such inhibitors can be produced using methods which are generally known in the art, and include the use of a purified ARP polypeptide to produce antibodies or to screen libraries of compounds, as described previously, for those which specifically bind a corresponding ARP polypeptide. For example, in one aspect, antibodies which are selective for an ARP polypeptide of the invention can be used directly as an antagonist, or indirectly as a targeting or delivery mechanism for bringing a cytotoxic or cytostatic agent to neoplastic prostate cells. Such agents can be, for example, radioisotopes. The antibodies can be generated using methods that are well known in the art and include, for example, polyclonal, monoclonal, chimeric, humanized single chain, Fab fragments, and fragments produced by a Fab expression library.

In another embodiment of the invention, ARP polynucleotides, or any fragment thereof, or antisense molecules, can be used as an ARP regulatory agent in a method of the invention. In one aspect, antisense molecules to an ARP encoding nucleic acid molecules can be used to block the transcription or translation of the corresponding mRNA. Specifically, cells can be transformed with sequences complementary to a nucleic acid molecule of the invention. Such methods are well known in the art, and sense or antisense oligonucleotides or larger fragments, can be designed from various locations along the coding or control regions of sequences encoding ARP polypeptides or nucleic acids. Thus, antisense molecules may be used to modulate an ARP activity, or to achieve regulation of an ARP gene function.

Expression vectors derived from retroviruses, adenovirus, adeno-associated virus (AAV), herpes or vaccinia viruses, or from various bacterial plasmids can be used for delivery of antisense nucleotide sequences to the prostate cell population. The viral vector selected should be able to infect the tumor cells and be safe to the host and cause minimal cell transformation. Retroviral vectors and adenoviruses offer an efficient, useful, and presently the best-characterized means of introducing and expressing foreign genes efficiently in mammalian cells. These vectors are well known in the art and have very broad host and cell type ranges, express genes stably and efficiently. Methods which are well known to those skilled in the art can be used to construct such recombinant vectors and are described in Sambrook et al., supra. Even in the absence of integration into the DNA, such vectors can continue to transcribe RNA molecules until they are disabled by endogenous nucleases. Transient expression can last for a month or more with a non-replicating vector and even longer if appropriate replication elements are part of the vector system.

Ribozymes, which are enzymatic RNA molecules, can also be used to catalyze the specific cleavage of an ARP mRNA. The mechanism of ribozyme action involves sequence-specific hybridization of the ribozyme molecule to complementary target ARP RNA, followed by endonucleolytic cleavage. Specific ribozyme cleavage sites within any potential RNA target are identified by scanning an ARP RNA for ribozyme cleavage sites which include the following sequences: GUA, GUU, and GUC. Once identified, short RNA sequences of between 15 and 20 ribonucleotides corresponding to the region of the target gene containing the cleavage site can be evaluated for secondary structural features which can render the oligonucleotide inoperable. The suitability of candidate targets can also be evaluated by testing accessibility to hybridization with complementary oligonucleotides using ribonuclease protection assays. Antisense molecules and ribozymes of the invention can be prepared by any method known in the art for the synthesis of nucleic acid molecules.

In another embodiment, an ARP promoter and regulatory region can be used for constructing vectors for prostate cancer gene therapy. The promoter and regulatory region can be fused to a therapeutic gene for prostate specific expression. This method can include the addition of one or more enhancer elements which amplify expression of the heterologous therapeutic gene without compromising tissue specificity. Methods for identifying a gene promoter and regulatory region are well known to those skilled in the art, for example, by selecting an appropriate primer from the 5' end of the coding sequence and isolating the promoter and regulatory region from genomic DNA.

Examples of therapeutic genes that are candidates for prostate gene therapy utilizing an ARP promoter include suicide genes. The expression of suicide genes produces a protein or agent that directly or indirectly inhibits neoplastic prostate cell growth or promotes neoplastic prostate cell death. Suicide genes include genes encoding enzymes, oncogenes, tumor suppressor genes, genes encoding toxins, genes encoding cytokines, or a gene encoding oncostatin. The therapeutic gene can be expressed using the vectors described previously for antisense expression.

In accordance with another embodiment of the present invention, there are provided diagnostic systems, for example, in kit form. Such a diagnostic system contains at least one nucleic acid molecule or antibody of the invention in a suitable packaging material. The diagnostic kits containing nucleic acid molecules are derived from ARP nucleic acid molecules described herein. A diagnostic system of the invention can be useful for assaying for the presence or absence of an ARP nucleic acid molecule in either genomic DNA or mRNA.

A suitable diagnostic system includes at least one ARP nucleic acid molecule or antibody, as a separately packaged chemical reagent(s) in an amount sufficient for at least one assay. For a diagnostic kit containing a nucleic acid molecule of the invention, the kit will generally contain two or more nucleic acid molecules. When the diagnostic kit is to be used in PCR, the kit can further contain at least two oligonucleotides that can serve as primers for PCR. Those of skill in the art can readily incorporate nucleic acid molecules antibodies of the invention into kit form in combination with appropriate buffers and solutions for the practice of the invention methods as described herein. A kit containing an ARP polypeptide-specific antibody can contain a reaction cocktail that provides the proper conditions for performing an assay, for example, an ELISA or other immunoassay, for determining the level of expression of a corresponding ARP polypeptide in a specimen, and can contain control samples that contain known amounts of a corresponding ARP polypeptide and, if desired, a second antibody selective for the corresponding anti-ARP antibody.

The contents of the kit of the invention, for example, ARP nucleic acid molecules or antibodies, are contained in packaging material, which can provide a sterile, contaminant-free environment. In addition, the packaging material contains instructions indicating how the materials within the kit can be employed both to detect the presence or absence of a particular nucleic acid sequence or polypeptide of the invention or to diagnose the presence of, or a predisposition for a condition associated with the presence or absence of a nucleic acid sequence or polypeptide of the invention such as prostate cancer. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

All journal article, reference, and patent citations provided above, in parentheses or otherwise, whether previously stated or not, are incorporated herein by reference.

It is understood that modifications which do not substantially affect the activity of the various embodiments of this invention are also included within the definition of the invention provided herein. Accordingly, the following examples are intended to illustrate but not limit the present invention.

EXAMPLE I

Isolation of ARP cDNA

This example describes the isolation of ARP1, ARP2, ARP3, ARP4 AND ARP5 cDNAs.

To identify genes transcriptionally regulated by androgens, microarrays containing prostate derived cDNAs were screened using RNA from a prostate cell line. Those RNAs showing increased expression levels in response to androgen stimulation were identified and characterized further. Specifically, the microarrays were constructed from a non-redundant set of 1500 prostate-derived cDNA clones identified from the Prostate Expression Database, a public sequence repository of expressed sequence tag (EST) data derived from human prostate cDNA libraries (Hawkins et al., *Nucleic Acids Res.* 27:204–208 (1999)). The 1500 prostate cDNA clones were selected from the Prostate Expression Database by randomly selecting the first 1500 non-redundant clones that were in the database. The 1500 prostate cDNA clones were randomly selected from the database using the criteria of taking the first 1500 non-redundant clones in the database and available based on their prior characterization as prostate-derived. Individual clones from the library were obtained and inserts were amplified using primers corresponding to priming sites flanking the insert cloning site of the pSport1 plasmid (Life Technologies, Germantown, Md.) as previously described by Nelson et al. (*Genomics* 47:12–25 (1998)). PCR products were purified through Sephacryl S500 (Pharmacia, Kalamazoo, Mich.), mixed 1:1 with denaturing Reagent D (Amersham, Piscataway, N.J.), and spotted in duplicate onto coated Type IV glass microscope slides (Amersham, Piscataway, N.J.) using a Molecular Dynamics (Sunnyvale, Calif.) Gen II robotic spotting tool. After spotting, the slides were air-dried and UV-crosslinked with 500 mJ of energy.

To identify genes transcriptionally regulated by androgens, the microarrays of prostate derived cDNAs were profiled using total RNA isolated from LNCaP cells cultured for 72 hours either in the presence or absence of the synthetic androgen R1881 (NEN Life Sciences Products, Boston, Mass.). Total RNA was prepared using TRIzol (Life Technologies, Germantown, Md.) according to the manufacturer's directions. The integrity of the RNA preparation was checked on a standard formaldehyde agarose gel. Fifty µg of the total RNA was digested with 1 µl of RNase-free DNase (Promega, Madison, Wis.) (1 µ/µl) in 1× first strand cDNA synthesis buffer (Gibco-BRL, Germantown, Md.) at 37° C. for 30 minutes. The reaction mix was then extracted with Phenol/chloroform (1:1) and RNA was precipitated with ethanol. The mRNA was isolated from the DNA-free total RNA using a Dynabeads mRNA purification kit (Dynal, Lake Success, N.Y.).

Fluorescence-labeled probes were constructed from the above-isolated mRNA as follows. Briefly, 1 µg polyA+ RNA or 30 µg total RNA in a reaction volume of 20 µl containing 1 µl anchored oligo-dT primer (Amersham, Piscataway, N.J.), 0.05 mM Cy3-dCTP (Amersham, Piscatawy, N.J.), 0.05 mM dCTP, 0.1 mM each dGTP, dATP, dTTP, and 200 U Superscript II reverse transcriptase (Life Technologies, Germantown, Md.) were incubated at 42° C. for 90 minutes followed by heating to 94° C. for 3 minutes. Unlabeled RNA was hydrolyzed by the addition of 1 µl of 5M NaOH and heating to 37° C. for 10 minutes. One µl of 5M HCl and 5 µl of 1 M Tris-HCl (pH 7.5) were added to neutralize the base. Unincorporated nucleotides and salts were removed by chromatography (Qiagen, Valencia, Calif.), and the cDNA was eluted in 30 µl distilled water.

Microarray hybridization was performed as follows. One µg of dA/dT 12–18 (Pharmacia, Kalamazoo, Mich.) and 1 µg of Cot1 DNA (Life Technologies, Germantown, Md.) were added to the probe, heat denatured at 94° C. for 5 minutes, combined with an equal volume of 2× microarray hybridization solution (Amersham, Piscataway, N.J.) and placed onto the microarray slide with a coverslip. Hybridization was carried out in a humid chamber at 52° C. for 16 hours. The slides were washed once with 1×SSC, 0.2% SDS at room temperature for 5 minutes, then twice washed with 0.1×SSC, 0.2% SDS at room temperature for 10 minutes. After washing, the slide was rinsed in distilled water to remove trace salts and dried.

Analysis of the microarray slides to identify androgen-regulated prostate genes was performed as follows. Fluorescence intensities of the immobilized targets were measured using a laser confocal microscope (Molecular Dynamics, Sunnyvale, Calif.). Intensity data were integrated at a pixel resolution of 10 micrometers using approximately 20 pixels per spot, and recorded at 16 bits. Local background hybridization signals were subtracted prior to comparing spot intensities and determining expression ratios. For each experiment, each cDNA was represented twice on each slide, and the experiments were performed in duplicate producing four data points per cDNA clone per hybridization probe. Intensity ratios for each cDNA clone hybridized with probes derived from androgen-stimulated LNCaP and androgen-starved LNCaP were calculated (stimulated intensity/starved intensity). A gene expression level change was treated as significantly different between the two conditions if all four replicate spots for a given cDNA demonstrated a ratio greater than 2 or less than ½ and the signal intensity was greater than 2 standard deviations above the image background. It had been determined previously that expression ratios less than 2-fold are not reproducible in this system.

Of a total of 1500 distinct cDNAs represented on the microarray, several were identified as giving a differential signal with the androgen-stimulated probe as compared to the non-stimulated probe.

Additional cDNA clones were obtained from screening human prostate 5' stretch cDNA (ClonTech, Inc.) With the original cDNA clones and sequences. RACE was performed using Marathon Ready human prostate cDNAs from Clon-Tech and using cDNA prepared from androgen-stimulated LNCaP cells with the Marathon cDNA amplification kit (ClonTech Inc.) according to manufacturer's protocol.

As shown in FIG. 1, the ARP1 cDNA has a nucleotide sequence of 1026 nucleotides. As shown in FIG. 2, ARP2 cDNA contains 4509 nucleotides predicted to encode a polypeptide 252 amino acids long. As shown in FIG. 3, ARP3 cDNA contains 2213 nucleotides predicted to encode a polypeptide 538 amino acids long.

The ARP4 cDNA was isolated as described above. RACE was performed using the following primers: RC55 (5'-TGAGGTATCCCAGAGCAAACACAAAGCAG-3'; SEQ ID NO: 10) and RC202 (5'-TCAGTTCTTCATCCTTCCGAAACATCCC-3'; SEQ ID NO: 11). RACE reactions were performed according to the standard ClonTech protocol, and the resulting nucleic acids sequenced by standard methods. Two related cDNAs were obtained derived from alternately spliced mRNAs. As shown in FIG. 4, ARP4 cDNA contains 4433 nucleotides predicted to encode a protein of 141 amino acids. ARP5 cDNA, shown in FIG. 5, contains 1276 nucleotides predicted to encode a protein of 425 amino acids. The alternate splice junction is at nucleotide 401 resulting in a relative frameshift in the mRNAs.

Expression analysis of ARP4 was performed using a multiple tissue Northern blot and a 5D6 probe containing nucleotides 1814 to 4433 of SEQ ID NO: 6. As shown in FIG. 6, ARP4 is most abundantly expressed in prostate, testis and ovary tissues.

SEQUENCE LISTING

<160> NUMBER OF SEQ ID NOS: 11

<210> SEQ ID NO 1
<211> LENGTH: 1026
<212> TYPE: DNA
<213> ORGANISM: Homo sapiens

<400> SEQUENCE: 1

```
tagtttgtat ttttcattac cagcaagggt aaacagttat ccatgaccca tttctatgtt     60
ctcgtggcat gcttccatgt actgcctctg catgcagcag gccacctcgg gcagagccta    120
aagcatgtga taaatgaaat gctatcacaa tacaggttgt gtctgaaaaa caaatggcaa    180
cttattatcc aagatcaatg aaggaaaaag caaatttact aaaatatttc tttatttgaa    240
taaggtcaat gccatttctt gaattccagc tagcatcaaa taatcaggaa aaaaaaaact    300
tgacaaaatg ttatccaatt gaaattgaca gtggatagaa aaccctttta aactttaagt    360
aatgtcataa aagaaatata ttaaacaagc aacagacaga tctaaaaagt tccaagtgtg    420
gatttcacat tagatcttat aaattaaaaa aatcctcaat ataatcattt gttcactatc    480
ttctttcaat aagcacatgg acagggaaag ataatcacac cttaatattc acaactgcta    540
tttgtgttct ttacaaaaat tgtatctctg caatgcagtg aggcaggcaa tcccttgttc    600
aagtcatttc tgttttccct aagttatcaa aaagtacaac tgtctgatat aaattgttac    660
cataatcaca atcaggaagg caaagaagct ttagcaggca ggcttgaaga tgggagtttt    720
catggcttga ccatgaatga tctcaagatg atttcataag attaaaagcc atcacgaaaa    780
tactgaaagc aacaggtaat aatctggatt cagtctgtag ttgctcatga accacgcgtt    840
ttaataaaag gaacattaag taaattgtag gtataaaaga atcagtgcat atctgttaat    900
gtcattgaca ataaaaatat attatcttct cagctcagct ctaaattaac aaaacaccta    960
tttttttttt cccactcctc attttagtgg ttctcaaaca ttggtgtgct cagaatctcc   1020
tgaggt                                                              1026
```

<210> SEQ ID NO 2
<211> LENGTH: 4527
<212> TYPE: DNA
<213> ORGANISM: Homo sapiens
<220> FEATURE:
<221> NAME/KEY: CDS
<222> LOCATION: (96)...(851)

<400> SEQUENCE: 2

```
tccttgggtt cgggtgaaag cgcctggggg ttcgtggcca tgatccccga gctgctggag     60
aactgaaggc ggacagtctc ctgcgaaacc aggca atg gcg gag ctg gag ttt       113
                                     Met Ala Glu Leu Glu Phe
                                      1               5 gtt cag atc atc atc atc gtg gtg gtg atg atg gtg atg gtg gtg gtg      161
Val Gln Ile Ile Ile Ile Val Val Val Met Met Val Met Val Val Val
               10                  15                  20 atc acg tgc ctg ctg agc cac tac aag ctg tct gca cgg tcc ttc atc      209
Ile Thr Cys Leu Leu Ser His Tyr Lys Leu Ser Ala Arg Ser Phe Ile
        25                  30                  35
```

```
agc cgg cac agc cag ggg cgg agg aga gaa gat gcc ctg tcc tca gaa    257
Ser Arg His Ser Gln Gly Arg Arg Arg Glu Asp Ala Leu Ser Ser Glu
     40                  45                  50 gga tgc ctg tgg ccc tcg gag agc aca gtg tca ggc aac gga atc cca    305
Gly Cys Leu Trp Pro Ser Glu Ser Thr Val Ser Gly Asn Gly Ile Pro
 55                  60                  65                  70 gag ccg cag gtc tac gcc ccg cct cgg ccc acc gac cgc ctg gcc gtg    353
Glu Pro Gln Val Tyr Ala Pro Pro Arg Pro Thr Asp Arg Leu Ala Val
                 75                  80                  85 ccg ccc ttc gcc cag cgg gag cgc ttc cac cgc ttc cag ccc acc tat    401
Pro Pro Phe Ala Gln Arg Glu Arg Phe His Arg Phe Gln Pro Thr Tyr
             90                  95                 100 ccg tac ctg cag cac gag atc gac ctg cca ccc acc atc tcg ctg tca    449
Pro Tyr Leu Gln His Glu Ile Asp Leu Pro Pro Thr Ile Ser Leu Ser
            105                 110                 115 gac ggg gag gag ccc cca ccc tac cag ggc ccc tgc acc ctc cag ctt    497
Asp Gly Glu Glu Pro Pro Pro Tyr Gln Gly Pro Cys Thr Leu Gln Leu
        120                 125                 130 cgg gac ccc gag cag cag ctg gaa ctg aac cgg gag tcg gtg cgc gca    545
Arg Asp Pro Glu Gln Gln Leu Glu Leu Asn Arg Glu Ser Val Arg Ala
135                 140                 145                 150 ccc cca aac aga acc atc ttc gac agt gac ctg atg gat agt gcc agg    593
Pro Pro Asn Arg Thr Ile Phe Asp Ser Asp Leu Met Asp Ser Ala Arg
                155                 160                 165 ctg ggc ggc ccc tgc ccc ccc agc agt aac tcg ggc atc agc gcc acg    641
Leu Gly Gly Pro Cys Pro Pro Ser Ser Asn Ser Gly Ile Ser Ala Thr
            170                 175                 180 tgc tac ggc agc ggc ggg cgc atg gag ggg ccg ccg ccc acc tac agc    689
Cys Tyr Gly Ser Gly Gly Arg Met Glu Gly Pro Pro Pro Thr Tyr Ser
        185                 190                 195 gag gtc atc ggc cac tac ccg ggg tcc tcc ttc cag cac cag cag agc    737
Glu Val Ile Gly His Tyr Pro Gly Ser Ser Phe Gln His Gln Gln Ser
    200                 205                 210 agt ggg ccg ccc tcc ttg ctg gag ggg acc cgg ctc cac cac aca cac    785
Ser Gly Pro Pro Ser Leu Leu Glu Gly Thr Arg Leu His His Thr His
215                 220                 225                 230 atc gcg ccc cta gag agc gca gcc atc tgg agc aaa gag aag gat aaa    833
Ile Ala Pro Leu Glu Ser Ala Ala Ile Trp Ser Lys Glu Lys Asp Lys
                235                 240                 245 cag aaa gga cac cct ctc tagggtcccc agggggggccg ggctggggct          881
Gln Lys Gly His Pro Leu
                250 gcgtaggtga aaaggcagaa cactccgcgc ttcttagaag aggagtgaga ggaaggcggg    941 gggcgcagca acgcatcgtg tggccctccc ctcccacctc cctgtgtata aatatttaca   1001 tgtgatgtct ggtctgaatg cacaagctaa gagagcttgc aaaaaaaaaa agaaaaaaga   1061 aaaaaaaaaa ccacgtttct tgttgagct gtgtcttgaa ggcaaagaa aaaaaatttc     1121 tacagtagtc tttcttgttt ctagttgagc tgcgtgcgtg aatgcttatt ttcttttgtt   1181 tatgataatt tcacttaact ttaaagacat atttgcacaa aacctttgtt taaagatctg   1241 caatattata tataaaata tatataagat aagagaaact gtatgtgcga gggcaggagt    1301 atttttgtat tagaagaggc ctattaaaaa aaaagttgt tttctgaact agaagaggaa    1361 aaaaatggca atttttgagt gccaagtcag aaagtgtgta ttaccttgta aagaaaaaaa   1421 ttacaaagca ggggtttaga gttattata taaatgttga gattttgcac tattttttaa    1481 tataaatatg tcagtgcttg cttgatggaa acttctcttg tgtctgttga gactttaagg   1541
```

```
gagaaatgtc ggaatttcag agtcgcctga cggcagaggg tgagccccg tggagtctgc      1601 agagaggcct tggccaggag cggcgggctt tcccgagggg ccactgtccc tgcagagtgg      1661
atgcttctgc ctagtgacag gttatcacca cgttatatat tccctaccga aggagacacc      1721 ttttccccc tgacccagaa cagcctttaa atcacaagca aaataggaaa gttaaccacg      1781
gaggcaccga gttccaggta gtggttttgc ctttcccaaa aatgaaaata aactgttacc      1841
gaaggaatta gtttttcctc ttcttttttc caactgtgaa ggtccccgtg gggtggagca      1901
tggtgcccct cacaagccgc agcggctggt gcccgggcta ccagggacat gccagagggc      1961
tcgatgactt gtctctgcag ggcgctttgg tggttgttca gctggctaaa ggttcaccgg      2021
tgaaggcagg tgcggtaact gccgcactgg accctaggaa gccccaggta ttcgcaatct      2081
gacctcctcc tgtctgtttc ccttcacgga tcaattctca cttaagaggc caataaacaa      2141
cccaacatga aaggtgaca agcctgggtt tctcccagga taggtgaaag ggttaaaatg      2201
agtaaagcag ttgagcaaac accaacccga gcttcgggcg cagaattctt caccttctct      2261 tccccttttcc atctcctttc cccgcggaaa caacgcttcc cttctggtgt gtctgttgat      2321
ctgtgttttc atttacatct ctcttagact ccgctcttgt tctccaggtt ttcaccagat      2381
agatttgggg ttggcgggac ctgctggtga cgtgcaggtg aaggacagga aggggcatgt      2441
gagcgtaaat agaggtgacc agaggagagc atgagggtg gggctttggg acccaccggg      2501
gccagtggct ggagcttgac gtctttcctc cccatggggg tgggagggcc cccagctgga      2561
agagcagact cccagctgct accccctccc ttcccatggg agtggctttc cattttgggc      2621
agaatgctga ctagtagact aacataaaag atataaaagg caataactat tgtttgtgag      2681 caacttttt ataacttcca aaacaaaaac ctgagcacag ttttgaagtt ctagccactc      2741
gagctcatgc atgtgaaacg tgtgctttac gaaggtggca gctgacagac gtgggctctg      2801
catgccgcca gcctagtaga aagttctcgt tcattggcaa cagcagaacc tgcctctccg      2861
tgaagtcgtc agcctaaaat ttgtttctct cttgaagagg attctttgaa aaggtcctgc      2921
agagaaatca gtacaggtta tcccgaaagg tacaaggacg cacttgtaaa gatgattaaa      2981
acgtatcttt cctttatgtg acgcgtctct agtgccttac tgaagaagca gtgacactcc      3041
cgtcgctcgg tgaggacgtt cccggacagt gcctcactca cctgggactg gtatcccctc      3101
ccagggtcca ccaagggctc ctgcttttca gacacccat catcctcgcg cgtcctcacc      3161
ctgtctctac cagggaggtg cctagctggg tgaggttact cctgctcctc caacctttt      3221 ttgccaaggt ttgtacacga ctcccatcta ggctgaaaac ctagaagtgg accttgtgtg      3281
tgtgcatggt gtcagcccaa agccaggctg agacagtcct catatcctct tgagccaaac      3341
tgtttgggtc tcgttgcttc atggtatggt ctggatttgt gggaatggct ttgcgtgaga      3401
aaggggagga gagtggttgc tgccctcagc cggcttgagg acagagcctg tccctctcat      3461
gacaactcag tgttgaagcc cagtgtcctc agcttcatgt ccagtggatg gcagaagttc      3521
atggggtagt ggcctctcaa aggctgggcg catcccaaga cagccagcag gttgtctctg      3581
gaaacgacca gagttaagct ctcggcttct ctgctgaggg tgcacccttt cctctagatg      3641
gtagttgtca cgttatcttt gaaaactctt ggactgctcc tgaggaggcc ctcttttcca      3701
gtaggaagtt agatggggt tctcagaagt ggctgattgg aagggacaa gcttcgtttc      3761 agggtctgc cgttccatcc tggttcagag aaggccgagc gtggctttct ctagccttgt      3821
cactgtctcc ctgcctgtca atcaccacct ttccyccaga ggaggaaaat tatctcccct      3881
gcaaagcccg gttctacaca gatttcacaa attgtgctaa gaaccgtccg tgttctcaga      3941
```

-continued

```
aagcccagtg ttttttgcaaa gaatgaaaag ggaccccata tgtagcaaaa atcagggctg    4001
ggggagagcc gggttcattc cctgtcctca ttggtcgtcc ctatgaattg tacgtttcag    4061
agaaattttt tttcctatgt gcaacacgaa gcttccagaa ccataaaata tcccgtcgat    4121
aaggaaagaa aatgtcgttg ttgttgtttt tctggaaact gcttgaaatc ttgctgtact    4181
atagagctca gaaggacaca gcccgtcctc ccctgcctgc ctgattccat ggctgttgtg    4241
ctgattccaa tgctttcacg ttggttcctg gcgtgggaac tgctctcctt tgcagcccca    4301
tttcccaagc tctgttcaag ttaaacttat gtaagctttc cgtggcatgc ggggcgcgca    4361
cccacgtccc cgctgcgtaa gactctgtat ttggatgcca atccacaggc ctgaagaaac    4421
tgcttgttgt gtatcagtaa tcattagtgg caatgatgac attctgaaaa gctgcaatac    4481
ttatacaata aattttacaa ttctttggaa aaaaaaaaaa aaaaaa                    4527
```

<210> SEQ ID NO 3
<211> LENGTH: 252
<212> TYPE: PRT
<213> ORGANISM: Homo sapiens

<400> SEQUENCE: 3

```
Met Ala Glu Leu Glu Phe Val Gln Ile Ile Ile Val Val Val Met
 1               5                  10                  15

Met Val Met Val Val Ile Thr Cys Leu Leu Ser His Tyr Lys Leu
                20                  25                  30

Ser Ala Arg Ser Phe Ile Ser Arg His Ser Gln Gly Arg Arg Glu
            35                  40                  45

Asp Ala Leu Ser Ser Glu Gly Cys Leu Trp Pro Ser Glu Ser Thr Val
50                  55                  60

Ser Gly Asn Gly Ile Pro Glu Pro Gln Val Tyr Ala Pro Pro Arg Pro
65                  70                  75                  80

Thr Asp Arg Leu Ala Val Pro Pro Phe Ala Gln Arg Glu Arg Phe His
                85                  90                  95

Arg Phe Gln Pro Thr Tyr Pro Tyr Leu Gln His Glu Ile Asp Leu Pro
            100                 105                 110

Pro Thr Ile Ser Leu Ser Asp Gly Glu Glu Pro Pro Tyr Gln Gly
        115                 120                 125

Pro Cys Thr Leu Gln Leu Arg Asp Pro Glu Gln Gln Leu Glu Leu Asn
130                 135                 140

Arg Glu Ser Val Arg Ala Pro Pro Asn Arg Thr Ile Phe Asp Ser Asp
145                 150                 155                 160

Leu Met Asp Ser Ala Arg Leu Gly Gly Pro Cys Pro Pro Ser Ser Asn
                165                 170                 175

Ser Gly Ile Ser Ala Thr Cys Tyr Gly Ser Gly Arg Met Glu Gly
            180                 185                 190

Pro Pro Pro Thr Tyr Ser Glu Val Ile Gly His Tyr Pro Gly Ser Ser
        195                 200                 205

Phe Gln His Gln Gln Ser Ser Gly Pro Pro Ser Leu Leu Glu Gly Thr
210                 215                 220

Arg Leu His His Thr His Ile Ala Pro Leu Glu Ser Ala Ala Ile Trp
225                 230                 235                 240

Ser Lys Glu Lys Asp Lys Gln Lys Gly His Pro Leu
                245                 250
```

<210> SEQ ID NO 4

```
<211> LENGTH: 2213
<212> TYPE: DNA
<213> ORGANISM: Homo sapiens
<220> FEATURE:
<221> NAME/KEY: CDS
<222> LOCATION: (1)...(1611)
<221> NAME/KEY: misc_feature
<222> LOCATION: (1)...(2213)
<223> OTHER INFORMATION: Xaa=any amino acid

<400> SEQUENCE: 4
```

| | | | | | | | | | | | | | | | | |
|---|---|---|---|---|---|---|---|---|---|---|---|---|---|---|---|---|
| ggg | ggg | ctg | aca | aca | act | gtg | ata | ggt | acg | agg | ctg | ggt | gtg | gat | cgg | 48 |
| Gly | Gly | Leu | Thr | Thr | Thr | Val | Ile | Gly | Thr | Arg | Leu | Gly | Val | Asp | Arg | |
| 1 | | | | 5 | | | | | 10 | | | | | 15 | | |
| ccg | agg | ctc | tcc | tgg | agc | gct | ggg | cct | tcg | ctg | gcc | gca | ccg | gca | gcc | 96 |
| Pro | Arg | Leu | Ser | Trp | Ser | Ala | Gly | Pro | Ser | Leu | Ala | Ala | Pro | Ala | Ala | |
| | | | 20 | | | | | 25 | | | | | 30 | | | |
| atg | agc | tcg | gag | atg | gag | ccg | ctg | ctc | ctg | gcc | tgg | agc | tat | ttt | agg | 144 |
| Met | Ser | Ser | Glu | Met | Glu | Pro | Leu | Leu | Leu | Ala | Trp | Ser | Tyr | Phe | Arg | |
| | | 35 | | | | | 40 | | | | | 45 | | | | |
| cgc | agg | aag | ttc | cag | ctc | tgc | gcc | gat | cta | tgc | acg | cag | atg | ctg | gag | 192 |
| Arg | Arg | Lys | Phe | Gln | Leu | Cys | Ala | Asp | Leu | Cys | Thr | Gln | Met | Leu | Glu | |
| | 50 | | | | | 55 | | | | | 60 | | | | | |
| aag | tcc | cct | tat | gac | cag | gca | gct | tgg | atc | tta | aaa | gca | aga | gcg | cta | 240 |
| Lys | Ser | Pro | Tyr | Asp | Gln | Ala | Ala | Trp | Ile | Leu | Lys | Ala | Arg | Ala | Leu | |
| 65 | | | | | 70 | | | | | 75 | | | | | 80 | |
| aca | gaa | atg | gta | tac | ata | gat | gaa | att | gat | gta | gat | cag | gaa | gga | att | 288 |
| Thr | Glu | Met | Val | Tyr | Ile | Asp | Glu | Ile | Asp | Val | Asp | Gln | Glu | Gly | Ile | |
| | | | | 85 | | | | | 90 | | | | | 95 | | |
| gca | gaa | atg | atg | ctg | gat | gaa | aat | gct | ata | gct | caa | gtt | cca | cgc | cct | 336 |
| Ala | Glu | Met | Met | Leu | Asp | Glu | Asn | Ala | Ile | Ala | Gln | Val | Pro | Arg | Pro | |
| | | | 100 | | | | | 105 | | | | | 110 | | | |
| gga | acg | tct | ttg | aaa | ctc | cct | gga | act | aat | cag | aca | gga | ggg | cct | agc | 384 |
| Gly | Thr | Ser | Leu | Lys | Leu | Pro | Gly | Thr | Asn | Gln | Thr | Gly | Gly | Pro | Ser | |
| | | 115 | | | | | 120 | | | | | 125 | | | | |
| cag | gcc | gtt | agg | cca | atc | aca | caa | gct | gga | aga | ccc | att | aca | ggt | ttc | 432 |
| Gln | Ala | Val | Arg | Pro | Ile | Thr | Gln | Ala | Gly | Arg | Pro | Ile | Thr | Gly | Phe | |
| | 130 | | | | | 135 | | | | | 140 | | | | | |
| ctc | agg | ccc | agc | acg | cag | agt | gga | agg | cca | ggc | act | atg | gaa | cag | gct | 480 |
| Leu | Arg | Pro | Ser | Thr | Gln | Ser | Gly | Arg | Pro | Gly | Thr | Met | Glu | Gln | Ala | |
| 145 | | | | | 150 | | | | | 155 | | | | | 160 | |
| atc | aga | aca | ccc | aga | acc | gcc | tac | aca | gcc | cgc | cct | atc | acc | agc | tcc | 528 |
| Ile | Arg | Thr | Pro | Arg | Thr | Ala | Tyr | Thr | Ala | Arg | Pro | Ile | Thr | Ser | Ser | |
| | | | | 165 | | | | | 170 | | | | | 175 | | |
| tcc | gga | aga | ttt | gtc | agg | ctg | gga | acg | gct | tcc | atg | ctt | aca | agt | cct | 576 |
| Ser | Gly | Arg | Phe | Val | Arg | Leu | Gly | Thr | Ala | Ser | Met | Leu | Thr | Ser | Pro | |
| | | | 180 | | | | | 185 | | | | | 190 | | | |
| gat | gga | cca | ttt | ata | aat | tta | tct | agg | ctg | aat | tta | aca | aag | tat | tcc | 624 |
| Asp | Gly | Pro | Phe | Ile | Asn | Leu | Ser | Arg | Leu | Asn | Leu | Thr | Lys | Tyr | Ser | |
| | | 195 | | | | | 200 | | | | | 205 | | | | |
| cag | aaa | cct | aag | ttg | gca | aag | gct | tgt | ttg | agt | ata | tct | ttc | atc | atg | 672 |
| Gln | Lys | Pro | Lys | Leu | Ala | Lys | Ala | Cys | Leu | Ser | Ile | Ser | Phe | Ile | Met | |
| | 210 | | | | | 215 | | | | | 220 | | | | | |
| aaa | atg | atg | tta | aga | ctg | ctt | tgg | atc | tgg | ctg | gcc | ctc | tcc | aca | gaa | 720 |
| Lys | Met | Met | Leu | Arg | Leu | Leu | Trp | Ile | Trp | Leu | Ala | Leu | Ser | Thr | Glu | |
| 225 | | | | | 230 | | | | | 235 | | | | | 240 | |
| cat | tct | cag | tac | aag | gac | tgg | tgg | tgg | aaa | gta | cag | att | gga | aaa | tgt | 768 |
| His | Ser | Gln | Tyr | Lys | Asp | Trp | Trp | Trp | Lys | Val | Gln | Ile | Gly | Lys | Cys | |
| | | | | 245 | | | | | 250 | | | | | 255 | | |
| tac | tac | agg | ttg | gga | atg | tat | cgt | gaa | gca | gaa | aaa | cag | ttt | aaa | tca | 816 |
| Tyr | Tyr | Arg | Leu | Gly | Met | Tyr | Arg | Glu | Ala | Glu | Lys | Gln | Phe | Lys | Ser | |
| | | | 260 | | | | | 265 | | | | | 270 | | | |

-continued

```
gcc ctg aag cag cag gaa atg gta gat aca ttt ctg tac ttg gca aaa        864
Ala Leu Lys Gln Gln Glu Met Val Asp Thr Phe Leu Tyr Leu Ala Lys
            275                 280                 285 gtt tat gtc tca ttg gat caa cct gtg act gct tta aat ctt ttc aaa        912
Val Tyr Val Ser Leu Asp Gln Pro Val Thr Ala Leu Asn Leu Phe Lys
        290                 295                 300 caa ggc tta gat aag ttt cca gga gaa gta acc ctg ctc tgt gga att        960
Gln Gly Leu Asp Lys Phe Pro Gly Glu Val Thr Leu Leu Cys Gly Ile
305                 310                 315                 320 gca aga atc tat gag gaa atg aac aat atg tca tca gca gca gaa tat       1008
Ala Arg Ile Tyr Glu Glu Met Asn Asn Met Ser Ser Ala Ala Glu Tyr
                325                 330                 335 tac aaa gaa gtt ttg aaa caa gac aat act cat gtg gra gcc atc gca       1056
Tyr Lys Glu Val Leu Lys Gln Asp Asn Thr His Val Xaa Ala Ile Ala
            340                 345                 350 tgc att gga agc aac cac ttc tat tct gat cag cca gaa ata gct ctc       1104
Cys Ile Gly Ser Asn His Phe Tyr Ser Asp Gln Pro Glu Ile Ala Leu
        355                 360                 365 cgg ttt tac agg cgg ctg ctg cag atg ggc att tat aac ggc cag ctt       1152
Arg Phe Tyr Arg Arg Leu Leu Gln Met Gly Ile Tyr Asn Gly Gln Leu
370                 375                 380 ttt aac aat ctg ggg ctg tgt tgc ttc tat gcc cag cag tat gat atg       1200
Phe Asn Asn Leu Gly Leu Cys Cys Phe Tyr Ala Gln Gln Tyr Asp Met
385                 390                 395                 400 act ctg acc tca ttt gaa cgt gcc ctt tct ttg gct gaa aat gaa gaa       1248
Thr Leu Thr Ser Phe Glu Arg Ala Leu Ser Leu Ala Glu Asn Glu Glu
                405                 410                 415 gag gca gct gat gtc tgg tac aac ttg gga cat gta gct gtg gga ata       1296
Glu Ala Ala Asp Val Trp Tyr Asn Leu Gly His Val Ala Val Gly Ile
            420                 425                 430 gga gat aca aat ttg gcc cat cag tgc ttc agg ctg gct ctg gtc aac       1344
Gly Asp Thr Asn Leu Ala His Gln Cys Phe Arg Leu Ala Leu Val Asn
        435                 440                 445 aac aac aac cac gcc gag gcc tac aac aac ctg gct gtg ctg gag atg       1392
Asn Asn Asn His Ala Glu Ala Tyr Asn Asn Leu Ala Val Leu Glu Met
450                 455                 460 cgg aag ggc cac gtt gaa cag gca agg gca cta tta caa act gca tca       1440
Arg Lys Gly His Val Glu Gln Ala Arg Ala Leu Leu Gln Thr Ala Ser
465                 470                 475                 480 tca tta gca ccc cat atg tat gaa ccg cat ttt aat ttt gca aca atc       1488
Ser Leu Ala Pro His Met Tyr Glu Pro His Phe Asn Phe Ala Thr Ile
                485                 490                 495 tct gat aag att gga gat ctg cag aga agc tat gtt gct gcg cag aag       1536
Ser Asp Lys Ile Gly Asp Leu Gln Arg Ser Tyr Val Ala Ala Gln Lys
            500                 505                 510 tct gaa gca gca ttt cca gac cat gtg gac aca caa cat tta att aaa       1584
Ser Glu Ala Ala Phe Pro Asp His Val Asp Thr Gln His Leu Ile Lys
        515                 520                 525 caa tta agg cag cat ttt gct atg ctc tgattgttcc ttagaccaca            1631
Gln Leu Arg Gln His Phe Ala Met Leu
530                 535 tatgttctta tgaagcagca ttatgcaagg ggaaaaaagc actatgtctg tgtatgtatg     1691
tatatagtgt aatacgtata ttttaacaaa cctgtccttg atattagtta aggtgacaca     1751
taagggtgac acagaatgtg taatgcaaat tcatagtaa tagtaactttt ataaaataat    1811 attataaaat acaggattta aacctttcta aatagatcct gaaactgtct ctcacattat    1871
atagtagatg tttgtttata atgtttacaa aacattttgg tgaatttcct caatgtttta    1931
```

-continued

```
taaatgtaca tttttttaagt ccttaagctg actcttagcc atcatgtagc ttaaggagtc    1991
tgaaatctgc cattaaaact gcacctttaa gccaggtgtg gtagcatgtg cctatagtcc    2051
cagctacttg ggaggtggag gtgggaggat tataaataga gactttcctt aagactttaa    2111
aaatgtattt aaaactattt tttattaaat actttgtgat ttcctattaa gctttaaaat    2171
aaatcattgt gtaaaacacc atcaaagcga taagctctgt aa                      2213
```

<210> SEQ ID NO 5
<211> LENGTH: 537
<212> TYPE: PRT
<213> ORGANISM: Homo sapiens
<220> FEATURE:
<221> NAME/KEY: VARIANT
<222> LOCATION: (1)...(537)
<223> OTHER INFORMATION: Xaa = Any Amino Acid

<400> SEQUENCE: 5

```
Gly Gly Leu Thr Thr Thr Val Ile Gly Thr Arg Leu Gly Val Asp Arg
  1               5                  10                  15

Pro Arg Leu Ser Trp Ser Ala Gly Pro Ser Leu Ala Ala Pro Ala Ala
             20                  25                  30

Met Ser Ser Glu Met Glu Pro Leu Leu Leu Ala Trp Ser Tyr Phe Arg
         35                  40                  45

Arg Arg Lys Phe Gln Leu Cys Ala Asp Leu Cys Thr Gln Met Leu Glu
 50                  55                  60

Lys Ser Pro Tyr Asp Gln Ala Ala Trp Ile Leu Lys Ala Arg Ala Leu
 65                  70                  75                  80

Thr Glu Met Val Tyr Ile Asp Glu Ile Asp Val Asp Gln Glu Gly Ile
                 85                  90                  95

Ala Glu Met Met Leu Asp Glu Asn Ala Ile Ala Gln Val Pro Arg Pro
            100                 105                 110

Gly Thr Ser Leu Lys Leu Pro Gly Thr Asn Gln Thr Gly Gly Pro Ser
        115                 120                 125

Gln Ala Val Arg Pro Ile Thr Gln Ala Gly Arg Pro Ile Thr Gly Phe
    130                 135                 140

Leu Arg Pro Ser Thr Gln Ser Gly Arg Pro Gly Thr Met Glu Gln Ala
145                 150                 155                 160

Ile Arg Thr Pro Arg Thr Ala Tyr Thr Ala Arg Pro Ile Thr Ser Ser
                165                 170                 175

Ser Gly Arg Phe Val Arg Leu Gly Thr Ala Ser Met Leu Thr Ser Pro
            180                 185                 190

Asp Gly Pro Phe Ile Asn Leu Ser Arg Leu Asn Leu Thr Lys Tyr Ser
        195                 200                 205

Gln Lys Pro Lys Leu Ala Lys Ala Cys Leu Ser Ile Ser Phe Ile Met
    210                 215                 220

Lys Met Met Leu Arg Leu Leu Trp Ile Trp Leu Ala Leu Ser Thr Glu
225                 230                 235                 240

His Ser Gln Tyr Lys Asp Trp Trp Lys Val Gln Ile Gly Lys Cys
                245                 250                 255

Tyr Tyr Arg Leu Gly Met Tyr Arg Glu Ala Glu Lys Gln Phe Lys Ser
            260                 265                 270

Ala Leu Lys Gln Gln Glu Met Val Asp Thr Phe Leu Tyr Leu Ala Lys
        275                 280                 285

Val Tyr Val Ser Leu Asp Gln Pro Val Thr Ala Leu Asn Leu Phe Lys
    290                 295                 300
```

-continued

```
Gln Gly Leu Asp Lys Phe Pro Gly Glu Val Thr Leu Leu Cys Gly Ile
305                 310                 315                 320

Ala Arg Ile Tyr Glu Glu Met Asn Asn Met Ser Ser Ala Ala Glu Tyr
            325                 330                 335

Tyr Lys Glu Val Leu Lys Gln Asp Asn Thr His Val Xaa Ala Ile Ala
        340                 345                 350

Cys Ile Gly Ser Asn His Phe Tyr Ser Asp Gln Pro Glu Ile Ala Leu
    355                 360                 365

Arg Phe Tyr Arg Arg Leu Leu Gln Met Gly Ile Tyr Asn Gly Gln Leu
370                 375                 380

Phe Asn Asn Leu Gly Leu Cys Cys Phe Tyr Ala Gln Gln Tyr Asp Met
385                 390                 395                 400

Thr Leu Thr Ser Phe Glu Arg Ala Leu Ser Leu Ala Glu Asn Glu Glu
                405                 410                 415

Glu Ala Ala Asp Val Trp Tyr Asn Leu Gly His Val Ala Val Gly Ile
            420                 425                 430

Gly Asp Thr Asn Leu Ala His Gln Cys Phe Arg Leu Ala Leu Val Asn
        435                 440                 445

Asn Asn Asn His Ala Glu Ala Tyr Asn Leu Ala Val Leu Glu Met
    450                 455                 460

Arg Lys Gly His Val Glu Gln Ala Arg Ala Leu Leu Gln Thr Ala Ser
465                 470                 475                 480

Ser Leu Ala Pro His Met Tyr Glu Pro His Phe Asn Phe Ala Thr Ile
                485                 490                 495

Ser Asp Lys Ile Gly Asp Leu Gln Arg Ser Tyr Val Ala Ala Gln Lys
            500                 505                 510

Ser Glu Ala Ala Phe Pro Asp His Val Asp Thr Gln His Leu Ile Lys
        515                 520                 525

Gln Leu Arg Gln His Phe Ala Met Leu
    530                 535

<210> SEQ ID NO 6
<211> LENGTH: 4433
<212> TYPE: DNA
<213> ORGANISM: Homo sapiens
<220> FEATURE:
<221> NAME/KEY: CDS
<222> LOCATION: (1)...(423)

<400> SEQUENCE: 6 ata gga gtg gag aac atg cac aat tac tgc ttt gtg ttt gct ctg gga      48
Ile Gly Val Glu Asn Met His Asn Tyr Cys Phe Val Phe Ala Leu Gly
1               5                   10                  15 tac ctc aca gtg tgc caa gtt act cga gtc tat atc ttt gac tat gga     96
Tyr Leu Thr Val Cys Gln Val Thr Arg Val Tyr Ile Phe Asp Tyr Gly
            20                  25                  30 caa tat tct gct gat ttt tca ggc cca atg atg atc att act cag aag    144
Gln Tyr Ser Ala Asp Phe Ser Gly Pro Met Met Ile Ile Thr Gln Lys
        35                  40                  45 atc act agt ttg gct tgc gaa ata cat gat ggg atg ttt cgg aag gat    192
Ile Thr Ser Leu Ala Cys Glu Ile His Asp Gly Met Phe Arg Lys Asp
    50                  55                  60 gaa gaa ctg act tcc tca cag agg gat tta gct gta agg cgc atg cca    240
Glu Glu Leu Thr Ser Ser Gln Arg Asp Leu Ala Val Arg Arg Met Pro
65                  70                  75                  80 agc tta ctg gag tat ttg agt tac aac tgt aac ttc atg ggg atc ctg    288
Ser Leu Leu Glu Tyr Leu Ser Tyr Asn Cys Asn Phe Met Gly Ile Leu
                85                  90                  95
```

| | | |
|---|---|---|
| gca ggc cca ctt tgc tct tac aaa gac tac att act ttc att gaa ggc<br>Ala Gly Pro Leu Cys Ser Tyr Lys Asp Tyr Ile Thr Phe Ile Glu Gly<br>100 105 110 | | 336 |
| aga tca tac cat atc aca caa tct ggt gaa aat gga aaa gaa gag aca<br>Arg Ser Tyr His Ile Thr Gln Ser Gly Glu Asn Gly Lys Glu Glu Thr<br>115 120 125 | | 384 |
| cag tat gaa aga aca gag cca tct cca aat gta agg tca tgagatttat<br>Gln Tyr Glu Arg Thr Glu Pro Ser Pro Asn Val Arg Ser<br>130 135 140 | | 433 |
| ctggagcctt tacagcatgt attgactgcg gktgttcaga agctcttagt ttgtgggctg | | 493 |
| tccttgttat ttcacttgac catctgtaca acattacctg tggagtacaa cattgatgag | | 553 |
| cattttcaag ctacagcttc gtggccaaca aagattatct atctgtatat ctctcttttg | | 613 |
| gctgccagac ccaaatacta ttttgcatgg acgctagctg actgccatwa ataatgctgc | | 673 |
| aggctttggt ttcagagggt atgacgaaaa tggagcagct cgctgggact taatttccaa | | 733 |
| tttgagaatt caacaaatag atgtcaac aagtttcaag atgtttcttg ataattggaa | | 793 |
| tattcagaca gctctttggc tcaaaaggtg cgttccttca aaaacgatct ttagatgtgc | | 853 |
| tttggcgtct agttctcgag gttgagcttc attgagttca ggttcttgat taaattaacg | | 913 |
| gtgttgagtg acattgtgac ctcagtgtca gccgggaaac actgttagcc tcctcctaag | | 973 |
| caagtcagta tcgaatgaga actattttgg cttgagtcac gaatgcagct atcctgcagg | | 1033 |
| tgcagctatc ctgccctctc aagcctcctt taaaggcctc tgccaatgtc agaggtcacc | | 1093 |
| agtatcctcc tttgcagctc ctgattgtgt tcagtagaga tgtggtttaa attaacaagt | | 1153 |
| gcctgcacaa gcacagtact tatgcctggg tactccagaa cagtcctggt tttaaatatt | | 1213 |
| tcaattcaac aaatcttkat ttgttaggca agggaaacaa acatgagtaa gataaaaaga | | 1273 |
| ctcagctcct gaaagtgaaa gagttcacaa ttttattaaa gacacggtgg tgtaatcaga | | 1333 |
| cacatgctgt tccctgtggt gaggatgagg agagagaaag caggaacagc gagggcacag | | 1393 |
| agggatgcgg gaagaacttc ctacaagtgt gggtgcttga gctgaggttt gtgtcaggag | | 1453 |
| cgtgtctcgt gaacagggca aggtagaggc aagccaggct gggtggagta acaggtgcga | | 1513 |
| aggacagagc tggggaacag cacactctcc caggggttct cttatcgtcc ctgtgagcac | | 1573 |
| attgccctat cttgaattta cttcataaaa acggcccct ataacgatac ggtgataagc | | 1633 |
| agccttttt tatagtgtcc ttttttaaat gacaaattaa acatctttat cccttgagat | | 1693 |
| ggctagcata cgctgtcatc tcttcacagt gcctggcagt ctccccagtg gctgcagatc | | 1753 |
| ctctgagcta atctgttgtg ttatttttg ttattgttat aatttaaatt tgataccta | | 1813 |
| ggggaaactt tattttcagc tgagttctct atccctgtca tagaagaatt gtagactaag | | 1873 |
| cacagtctat ctgccggaag gagtagtgtt attaggtcag ttgaaagtta ttgatttttt | | 1933 |
| ttaaataaaa taatgtagga taaaagcaac cttactcttt ttgtaaattg tatagactcc | | 1993 |
| caaatactag aaatgatcat ttaagttact atatatacca atatatatac tatatatacc | | 2053 |
| aataagaaga tgagaattaa ctttatgttc ctaaatttga cacttaatag ctatagcctc | | 2113 |
| cctgagatca tagagaagtg attgcctaag ataagttgta tttgtttttc tagttaccct | | 2173 |
| aaatcctgtc aggtaataaa agaatgatca ttgcaggctt tgtaaactcg ggtcactcac | | 2233 |
| tccacttggc tctccatgtt tttcatggtt ctagggtgt gttatgaacg aacctccttc | | 2293 |
| agtccaacta tccagacgtt cattctctct gccatttggc acgggtata cccaggatat | | 2353 |
| tatctaacgt ttctaacagg ggtgttaatg acattagcag caagagctgt aagtatcaag | | 2413 |

-continued

```
aattttattt tacaattcaa tggtccactt gaactgttaa aaaggctgag tacatctctc    2473
ttacaaggta gaccctcttt ccttggtcgt ggtcagtatt gtcctttcca ctagaagcga    2533
ggtgtgtact gcgtgcatgt ttgctgagcg ctcaccacgg gctaggctcc atgcccagtt    2593
cctgtgagga gaaaacacgt ttctatgtgc ccggcaggta ggaggcactc acaaaatgtt    2653
actttgtctt tacagaattt tctgaaggag agataaaaac tgagttaaat aaagatgatc    2713
agaatggatg agaaataact ttagacatta tttcattgaa ccttcccaac tgaaattatt    2773
ttatgatgtt ataacatgga tagtaactca agtagcaata agttacacag ttgtgccatt    2833
tgtgcttctt tctataaaac catcactcac gttttacagc tcctggtatt attgcctgca    2893
cattcttggt atcttagtat tattgttgtt gccagtgaaa aaaactcaaa gaagaaagaa    2953
tacacatgaa acattcagc ctctcacaatc caaaaagttt gatgaaggag aaaattcttt    3013
gggacagaac agttttttcta caacaaacaa tgtttgcaat cagaatcaag aaatagcctc    3073
gagacattca tcactaaagc agtgatcggg aaggctctga gggctgtttt ttttttttga    3133
tgttaacaga aaccaatctt agcacctttt caaggggttt gagtttgttg gaaaagcagt    3193
taactggggg gaaatggaca gttatagata aggaatttcc tgtacaccag attggaaatg    3253
gagtgaaaca agccctccca tgccatgtcc ccgtgggcca cgccttatgt aagaatattt    3313
ccatatttca gtgggcactc ccaacctcag cacttgtccg tagggtcaca cgcgtgccct    3373
gttgctgaat gtatgttgcg tatcccaagg cactgaagag gtggaaaaat aatcgtgtca    3433
atctggatga tagagagaaa ttaacttttc caaatgaatg tcttgcctta aaccctctat    3493
ttcctaaaat attgttccta aatggtattt tcaagtgtaa tattgtgaga acgctactgc    3553
agtagttgat gttgtgtgct gtaaaggatt ttaggaggaa tttgaaacag gatatttaag    3613
agtgtggata tttttaaaat gcaataaaca tctcagtatt tgaagggttt tcttaaagta    3673
tgtcaaatga ctacaatcca tagtgaaact gtaaacagta atggacgcca aattataggt    3733
agctgatttt gctggagagt ttaattacct tgtgcagtca aagagcgctt ccagaaggaa    3793
tctcttaaaa cataatgaga ggtttggtaa tgtgatattt taagcttatt cttttttctta    3853 aaagagagag gtgacgaagg aaggcaggaa tgaagaagca ctgcgtggcc tccggtggaa    3913 tgcacgggc acagccgcga ctctgcaggc agcttccccc ccatgcccag ggctctgcgc    3973
cgtcatgtga gacttaaaaa aaaagttgaa tgacttcgtg atactttgga cttctaaatt    4033
aaatttatca ggcataaatt atgtagaatt agaggctttg aaaataatac tggtaggttg    4093
ctcaaaggtt ttgaaagaga aatcgctagg taggttacta tctggctaat ccatttctta    4153
tccttgacaa tttaattcat atttgggaaa cttttaggga atgaaaaat aaaagtcact    4213 gagtctgggt gacatttttt aagaataata taaattcagt ttcaaactct tctcacatta    4273
aaattttgct gtgaactctt actaaaatga gttttaggtt ctgtaagtgg aaaaatgtgc    4333
ttttatttta tgggccattt ttaccacaac taatcttgcc ttggattact aagcatctcc    4393
tgcgatccca cagaggactg tggtggccac aggagctgaa                          4433
```

<210> SEQ ID NO 7
<211> LENGTH: 141
<212> TYPE: PRT
<213> ORGANISM: Homo sapiens

<400> SEQUENCE: 7

```
Ile Gly Val Glu Asn Met His Asn Tyr Cys Phe Val Phe Ala Leu Gly
 1               5                  10                  15
```

```
Tyr Leu Thr Val Cys Gln Val Thr Arg Val Tyr Ile Phe Asp Tyr Gly
         20                  25                  30

Gln Tyr Ser Ala Asp Phe Ser Gly Pro Met Met Ile Ile Thr Gln Lys
             35                  40                  45

Ile Thr Ser Leu Ala Cys Glu Ile His Asp Gly Met Phe Arg Lys Asp
 50                  55                  60

Glu Glu Leu Thr Ser Ser Gln Arg Asp Leu Ala Val Arg Arg Met Pro
 65                  70                  75                  80

Ser Leu Leu Glu Tyr Leu Ser Tyr Asn Cys Asn Phe Met Gly Ile Leu
                 85                  90                  95

Ala Gly Pro Leu Cys Ser Tyr Lys Asp Tyr Ile Thr Phe Ile Glu Gly
             100                 105                 110

Arg Ser Tyr His Ile Thr Gln Ser Gly Glu Asn Gly Lys Glu Glu Thr
         115                 120                 125

Gln Tyr Glu Arg Thr Glu Pro Ser Pro Asn Val Arg Ser
         130                 135                 140
```

<210> SEQ ID NO 8
<211> LENGTH: 1276
<212> TYPE: DNA
<213> ORGANISM: Homo sapiens
<220> FEATURE:
<221> NAME/KEY: CDS
<222> LOCATION: (1)...(1275)
<221> NAME/KEY: misc_feature
<222> LOCATION: (1)...(1276)
<223> OTHER INFORMATION: n = A,T,C or G

<400> SEQUENCE: 8

```
ata gga gtg gag aac atg cac aat tac tgc ttt gtg ttt gct ctg gga       48
Ile Gly Val Glu Asn Met His Asn Tyr Cys Phe Val Phe Ala Leu Gly
 1               5                  10                  15 tac ctc aca gtg tgc caa gtt act cga gtc tat atc ttt gac tat gga       96
Tyr Leu Thr Val Cys Gln Val Thr Arg Val Tyr Ile Phe Asp Tyr Gly
             20                  25                  30 caa tat tct gct gat ttt tca ggc cca atg atg atc att act cag aag      144
Gln Tyr Ser Ala Asp Phe Ser Gly Pro Met Met Ile Ile Thr Gln Lys
         35                  40                  45 atc act agt ttg gct tgc gaa ata cat gat ggg atg ttt cgg aag gat      192
Ile Thr Ser Leu Ala Cys Glu Ile His Asp Gly Met Phe Arg Lys Asp
 50                  55                  60 gaa gaa ctg act tcc tca cag agg gat tta gct gta agg cgc atg cca      240
Glu Glu Leu Thr Ser Ser Gln Arg Asp Leu Ala Val Arg Arg Met Pro
 65                  70                  75                  80 agc tta ctg gag tat ttg agt tac aac tgt aac ttc atg ggg atc ctg      288
Ser Leu Leu Glu Tyr Leu Ser Tyr Asn Cys Asn Phe Met Gly Ile Leu
                 85                  90                  95 gca ggc cca ctt tgc tct tac aaa gac tac att act ttc att gaa ggc      336
Ala Gly Pro Leu Cys Ser Tyr Lys Asp Tyr Ile Thr Phe Ile Glu Gly
             100                 105                 110 aga tca tac cat atc aca caa tct ggt gaa aat gga aaa gaa gag aca      384
Arg Ser Tyr His Ile Thr Gln Ser Gly Glu Asn Gly Lys Glu Glu Thr
         115                 120                 125 cag tat gaa aga aca gna gcc atc tcc aaa tgt aag gtc atg aga ttt      432
Gln Tyr Glu Arg Thr Xaa Ala Ile Ser Lys Cys Lys Val Met Arg Phe
         130                 135                 140 atc tgg agc ctt tac agc atg tat tgn act gcg gkt gtt cag aag ctc      480
Ile Trp Ser Leu Tyr Ser Met Tyr Xaa Thr Ala Xaa Val Gln Lys Leu
145                 150                 155                 160 tta gtt tgt ggg ctg tcc ttg tta ttt cac ttg acc atc tgt aca aca      528
```

```

Leu Val Cys Gly Leu Ser Leu Leu Phe His Leu Thr Ile Cys Thr Thr
                165                 170                 175 tta cct gtg gag tac aac att gat gag cat ttt caa gct aca gct tcg         576
Leu Pro Val Glu Tyr Asn Ile Asp Glu His Phe Gln Ala Thr Ala Ser
        180                 185                 190 tgg cca aca aag att atc tat ctg tat atc tct ctt ttg gct gcc aga         624
Trp Pro Thr Lys Ile Ile Tyr Leu Tyr Ile Ser Leu Leu Ala Ala Arg
            195                 200                 205 ccc aaa tac tat ttt gca tgg acg cta gct gat gcc att aat aat gct         672
Pro Lys Tyr Tyr Phe Ala Trp Thr Leu Ala Asp Ala Ile Asn Asn Ala
        210                 215                 220 gca ggc ttt ggt ttc aga ggg tat gac gaa aat gga gca gct cgc tgg         720
Ala Gly Phe Gly Phe Arg Gly Tyr Asp Glu Asn Gly Ala Ala Arg Trp
225                 230                 235                 240 gac tta att tcc aat ttg aga att caa caa ata gag atg tca aca agt         768
Asp Leu Ile Ser Asn Leu Arg Ile Gln Gln Ile Glu Met Ser Thr Ser
            245                 250                 255 ttc aag atg ttt ctt gat aat tgg aat att cag aca gct ctt tgg ccc         816
Phe Lys Met Phe Leu Asp Asn Trp Asn Ile Gln Thr Ala Leu Trp Pro
        260                 265                 270 aaa agg gtg tgt tat gaa cga acc tcc ttc agt cca act atc cag acg         864
Lys Arg Val Cys Tyr Glu Arg Thr Ser Phe Ser Pro Thr Ile Gln Thr
    275                 280                 285 ttc att ctc cct gcc att ntg gca cgg ggt ata ccc agg ata tta tct         912
Phe Ile Leu Pro Ala Ile Xaa Ala Arg Gly Ile Pro Arg Ile Leu Ser
290                 295                 300 aac gtt tct aac agg ggt gtt aat gac att agc agc aga gct atg aga         960
Asn Val Ser Asn Arg Gly Val Asn Asp Ile Ser Ser Arg Ala Met Arg
305                 310                 315                 320 aat aac ttt aga cat tat ttc att gaa cct tcc caa ctg aaa tta ttt        1008
Asn Asn Phe Arg His Tyr Phe Ile Glu Pro Ser Gln Leu Lys Leu Phe
            325                 330                 335 tat gat gtt mta aca tgg ata gta aac tca agt agc aat aag tta cac        1056
Tyr Asp Val Xaa Thr Trp Ile Val Asn Ser Ser Ser Asn Lys Leu His
        340                 345                 350 agk tgk gsc att tgt gct tct ttc tat waa acc atc act cac rkt tya        1104
Xaa Xaa Xaa Ile Cys Ala Ser Phe Tyr Xaa Thr Ile Thr His Xaa Xaa
    355                 360                 365 cag gtc cgg ttt att gcc gga cat act ggt tcc tcg ata atg gcg tgc        1152
Gln Val Arg Phe Ile Ala Gly His Thr Gly Ser Ser Ile Met Ala Cys
370                 375                 380 cgg aca acg cgg aga aag gta ctg gaa gtt ccg ctc cac caa gtc gtg        1200
Arg Thr Thr Arg Arg Lys Val Leu Glu Val Pro Leu His Gln Val Val
385                 390                 395                 400 ggg gac act tgg gac agc tct tcc aca agc gcg ccg aag ccg gac aca        1248
Gly Asp Thr Trp Asp Ser Ser Ser Thr Ser Ala Pro Lys Pro Asp Thr
            405                 410                 415 acg acg ggg cgg ggg ggt ggg gca acc c                                  1276
Thr Thr Gly Arg Gly Gly Gly Ala Thr
        420                 425

<210> SEQ ID NO 9
<211> LENGTH: 425
<212> TYPE: PRT
<213> ORGANISM: Homo sapiens
<220> FEATURE:
<221> NAME/KEY: VARIANT
<222> LOCATION: (1)...(425)
<223> OTHER INFORMATION: Xaa = Any Amino Acid

<400> SEQUENCE: 9
```

```
Ile Gly Val Glu Asn Met His Asn Tyr Cys Phe Val Phe Ala Leu Gly
 1               5                  10                  15
Tyr Leu Thr Val Cys Gln Val Thr Arg Val Tyr Ile Phe Asp Tyr Gly
            20                  25                  30
Gln Tyr Ser Ala Asp Phe Ser Gly Pro Met Met Ile Ile Thr Gln Lys
        35                  40                  45
Ile Thr Ser Leu Ala Cys Glu Ile His Asp Gly Met Phe Arg Lys Asp
 50                  55                  60
Glu Glu Leu Thr Ser Ser Gln Arg Asp Leu Ala Val Arg Arg Met Pro
65                  70                  75                  80
Ser Leu Leu Glu Tyr Leu Ser Tyr Asn Cys Asn Phe Met Gly Ile Leu
                85                  90                  95
Ala Gly Pro Leu Cys Ser Tyr Lys Asp Tyr Ile Thr Phe Ile Glu Gly
            100                 105                 110
Arg Ser Tyr His Ile Thr Gln Ser Gly Glu Asn Gly Lys Glu Glu Thr
        115                 120                 125
Gln Tyr Glu Arg Thr Xaa Ala Ile Ser Lys Cys Lys Val Met Arg Phe
    130                 135                 140
Ile Trp Ser Leu Tyr Ser Met Tyr Xaa Thr Ala Xaa Val Gln Lys Leu
145                 150                 155                 160
Leu Val Cys Gly Leu Ser Leu Phe His Leu Thr Ile Cys Thr Thr
                165                 170                 175
Leu Pro Val Glu Tyr Asn Ile Asp Glu His Phe Gln Ala Thr Ala Ser
            180                 185                 190
Trp Pro Thr Lys Ile Ile Tyr Leu Tyr Ile Ser Leu Leu Ala Ala Arg
        195                 200                 205
Pro Lys Tyr Tyr Phe Ala Trp Thr Leu Ala Asp Ala Ile Asn Asn Ala
    210                 215                 220
Ala Gly Phe Gly Phe Arg Gly Tyr Asp Glu Asn Gly Ala Ala Arg Trp
225                 230                 235                 240
Asp Leu Ile Ser Asn Leu Arg Ile Gln Gln Ile Glu Met Ser Thr Ser
                245                 250                 255
Phe Lys Met Phe Leu Asp Asn Trp Asn Ile Gln Thr Ala Leu Trp Pro
            260                 265                 270
Lys Arg Val Cys Tyr Glu Arg Thr Ser Phe Ser Pro Thr Ile Gln Thr
        275                 280                 285
Phe Ile Leu Pro Ala Ile Xaa Ala Arg Gly Ile Pro Arg Ile Leu Ser
    290                 295                 300
Asn Val Ser Asn Arg Gly Val Asn Asp Ile Ser Ser Arg Ala Met Arg
305                 310                 315                 320
Asn Asn Phe Arg His Tyr Phe Ile Glu Pro Ser Gln Leu Lys Leu Phe
                325                 330                 335
Tyr Asp Val Xaa Thr Trp Ile Val Asn Ser Ser Ser Asn Lys Leu His
            340                 345                 350
Xaa Xaa Xaa Ile Cys Ala Ser Phe Tyr Xaa Thr Ile Thr His Xaa Xaa
        355                 360                 365
Gln Val Arg Phe Ile Ala Gly His Thr Gly Ser Ser Ile Met Ala Cys
    370                 375                 380
Arg Thr Thr Arg Arg Lys Val Leu Glu Val Pro Leu His Gln Val Val
385                 390                 395                 400
Gly Asp Thr Trp Asp Ser Ser Thr Ser Ala Pro Lys Pro Asp Thr
                405                 410                 415
Thr Thr Gly Arg Gly Gly Gly Ala Thr
```

-continued

```
                              420               425

<210> SEQ ID NO 10
<211> LENGTH: 29
<212> TYPE: DNA
<213> ORGANISM: Homo sapiens

<400> SEQUENCE: 10
tgaggtatcc cagagcaaac acaaagcag                                    29

<210> SEQ ID NO 11
<211> LENGTH: 28
<212> TYPE: DNA
<213> ORGANISM: Homo sapiens

<400> SEQUENCE: 11
tcagttcttc atccttccga aacatccc                                     28
```

What is claimed is:

1. An isolated ARP3 polypeptide, comprising the amino acid sequence shown as SEQ ID NO:5.

2. An isolated ARP3 polypeptide fragment consisting of a fragment of SEQ ID NO: 5, wherein said fragment comprises at least ten contiguous amino acids of SEQ ID NO:5.

3. An ARP3 fusion protein, comprising a heterologous polypeptide fused to an ARP3 polypeptide fragment consisting of a fragment of SEQ ID NO: 5, wherein said fragment comprises at least ten contiguous amino acids of SEQ ID NO: 5.

* * * * *